(12) United States Patent
Hacohen et al.

(10) Patent No.: US 8,273,357 B2
(45) Date of Patent: Sep. 25, 2012

(54) ANTIGEN-CARBOHYDRATE CONJUGATES

(75) Inventors: Nir Hacohen, Cambridge, MA (US); Eddie Adams, Brighton, MA (US); Peter Seeberger, Zurich (CH)

(73) Assignees: Massachusetts Institute of Technology, Cambridge, MA (US); Whitehead Institute for Biomedical Research, Cambridge, MA (US); The General Hospital Corporation, Boston, MA (US)

( * ) Notice: Subject to any disclaimer, the term of this patent is extended or adjusted under 35 U.S.C. 154(b) by 1025 days.

(21) Appl. No.: 11/632,442

(22) PCT Filed: Jul. 18, 2005

(86) PCT No.: PCT/US2005/025461
§ 371 (c)(1),
(2), (4) Date: Jul. 3, 2008

(87) PCT Pub. No.: WO2006/093524
PCT Pub. Date: Sep. 8, 2006

(65) Prior Publication Data
US 2009/0004218 A1  Jan. 1, 2009

Related U.S. Application Data

(60) Provisional application No. 60/588,671, filed on Jul. 16, 2004.

(51) Int. Cl.
*A61K 39/00* (2006.01)
(52) U.S. Cl. ............................ 424/193.1; 530/300
(58) Field of Classification Search .................. None
See application file for complete search history.

(56) References Cited

U.S. PATENT DOCUMENTS

| | | | |
|---|---|---|---|
| 4,356,170 A | 10/1982 | Jennings et al. | |
| 5,284,934 A | 2/1994 | Allen, Jr. | |
| 5,985,852 A | 11/1999 | Nagy et al. | |
| 2002/0187131 A1 | 12/2002 | Hawiger et al. | |
| 2004/0047866 A1 | 3/2004 | Harn et al. | |

FOREIGN PATENT DOCUMENTS

| | | |
|---|---|---|
| WO | PCT/ISA/210 | 5/2008 |
| WO | PCT/ISA/237 | 5/2008 |

OTHER PUBLICATIONS

Adams et al, ChemBioChem, 2008, 9:294-303.*
Seeberger et al, Nature Reviews/Drug Discovery, Sep. 2005, 4:751-763.*
Seeberger et al, Nature, Apr. 26, 2007, 446:1046-1051.*
Werz et al, Chem. Eur. J., 2005, 11:3194-3206.*
Werz et al, Chemical Biology, 2007, 2:668-691.*
Cunto-Amesty et al, International J. For Parasitology, 2003, 33:597-613.*
Lucas et al, Clinical Infectious Diseases, 2005, 41:705-712.*
Hecht et al, Current Opinion in Chemical Biology, 2009, 13:354-359.*
Ratner et al. "A Linear Synthesis of Branded High-Mannose Oligosaccharides from the HIV-1 Viral Surface Envelope Glycoprotein gp120." Eur. J. Org. Chem. 826-833 (2002).
Ratner et al. "Probing Protein—Carbohydrate Interactions with Microarrays of Synthetic Oligosaccharides." ChemBioChem 5: 379-383 (2004).
Cui et al. "Physical characterization and macrophage cell uptake of mannan-coated nanoparticles." Drug Dev Ind Pharm. 29(6): 689-700 (2003).
Bonifaz et al. In Vivo Targeting of Antigens to Maturing Dendritic Cells via the DEC-205 Receptor Improves T Cell Vaccination J. Exp Med 199(6): 815-824 (2004).
Hawiger et al. "Dendritic Cells Induce Peripheral T Cell Unresponsiveness Under Steady State Conditions In Vivo." J. Exp. Med. 194(6): 769-779 (2001).
Mahnke et al. "Induction of CD4+/CD25+ regulatory T cells by targeting of antigens to immature dendritic cells." Blood 101(12): 4862-4869 (2003).
Bonifaz et al. "Efficient Targeting of Protein Antigen to the Dendritic Cell Receptor DEC-205 in the Steady State Leads to Antigen Presentation on Major Histocompatability Complex Class I Products and Peripheral CD8+ T Cell Tolerance." J. Exp. Med. 196(12): 1627-1638 (2002).
Van Kooyk et al. "DC-Sign: escape mechanism for pathogens." Nat. Rev Immunol. 3(9): 697-709 (2003).

\* cited by examiner

*Primary Examiner* — Nita M Minnifield
(74) *Attorney, Agent, or Firm* — Edwards Wildman Palmer LLP; Peter C. Lauro, Esq.

(57) ABSTRACT

The present invention generally relates to compositions comprising antigen-carbohydrate conjugates and methods of immune modulation featuring these reagents.

49 Claims, 10 Drawing Sheets

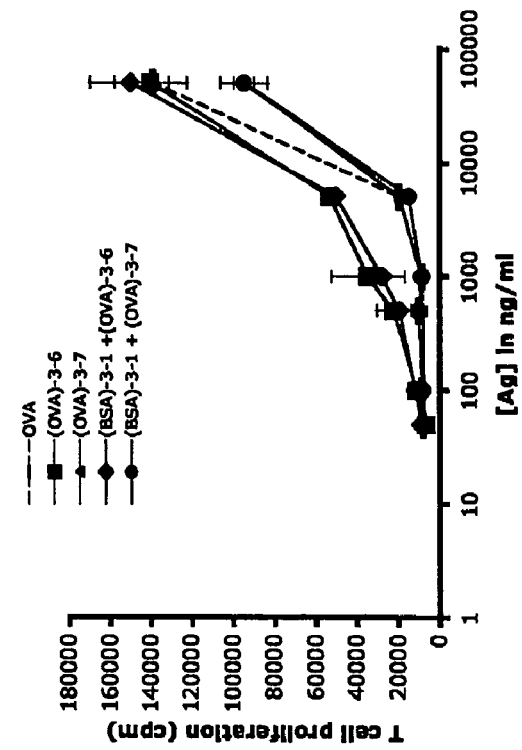
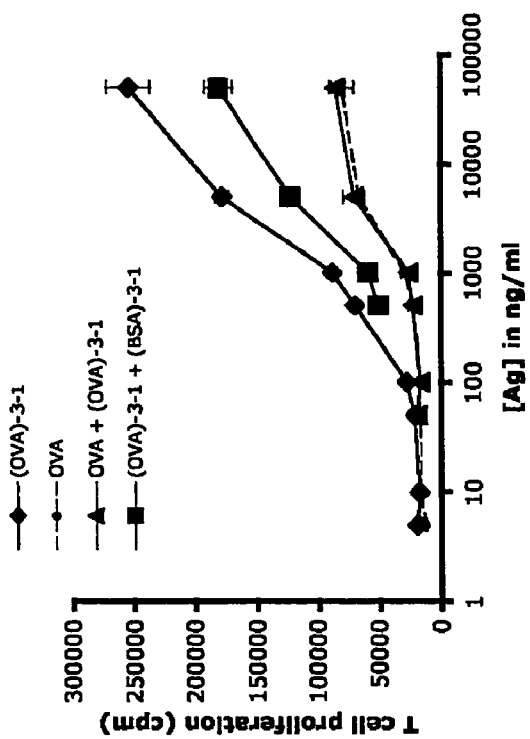
FIG. 3B
FIG. 3A

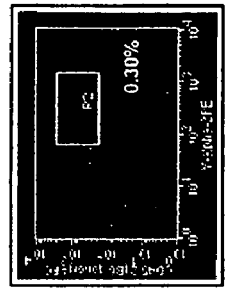
FIG. 6A
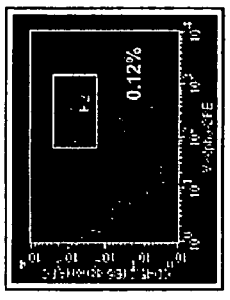
FIG. 6B
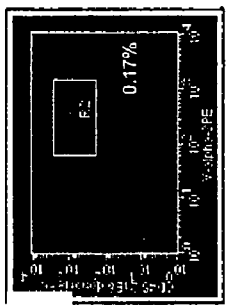
FIG. 6C
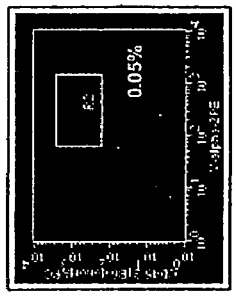
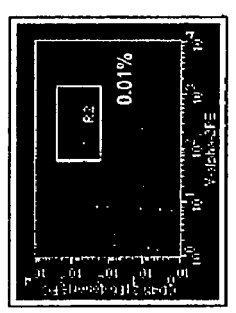

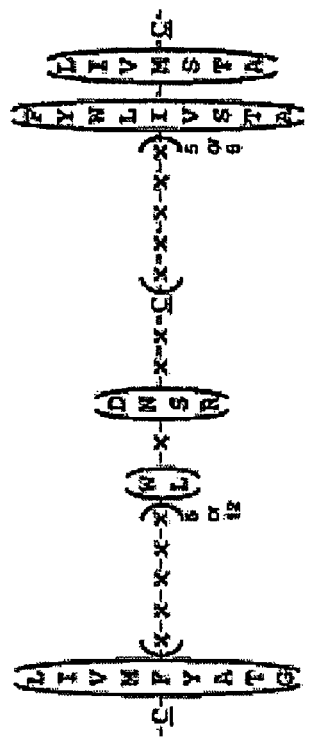
FIG. 9A
FIG. 9B
FIG. 9C

SEQUENCE LISTING

<160> NUMBER OF SEQ ID NOS: 15

<210> SEQ ID NO 1
<211> LENGTH: 1456
<212> TYPE: PRT
<213> ORGANISM: Homo sapiens

<400> SEQUENCE: 1

```
Met Arg Leu Pro Leu Leu Leu Val Phe Ala Ser Val Ile Pro Gly Ala
1               5                   10                  15

Val Leu Leu Leu Asp Thr Arg Gln Phe Leu Ile Tyr Asn Glu Asp His
            20                  25                  30

Lys Arg Cys Val Asp Ala Val Ser Pro Ser Ala Val Gln Thr Ala Ala
        35                  40                  45

Cys Asn Gln Asp Ala Glu Ser Gln Lys Phe Arg Trp Val Ser Glu Ser
    50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
            115                 120                 125

Leu Tyr Lys Gly Ser Gly Leu Trp Ser Arg Trp Lys Ile Tyr Gly Thr
        130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
    210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
    290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Thr Thr Leu Asn Ser Phe Val Ile
            340                 345                 350

Pro Ser Glu Ser Asp Val Pro Thr His Cys Pro Ser Gln Trp Trp Pro
        355                 360                 365

Tyr Ala Gly His Cys Tyr Lys Ile His Arg Asp Glu Lys Lys Ile Gln
    370                 375                 380

Arg Asp Ala Leu Thr Thr Cys Arg Lys Glu Gly Gly Asp Leu Thr Ser
385                 390                 395                 400

Ile His Thr Ile Glu Glu Leu Asp Phe Ile Ile Ser Gln Leu Gly Tyr
                405                 410                 415

Glu Pro Asn Asp Glu Leu Trp Ile Gly Leu Asn Asp Ile Lys Ile Gln
```

```
                420             425             430
Met Tyr Phe Glu Trp Ser Asp Gly Thr Pro Val Thr Phe Thr Lys Trp
            435                 440                 445

Leu Arg Gly Glu Pro Ser His Glu Asn Asn Arg Gln Glu Asp Cys Val
    450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
                500                 505                 510

Phe Tyr Cys Tyr Met Ile Gly His Thr Leu Ser Thr Phe Ala Glu Ala
        515                 520                 525

Asn Gln Thr Cys Asn Asn Glu Asn Ala Tyr Leu Thr Thr Ile Glu Asp
    530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
                580                 585                 590

Met Pro Gly Arg Lys Pro Gly Cys Val Ala Met Arg Thr Gly Ile Ala
            595                 600                 605

Gly Gly Leu Trp Asp Val Leu Lys Cys Asp Glu Lys Ala Lys Phe Val
        610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
        675                 680                 685

Ser Ile Asn Asn Lys Glu Glu Gln Gln Thr Ile Trp Arg Leu Ile Thr
    690                 695                 700

Ala Ser Gly Ser Tyr His Lys Leu Phe Trp Leu Gly Leu Thr Tyr Gly
705                 710                 715                 720

Ser Pro Ser Glu Gly Phe Thr Trp Ser Asp Gly Ser Pro Val Ser Tyr
                725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Thr Met Ser Trp Asn Asp Ile Asn
        755                 760                 765

Cys Glu His Leu Asn Asn Trp Ile Cys Gln Ile Gln Lys Gly Gln Thr
    770                 775                 780

Pro Lys Pro Glu Pro Thr Pro Ala Pro Gln Asp Asn Pro Pro Val Thr
785                 790                 795                 800

Glu Asp Gly Trp Val Ile Tyr Lys Asp Tyr Gln Tyr Tyr Phe Ser Lys
                805                 810                 815

Glu Lys Glu Thr Met Asp Asn Ala Arg Ala Phe Cys Lys Arg Asn Phe
            820                 825                 830

Gly Asp Leu Val Ser Ile Gln Ser Glu Ser Glu Lys Lys Phe Leu Trp
        835                 840                 845
```

```
Lys Tyr Val Asn Arg Asn Asp Ala Gln Ser Ala Tyr Phe Ile Gly Leu
850                 855                 860

Leu Ile Ser Leu Asp Lys Lys Phe Ala Trp Met Asp Gly Ser Lys Val
865                 870                 875                 880

Asp Tyr Val Ser Trp Ala Thr Gly Glu Pro Asn Phe Ala Asn Glu Asp
                885                 890                 895

Glu Asn Cys Val Thr Met Tyr Ser Asn Ser Gly Phe Trp Asn Asp Ile
            900                 905                 910

Asn Cys Gly Tyr Pro Asn Ala Phe Ile Cys Gln Arg His Asn Ser Ser
        915                 920                 925

Ile Asn Ala Thr Thr Val Met Pro Thr Met Pro Ser Val Pro Ser Gly
930                 935                 940

Cys Lys Glu Gly Trp Asn Phe Tyr Ser Asn Lys Cys Phe Lys Ile Phe
945                 950                 955                 960

Gly Phe Met Glu Glu Glu Arg Lys Asn Trp Gln Glu Ala Arg Lys Ala
                965                 970                 975

Cys Ile Gly Phe Gly Gly Asn Leu Val Ser Ile Gln Asn Glu Lys Glu
            980                 985                 990

Gln Ala Phe Leu Thr Tyr His Met Lys Asp Ser Thr Phe Ser Ala Trp
        995                 1000                1005

Thr Gly Leu Asn Asp Val Asn Ser Glu His Thr Phe Leu Trp Thr
    1010                1015                1020

Asp Gly Arg Gly Val His Tyr Thr Asn Trp Gly Lys Gly Tyr Pro
    1025                1030                1035

Gly Gly Arg Arg Ser Ser Leu Ser Tyr Glu Asp Ala Asp Cys Val
    1040                1045                1050

Val Ile Ile Gly Gly Ala Ser Asn Glu Ala Gly Lys Trp Met Asp
    1055                1060                1065

Asp Thr Cys Asp Ser Lys Arg Gly Tyr Ile Cys Gln Thr Arg Ser
    1070                1075                1080

Asp Pro Ser Leu Thr Asn Pro Pro Ala Thr Ile Gln Thr Asp Gly
    1085                1090                1095

Phe Val Lys Tyr Gly Lys Ser Ser Tyr Ser Leu Met Arg Gln Lys
    1100                1105                1110

Phe Gln Trp His Glu Ala Glu Thr Tyr Cys Lys Leu His Asn Ser
    1115                1120                1125

Leu Ile Ala Ser Ile Leu Asp Pro Tyr Ser Asn Ala Phe Ala Trp
    1130                1135                1140

Leu Gln Met Glu Thr Ser Asn Glu Arg Val Trp Ile Ala Leu Asn
    1145                1150                1155

Ser Asn Leu Thr Asp Asn Gln Tyr Thr Trp Thr Asp Lys Trp Arg
    1160                1165                1170

Val Arg Tyr Thr Asn Trp Ala Ala Asp Glu Pro Lys Leu Lys Ser
    1175                1180                1185

Ala Cys Val Tyr Leu Asp Leu Asp Gly Tyr Trp Lys Thr Ala His
    1190                1195                1200

Cys Asn Glu Ser Phe Tyr Phe Leu Cys Lys Arg Ser Asp Glu Ile
    1205                1210                1215

Pro Ala Thr Glu Pro Pro Gln Leu Pro Gly Arg Cys Pro Glu Ser
    1220                1225                1230

Asp His Thr Ala Trp Ile Pro Phe His Gly His Cys Tyr Tyr Ile
    1235                1240                1245

Glu Ser Ser Tyr Thr Arg Asn Trp Gly Gln Ala Ser Leu Glu Cys
    1250                1255                1260
```

```
Leu Arg Met Gly Ser Ser Leu Val Ser Ile Glu Ser Ala Ala Glu
    1265                1270                1275

Ser Ser Phe Leu Ser Tyr Arg Val Glu Pro Leu Lys Ser Lys Thr
1280                1285                1290

Asn Phe Trp Ile Gly Leu Phe Arg Asn Val Glu Gly Thr Trp Leu
    1295                1300                1305

Trp Ile Asn Asn Ser Pro Val Ser Phe Val Asn Trp Asn Thr Gly
    1310                1315                1320

Asp Pro Ser Gly Glu Arg Asn Asp Cys Val Ala Leu His Ala Ser
    1325                1330                1335

Ser Gly Phe Trp Ser Asn Ile His Cys Ser Ser Tyr Lys Gly Tyr
    1340                1345                1350

Ile Cys Lys Arg Pro Lys Ile Ile Asp Ala Lys Pro Thr His Glu
    1355                1360                1365

Leu Leu Thr Thr Lys Ala Asp Thr Arg Lys Met Asp Pro Ser Lys
    1370                1375                1380

Pro Ser Ser Asn Val Ala Gly Val Val Ile Ile Val Ile Leu Leu
    1385                1390                1395

Ile Leu Thr Gly Ala Gly Leu Ala Ala Tyr Phe Phe Tyr Lys Lys
    1400                1405                1410

Arg Arg Val His Leu Pro Gln Glu Gly Ala Phe Glu Asn Thr Leu
    1415                1420                1425

Tyr Phe Asn Ser Gln Ser Ser Pro Gly Thr Ser Asp Met Lys Asp
    1430                1435                1440

Leu Val Gly Asn Ile Glu Gln Asn Glu His Ser Val Ile
    1445                1450                1455

<210> SEQ ID NO 2
<211> LENGTH: 1722
<212> TYPE: PRT
<213> ORGANISM: Homo sapiens

<400> SEQUENCE: 2

Met Arg Thr Gly Trp Ala Thr Pro Arg Arg Pro Ala Gly Leu Leu Met
1               5                   10                  15

Leu Leu Phe Trp Phe Phe Asp Leu Ala Glu Pro Ser Gly Arg Ala Ala
                20                  25                  30

Asn Asp Pro Phe Thr Ile Val His Gly Asn Thr Gly Lys Cys Ile Lys
                35                  40                  45

Pro Val Tyr Gly Trp Ile Val Ala Asp Asp Cys Asp Glu Thr Glu Asp
        50                  55                  60

Lys Leu Trp Lys Trp Val Ser Gln His Arg Leu Phe His Leu His Ser
65              70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
                100                 105                 110

His Ser Leu Tyr Gly Ala Ala Arg Tyr Arg Leu Ala Leu Lys Asp Gly
            115                 120                 125

His Gly Thr Ala Ile Ser Asn Ala Ser Asp Val Trp Lys Lys Gly Gly
        130                 135                 140

Ser Glu Glu Ser Leu Cys Asp Gln Pro Tyr His Glu Ile Tyr Thr Arg
145             150                 155                 160

Asp Gly Asn Ser Tyr Gly Arg Pro Cys Glu Phe Pro Phe Leu Ile Asp
                165                 170                 175
```

```
Gly Thr Trp His His Asp Cys Ile Leu Asp Glu Asp His Ser Gly Pro
            180                 185                 190
Trp Cys Ala Thr Thr Leu Asn Tyr Glu Tyr Asp Arg Lys Trp Gly Ile
            195                 200                 205
Cys Leu Lys Pro Glu Asn Gly Cys Glu Asp Asn Trp Glu Lys Asn Glu
            210                 215                 220
Gln Phe Gly Ser Cys Tyr Gln Phe Asn Thr Gln Thr Ala Leu Ser Trp
225                 230                 235                 240
Lys Glu Ala Tyr Val Ser Cys Gln Asn Gln Gly Ala Asp Leu Leu Ser
            245                 250                 255
Ile Asn Ser Ala Ala Glu Leu Thr Tyr Leu Lys Glu Lys Glu Gly Ile
            260                 265                 270
Ala Lys Ile Phe Trp Ile Gly Leu Asn Gln Leu Tyr Ser Ala Arg Gly
            275                 280                 285
Trp Glu Trp Ser Asp His Lys Pro Leu Asn Phe Leu Asn Trp Asp Pro
            290                 295                 300
Asp Arg Pro Ser Ala Pro Thr Ile Gly Gly Ser Ser Cys Ala Arg Met
305                 310                 315                 320
Asp Ala Glu Ser Gly Leu Trp Gln Ser Phe Ser Cys Glu Ala Gln Leu
                325                 330                 335
Pro Tyr Val Cys Arg Lys Pro Leu Asn Asn Thr Val Glu Leu Thr Asp
            340                 345                 350
Val Trp Thr Tyr Ser Asp Thr Arg Cys Asp Ala Gly Trp Leu Pro Asn
            355                 360                 365
Asn Gly Phe Cys Tyr Leu Leu Val Asn Glu Ser Asn Ser Trp Asp Lys
            370                 375                 380
Ala His Ala Lys Cys Lys Ala Phe Ser Ser Asp Leu Ile Ser Ile His
385                 390                 395                 400
Ser Leu Ala Asp Val Glu Val Val Val Thr Lys Leu His Asn Glu Asp
                405                 410                 415
Ile Lys Glu Glu Val Trp Ile Gly Leu Lys Asn Ile Asn Ile Pro Thr
            420                 425                 430
Leu Phe Gln Trp Ser Asp Gly Thr Glu Val Thr Leu Thr Tyr Trp Asp
            435                 440                 445
Glu Asn Glu Pro Asn Val Pro Tyr Asn Lys Thr Pro Asn Cys Val Ser
            450                 455                 460
Tyr Leu Gly Glu Leu Gly Gln Trp Lys Val Gln Ser Cys Glu Glu Lys
465                 470                 475                 480
Leu Lys Tyr Val Cys Lys Arg Lys Gly Glu Lys Leu Asn Asp Ala Ser
                485                 490                 495
Ser Asp Lys Met Cys Pro Pro Asp Glu Gly Trp Lys Arg His Gly Glu
            500                 505                 510
Thr Cys Tyr Lys Ile Tyr Glu Asp Glu Val Pro Phe Gly Thr Asn Cys
            515                 520                 525
Asn Leu Thr Ile Thr Ser Arg Phe Glu Gln Glu Tyr Leu Asn Asp Leu
            530                 535                 540
Met Lys Lys Tyr Asp Lys Ser Leu Arg Lys Tyr Phe Trp Thr Gly Leu
545                 550                 555                 560
Arg Asp Val Asp Ser Cys Gly Glu Tyr Asn Trp Ala Thr Val Gly Gly
                565                 570                 575
Arg Arg Arg Ala Val Thr Phe Ser Asn Trp Asn Phe Leu Glu Pro Ala
            580                 585                 590
Ser Pro Gly Gly Cys Val Ala Met Ser Thr Gly Lys Ser Val Gly Lys
```

```
                    595                 600                 605
Trp Glu Val Lys Asp Cys Arg Ser Phe Lys Ala Leu Ser Ile Cys Lys
610                 615                 620

Lys Met Ser Gly Pro Leu Gly Pro Glu Glu Ala Ser Pro Lys Pro Asp
625                 630                 635                 640

Asp Pro Cys Pro Glu Gly Trp Gln Ser Phe Pro Ala Ser Leu Ser Cys
                645                 650                 655

Tyr Lys Val Phe His Ala Glu Arg Ile Val Arg Lys Arg Asn Trp Glu
            660                 665                 670

Glu Ala Glu Arg Phe Cys Gln Ala Leu Gly Ala His Leu Ser Ser Phe
        675                 680                 685

Ser His Val Asp Glu Ile Lys Glu Phe Leu His Phe Leu Thr Asp Gln
    690                 695                 700

Phe Ser Gly Gln His Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Thr
                725                 730                 735

Ile Ile Met Pro Asn Glu Phe Gln Gln Asp Tyr Asp Ile Arg Asp Cys
            740                 745                 750

Ala Ala Val Lys Val Phe His Arg Pro Trp Arg Arg Gly Trp His Phe
        755                 760                 765

Tyr Asp Asp Arg Glu Phe Ile Tyr Leu Arg Pro Phe Ala Cys Asp Thr
770                 775                 780

Lys Leu Glu Trp Val Cys Gln Ile Pro Lys Gly Arg Thr Pro Lys Thr
785                 790                 795                 800

Pro Asp Trp Tyr Asn Pro Asp Arg Ala Gly Ile His Gly Pro Pro Leu
                805                 810                 815

Ile Ile Glu Gly Ser Glu Tyr Trp Phe Val Ala Asp Leu His Leu Asn
            820                 825                 830

Tyr Glu Glu Ala Val Leu Tyr Cys Ala Ser Asn His Ser Phe Leu Ala
        835                 840                 845

Thr Ile Thr Ser Phe Val Gly Leu Lys Ala Ile Lys Asn Lys Ile Ala
    850                 855                 860

Asn Ile Ser Gly Asp Gly Gln Lys Trp Trp Ile Arg Ile Ser Glu Trp
865                 870                 875                 880

Pro Ile Asp Asp His Phe Thr Tyr Ser Arg Tyr Pro Trp His Arg Phe
                885                 890                 895

Pro Val Thr Phe Gly Glu Glu Cys Leu Tyr Met Ser Ala Lys Thr Trp
            900                 905                 910

Leu Ile Asp Leu Gly Lys Pro Thr Asp Cys Ser Thr Lys Leu Pro Phe
        915                 920                 925

Ile Cys Glu Lys Tyr Asn Val Ser Ser Leu Glu Lys Tyr Ser Pro Asp
    930                 935                 940

Ser Ala Ala Lys Val Gln Cys Ser Glu Gln Trp Ile Pro Phe Gln Asn
945                 950                 955                 960

Lys Cys Phe Leu Lys Ile Lys Pro Val Ser Leu Thr Phe Ser Gln Ala
                965                 970                 975

Ser Asp Thr Cys His Ser Tyr Gly Gly Thr Leu Pro Ser Val Leu Ser
            980                 985                 990

Gln Ile Glu Gln Asp Phe Ile Thr Ser Leu Leu Pro Asp Met Glu Ala
        995                 1000                1005

Thr Leu Trp Ile Gly Leu Arg Trp Thr Ala Tyr Glu Lys Ile Asn
    1010                1015                1020
```

```
Lys Trp Thr Asp Asn Arg Glu Leu Thr Tyr Ser Asn Phe His Pro
    1025                1030                1035

Leu Leu Val Ser Gly Arg Leu Arg Ile Pro Glu Asn Phe Phe Glu
    1040                1045                1050

Glu Glu Ser Arg Tyr His Cys Ala Leu Ile Leu Asn Leu Gln Lys
    1055                1060                1065

Ser Pro Phe Thr Gly Thr Trp Asn Phe Thr Ser Cys Ser Glu Arg
    1070                1075                1080

His Phe Val Ser Leu Cys Gln Lys Tyr Ser Glu Val Lys Ser Arg
    1085                1090                1095

Gln Thr Leu Gln Asn Ala Ser Glu Thr Val Lys Tyr Leu Asn Asn
    1100                1105                1110

Leu Tyr Lys Ile Ile Pro Lys Thr Leu Thr Trp His Ser Ala Lys
    1115                1120                1125

Arg Glu Cys Leu Lys Ser Asn Met Gln Leu Val Ser Ile Thr Asp
    1130                1135                1140

Pro Tyr Gln Gln Ala Phe Leu Ser Val Gln Ala Leu Leu His Asn
    1145                1150                1155

Ser Ser Leu Trp Ile Gly Leu Phe Ser Gln Asp Asp Glu Leu Asn
    1160                1165                1170

Phe Gly Trp Ser Asp Gly Lys Arg Leu His Phe Ser Arg Trp Ala
    1175                1180                1185

Glu Thr Asn Gly Gln Leu Glu Asp Cys Val Val Leu Asp Thr Asp
    1190                1195                1200

Gly Phe Trp Lys Thr Val Asp Cys Asn Asp Asn Gln Pro Gly Ala
    1205                1210                1215

Ile Cys Tyr Tyr Ser Gly Asn Glu Thr Glu Lys Glu Val Lys Pro
    1220                1225                1230

Val Asp Ser Val Lys Cys Pro Ser Pro Val Leu Asn Thr Pro Trp
    1235                1240                1245

Ile Pro Phe Gln Asn Cys Cys Tyr Asn Phe Ile Ile Thr Lys Asn
    1250                1255                1260

Arg His Met Ala Thr Thr Gln Asp Glu Val His Thr Lys Cys Gln
    1265                1270                1275

Lys Leu Asn Pro Lys Ser His Ile Leu Ser Ile Arg Asp Glu Lys
    1280                1285                1290

Glu Asn Asn Phe Val Leu Glu Gln Leu Leu Tyr Phe Asn Tyr Met
    1295                1300                1305

Ala Ser Trp Val Met Leu Gly Ile Thr Tyr Arg Asn Asn Ser Leu
    1310                1315                1320

Met Trp Phe Asp Lys Thr Pro Leu Ser Tyr Thr His Trp Arg Ala
    1325                1330                1335

Gly Arg Pro Thr Ile Lys Asn Glu Lys Phe Leu Ala Gly Leu Ser
    1340                1345                1350

Thr Asp Gly Phe Trp Asp Ile Gln Thr Phe Lys Val Ile Glu Glu
    1355                1360                1365

Ala Val Tyr Phe His Gln His Ser Ile Leu Ala Cys Lys Ile Glu
    1370                1375                1380

Met Val Asp Tyr Lys Glu Glu His Asn Thr Thr Leu Pro Gln Phe
    1385                1390                1395

Met Pro Tyr Glu Asp Gly Ile Tyr Ser Val Ile Gln Lys Lys Val
    1400                1405                1410

Thr Trp Tyr Glu Ala Leu Asn Met Cys Ser Gln Ser Gly Gly His
    1415                1420                1425
```

```
Leu Ala Ser Val His Asn Gln Asn Gly Gln Leu Phe Leu Glu Asp
    1430                1435                1440

Ile Val Lys Arg Asp Gly Phe Pro Leu Trp Val Gly Leu Ser Ser
1445                1450                1455

His Asp Gly Ser Glu Ser Ser Phe Glu Trp Ser Asp Gly Ser Thr
    1460                1465                1470

Phe Asp Tyr Ile Pro Trp Lys Gly Gln Thr Ser Pro Gly Asn Cys
1475                1480                1485

Val Leu Leu Asp Pro Lys Gly Thr Trp Lys His Glu Lys Cys Asn
    1490                1495                1500

Ser Val Lys Asp Gly Ala Ile Cys Tyr Lys Pro Thr Lys Ser Lys
1505                1510                1515

Lys Leu Ser Arg Leu Thr Tyr Ser Ser Arg Cys Pro Ala Ala Lys
    1520                1525                1530

Glu Asn Gly Ser Arg Trp Ile Gln Tyr Lys Gly His Cys Tyr Lys
1535                1540                1545

Ser Asp Gln Ala Leu His Ser Phe Ser Glu Ala Lys Lys Leu Cys
    1550                1555                1560

Ser Lys His Asp His Ser Ala Thr Ile Val Ser Ile Lys Asp Glu
1565                1570                1575

Asp Glu Asn Lys Phe Val Ser Arg Leu Met Arg Glu Asn Asn Asn
    1580                1585                1590

Ile Thr Met Arg Val Trp Leu Gly Leu Ser Gln His Ser Val Asp
1595                1600                1605

Gln Ser Trp Ser Trp Leu Asp Gly Ser Glu Val Thr Phe Val Lys
    1610                1615                1620

Trp Glu Asn Lys Ser Lys Ser Gly Val Gly Arg Cys Ser Met Leu
1625                1630                1635

Ile Ala Ser Asn Glu Thr Trp Lys Lys Val Glu Cys Glu His Gly
    1640                1645                1650

Phe Gly Arg Val Val Cys Lys Val Pro Leu Gly Pro Asp Tyr Thr
1655                1660                1665

Ala Ile Ala Ile Ile Val Ala Thr Leu Ser Ile Leu Val Leu Met
    1670                1675                1680

Gly Gly Leu Ile Trp Phe Leu Phe Gln Arg His Arg Leu His Leu
1685                1690                1695

Ala Gly Phe Ser Ser Val Arg Tyr Ala Gln Gly Val Asn Glu Asp
    1700                1705                1710

Glu Ile Met Leu Pro Ser Phe His Asp
1715                1720

<210> SEQ ID NO 3
<211> LENGTH: 247
<212> TYPE: PRT
<213> ORGANISM: Homo sapiens

<400> SEQUENCE: 3

Met Glu Tyr His Pro Asp Leu Glu Asn Leu Asp Glu Asp Gly Tyr Thr
1               5                   10                  15

Gln Leu His Phe Asp Ser Gln Ser Asn Thr Arg Ile Ala Val Val Ser
                20                  25                  30

Glu Lys Gly Ser Cys Ala Ala Ser Pro Pro Trp Arg Leu Ile Ala Val
            35                  40                  45

Ile Leu Gly Ile Leu Cys Leu Val Ile Leu Val Ile Ala Val Val Leu
        50                  55                  60
```

```
Gly Thr Met Ala Ile Trp Arg Ser Asn Ser Gly Ser Asn Thr Leu Glu
 65                  70                  75                  80

Asn Gly Tyr Phe Leu Ser Arg Asn Lys Glu Asn His Ser Gln Pro Thr
                 85                  90                  95

Gln Ser Ser Leu Glu Asp Ser Val Thr Pro Thr Lys Ala Val Lys Thr
            100                 105                 110

Thr Gly Val Leu Ser Ser Pro Cys Pro Pro Asn Trp Ile Ile Tyr Glu
        115                 120                 125

Lys Ser Cys Tyr Leu Phe Ser Met Ser Leu Asn Ser Trp Asp Gly Ser
130                 135                 140

Lys Arg Gln Cys Trp Gln Leu Gly Ser Asn Leu Leu Lys Ile Asp Ser
145                 150                 155                 160

Ser Asn Glu Leu Gly Phe Ile Val Lys Gln Val Ser Ser Gln Pro Asp
                165                 170                 175

Asn Ser Phe Trp Ile Gly Leu Ser Arg Pro Gln Thr Glu Val Pro Trp
            180                 185                 190

Leu Trp Glu Asp Gly Ser Thr Phe Ser Ser Asn Leu Phe Gln Ile Arg
        195                 200                 205

Thr Thr Ala Thr Gln Glu Asn Pro Ser Pro Asn Cys Val Trp Ile His
    210                 215                 220

Val Ser Val Ile Tyr Asp Gln Leu Cys Ser Val Pro Ser Tyr Ser Ile
225                 230                 235                 240

Cys Glu Lys Lys Phe Ser Met
                245

<210> SEQ ID NO 4
<211> LENGTH: 209
<212> TYPE: PRT
<213> ORGANISM: Homo sapiens

<400> SEQUENCE: 4

Met Met Gln Glu Gln Gln Pro Gln Ser Thr Glu Lys Arg Gly Trp Leu
 1               5                  10                  15

Ser Leu Arg Leu Trp Ser Val Ala Gly Ile Ser Ile Ala Leu Leu Ser
                20                  25                  30

Ala Cys Phe Ile Val Ser Cys Val Val Thr Tyr His Phe Thr Tyr Gly
            35                  40                  45

Glu Thr Gly Lys Arg Leu Ser Glu Leu His Ser Tyr His Ser Ser Leu
        50                  55                  60

Thr Cys Phe Ser Glu Gly Thr Lys Val Pro Ala Trp Gly Cys Cys Pro
 65                  70                  75                  80

Ala Ser Trp Lys Ser Phe Gly Ser Ser Cys Tyr Phe Ile Ser Ser Glu
                 85                  90                  95

Glu Lys Val Trp Ser Lys Ser Glu Gln Asn Cys Val Glu Met Gly Ala
            100                 105                 110

His Leu Val Val Phe Asn Thr Glu Ala Glu Gln Asn Phe Ile Val Gln
        115                 120                 125

Gln Leu Asn Glu Ser Phe Ser Tyr Phe Leu Gly Leu Ser Asp Pro Gln
    130                 135                 140

Gly Asn Asn Asn Trp Gln Trp Ile Asp Lys Thr Pro Tyr Glu Lys Asn
145                 150                 155                 160

Val Arg Phe Trp His Leu Gly Glu Pro Asn His Ser Ala Glu Gln Cys
                165                 170                 175

Ala Ser Ile Val Phe Trp Lys Pro Thr Gly Trp Gly Trp Asn Asp Val
            180                 185                 190
```

```
Ile Cys Glu Thr Arg Arg Asn Ser Ile Cys Glu Met Asn Lys Ile Tyr
        195                 200                 205
Leu

<210> SEQ ID NO 5
<211> LENGTH: 328
<212> TYPE: PRT
<213> ORGANISM: Homo sapiens

<400> SEQUENCE: 5

Met Thr Val Glu Lys Glu Ala Pro Asp Ala His Phe Thr Val Asp Lys
1               5                   10                  15

Gln Asn Ile Ser Leu Trp Pro Arg Glu Pro Pro Lys Ser Gly Pro
            20                  25                  30

Ser Leu Val Pro Gly Lys Thr Pro Thr Val Arg Ala Ala Leu Ile Cys
        35                  40                  45

Leu Thr Leu Val Leu Val Ala Ser Val Leu Gln Ala Val Leu Tyr
    50                  55                  60

Pro Arg Phe Met Gly Thr Ile Ser Asp Val Lys Thr Asn Val Gln Leu
65                  70                  75                  80

Leu Lys Gly Arg Val Asp Asn Ile Ser Thr Leu Asp Ser Glu Ile Lys
                85                  90                  95

Lys Asn Ser Asp Gly Met Glu Ala Ala Gly Val Gln Ile Gln Met Val
            100                 105                 110

Asn Glu Ser Leu Gly Tyr Val Arg Ser Gln Phe Leu Lys Leu Lys Thr
        115                 120                 125

Ser Val Glu Lys Ala Asn Ala Gln Ile Gln Ile Leu Thr Arg Ser Trp
    130                 135                 140

Glu Glu Val Ser Thr Leu Asn Ala Gln Ile Pro Glu Leu Lys Ser Asp
145                 150                 155                 160

Leu Glu Lys Ala Ser Ala Leu Asn Thr Lys Ile Arg Ala Leu Gln Gly
                165                 170                 175

Ser Leu Glu Asn Met Ser Lys Leu Leu Lys Arg Gln Asn Asp Ile Leu
            180                 185                 190

Gln Val Val Ser Gln Gly Trp Lys Tyr Phe Lys Gly Asn Phe Tyr Tyr
        195                 200                 205

Phe Ser Leu Ile Pro Lys Thr Trp Tyr Ser Ala Glu Gln Phe Cys Val
    210                 215                 220

Ser Arg Asn Ser His Leu Thr Ser Val Thr Ser Glu Ser Glu Gln Glu
225                 230                 235                 240

Phe Leu Tyr Lys Thr Ala Gly Gly Leu Ile Tyr Trp Ile Gly Leu Thr
                245                 250                 255

Lys Ala Gly Met Glu Gly Asp Trp Ser Trp Val Asp Asp Thr Pro Phe
            260                 265                 270

Asn Lys Val Gln Ser Ala Arg Phe Trp Ile Pro Gly Glu Pro Asn Asn
        275                 280                 285

Ala Gly Asn Asn Glu His Cys Gly Asn Ile Lys Ala Pro Ser Leu Gln
    290                 295                 300

Ala Trp Asn Asp Ala Pro Cys Asp Lys Thr Phe Leu Phe Ile Cys Lys
305                 310                 315                 320

Arg Pro Tyr Val Pro Ser Glu Pro
                325

<210> SEQ ID NO 6
<211> LENGTH: 404
```

<212> TYPE: PRT
<213> ORGANISM: Homo sapiens

<400> SEQUENCE: 6

```
Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
        35                  40                  45

Ser Phe Thr Leu Leu Ala Gly Leu Leu Val Gln Val Ser Lys Val Pro
    50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
    130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
                165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
    210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
                245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
    290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys
        355                 360                 365

Cys Asn Leu Ala Lys Phe Trp Ile Cys Lys Lys Ser Ala Ala Ser Cys
    370                 375                 380

Ser Arg Asp Glu Glu Gln Phe Leu Ser Pro Ala Pro Ala Thr Pro Asn
385                 390                 395                 400
```

Pro Pro Pro Ala

<210> SEQ ID NO 7
<211> LENGTH: 213
<212> TYPE: PRT
<213> ORGANISM: Homo sapiens

<400> SEQUENCE: 7

Met Val Pro Glu Glu Pro Gln Asp Arg Glu Lys Gly Leu Trp Trp
1               5                   10                  15

Phe Gln Leu Lys Val Trp Ser Met Ala Val Val Ser Ile Leu Leu Leu
                20                  25                  30

Ser Val Cys Phe Thr Val Ser Ser Val Val Pro His Asn Phe Met Tyr
            35                  40                  45

Ser Lys Thr Val Lys Arg Leu Ser Lys Leu Arg Glu Tyr Gln Gln Tyr
50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                85                  90                  95

Ile Ser Thr Gly Met Gln Ser Trp Thr Lys Ser Gln Lys Asn Cys Ser
                100                 105                 110

Val Met Gly Ala Asp Leu Val Val Ile Asn Thr Arg Glu Glu Gln Asp
            115                 120                 125

Phe Ile Ile Gln Asn Leu Lys Arg Asn Ser Ser Tyr Phe Leu Gly Leu
    130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
            180                 185                 190

Trp Asn Asp Ile His Cys His Val Pro Gln Lys Ser Ile Cys Lys Met
        195                 200                 205

Lys Lys Ile Tyr Ile
    210

<210> SEQ ID NO 8
<211> LENGTH: 237
<212> TYPE: PRT
<213> ORGANISM: Homo sapiens

<400> SEQUENCE: 8

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
                20                  25                  30

Thr Ala Pro His Lys Ser Asn Thr Gly Phe Pro Lys Leu Leu Cys Ala
            35                  40                  45

Ser Leu Leu Ile Phe Phe Leu Leu Leu Ala Ile Ser Phe Phe Ile Ala
        50                  55                  60

Phe Val Ile Phe Phe Gln Lys Tyr Ser Gln Leu Leu Glu Lys Lys Thr
65                  70                  75                  80

Thr Lys Glu Leu Val His Thr Thr Leu Glu Cys Val Lys Lys Asn Met
                85                  90                  95

Pro Val Glu Glu Thr Ala Trp Ser Cys Cys Pro Lys Asn Trp Lys Ser
            100                 105                 110

```
Phe Ser Ser Asn Cys Tyr Phe Ile Ser Thr Glu Ser Ala Ser Trp Gln
            115                 120                 125

Asp Ser Glu Lys Asp Cys Ala Arg Met Glu Ala His Leu Leu Val Ile
130                 135                 140

Asn Thr Gln Glu Glu Gln Asp Phe Ile Phe Gln Asn Leu Gln Glu Glu
145                 150                 155                 160

Ser Ala Tyr Phe Val Gly Leu Ser Asp Pro Glu Gly Gln Arg His Trp
                165                 170                 175

Gln Trp Val Asp Gln Thr Pro Tyr Asn Glu Ser Ser Thr Phe Trp His
            180                 185                 190

Pro Arg Glu Pro Ser Asp Pro Asn Glu Arg Cys Val Val Leu Asn Phe
        195                 200                 205

Arg Lys Ser Pro Lys Arg Trp Gly Trp Asn Asp Val Asn Cys Leu Gly
    210                 215                 220

Pro Gln Arg Ser Val Cys Glu Met Met Lys Ile His Leu
225                 230                 235

<210> SEQ ID NO 9
<211> LENGTH: 291
<212> TYPE: PRT
<213> ORGANISM: Homo sapiens

<400> SEQUENCE: 9

Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Leu Ser Leu Gly Leu
        35                  40                  45

Ser Leu Leu Leu Leu Val Val Val Cys Val Ile Gly Ser Gln Asn Ser
    50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu Leu His Val Lys
        115                 120                 125

Gln Phe Val Ser Asp Leu Arg Ser Leu Ser Cys Gln Met Ala Ala Leu
    130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
            180                 185                 190

Thr Ser Trp Glu Glu Gln Lys Phe Val Gln His Ile Gly Pro Val
        195                 200                 205

Asn Thr Trp Met Gly Leu His Asp Gln Asn Gly Pro Trp Lys Trp Val
    210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Gly Glu Asp Cys Ala
                245                 250                 255
```

His Phe Thr Asp Asp Gly Arg Trp Asn Asp Asp Val Cys Gln Arg Pro
            260                 265                 270

Tyr Arg Trp Val Cys Glu Thr Glu Leu Asp Lys Ala Ser Gln Glu Pro
            275                 280                 285

Pro Leu Leu
    290

<210> SEQ ID NO 10
<211> LENGTH: 31
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Leu, Ile, Val, Met, Phe, Tyr, Ala, Thr or Gly
<220> FEATURE:
<221> NAME/KEY: MOD_RES
<222> LOCATION: (3)..(14)
<223> OTHER INFORMATION: Any amino acid
<220> FEATURE:
<221> NAME/KEY: misc_feature
<222> LOCATION: (3)..(14)
<223> OTHER INFORMATION: This region may encompass 5-12 residues
<220> FEATURE:
<221> NAME/KEY: MOD_RES
<222> LOCATION: (15)..(15)
<223> OTHER INFORMATION: Trp or Leu
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Asp, Asn, Ser or Arg
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(28)
<223> OTHER INFORMATION: Any amino acid
<220> FEATURE:
<221> NAME/KEY: misc_feature
<222> LOCATION: (21)..(28)
<223> OTHER INFORMATION: This region may encompass 5-8 residues
<220> FEATURE:
<221> NAME/KEY: MOD_RES
<222> LOCATION: (29)..(29)
<223> OTHER INFORMATION: Phe, Tyr, Trp, Leu, Ile, Val, Ser, Thr or Ala
<220> FEATURE:
<221> NAME/KEY: MOD_RES
<222> LOCATION: (30)..(30)
<223> OTHER INFORMATION: Leu, Ile, Val, Met, Ser, Thr or Ala

<400> SEQUENCE: 10

Cys Xaa Xaa Xaa Xaa Xaa Xaa Xaa Xaa Xaa Xaa Xaa Xaa Xaa Xaa Xaa
1               5                   10                  15

Xaa Xaa Xaa Cys Xaa Xaa Xaa Xaa Xaa Xaa Xaa Xaa Xaa Xaa Cys
            20                  25                  30

<210> SEQ ID NO 11
<211> LENGTH: 45
<212> TYPE: PRT
<213> ORGANISM: Rattus sp.

<400> SEQUENCE: 11

Glu Asn Trp Gly Ala Gly Glu Pro Asn Asn Lys Lys Ser Lys Glu Asp

```
                1               5                  10                 15
Cys Val Glu Ile Tyr Ile Lys Arg Glu Arg Asp Ser Gly Lys Trp Asn
                    20                 25                 30

Asp Asp Ala Cys His Lys Arg Lys Ala Ala Leu Cys Tyr
            35                 40                 45

<210> SEQ ID NO 12
<211> LENGTH: 40
<212> TYPE: PRT
<213> ORGANISM: Mus sp.

<400> SEQUENCE: 12

Thr Asn Trp Asn Glu Gly Glu Pro Asn Asn Val Gly Ser Gly Glu Asn
1               5                   10                  15

Cys Val Val Leu Leu Thr Asn Gly Lys Trp Asn Asp Val Pro Cys Ser
                20                  25                  30

Asp Ser Phe Leu Val Val Cys Glu
            35                  40

<210> SEQ ID NO 13
<211> LENGTH: 238
<212> TYPE: PRT
<213> ORGANISM: Mus musculus

<400> SEQUENCE: 13

Met Ser Asp Ser Lys Glu Met Gly Lys Arg Gln Leu Arg Pro Leu Asp
1               5                   10                  15

Glu Glu Leu Leu Thr Ser Ser His Thr Arg His Ser Ile Lys Gly Phe
                20                  25                  30

Gly Phe Gln Thr Asn Ser Gly Phe Ser Ser Phe Thr Gly Cys Leu Val
            35                  40                  45

His Ser Gln Val Pro Leu Ala Leu Gln Val Leu Phe Leu Ala Val Cys
        50                  55                  60

Ser Val Leu Leu Val Val Ile Leu Val Lys Val Tyr Lys Ile Pro Ser
65                  70                  75                  80

Ser Gln Glu Glu Asn Asn Gln Met Asn Val Tyr Gln Glu Leu Thr Gln
                85                  90                  95

Leu Lys Ala Gly Val Asp Arg Leu Cys Arg Ser Cys Pro Trp Asp Trp
            100                 105                 110

Thr His Phe Gln Gly Ser Cys Tyr Phe Phe Ser Val Ala Gln Lys Ser
        115                 120                 125

Trp Asn Asp Ser Ala Thr Ala Cys His Asn Val Gly Ala Gln Leu Val
    130                 135                 140

Val Ile Lys Ser Asp Glu Glu Gln Asn Phe Leu Gln Gln Thr Ser Lys
145                 150                 155                 160

Lys Arg Gly Tyr Thr Trp Met Gly Leu Ile Asp Met Ser Lys Glu Ser
                165                 170                 175

Thr Trp Tyr Trp Val Asp Gly Ser Pro Leu Thr Leu Ser Phe Met Lys
            180                 185                 190

Tyr Trp Ser Lys Gly Glu Pro Asn Asn Leu Gly Glu Glu Asp Cys Ala
        195                 200                 205

Glu Phe Arg Asp Asp Gly Trp Asn Asp Thr Lys Cys Thr Asn Lys Lys
    210                 215                 220

Phe Trp Ile Cys Lys Lys Leu Ser Thr Ser Cys Pro Ser Lys
225                 230                 235

<210> SEQ ID NO 14
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ile Ile Asn Phe Glu Lys Leu
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ile Ser Gln Ala Val His Ala Ala His Ala Glu Ile Asn Glu Ala
1               5                   10                  15

Gly
```

ANTIGEN-CARBOHYDRATE CONJUGATES

REFERENCE TO RELATED APPLICATIONS

This application is the U.S. national stage of PCT/US2005/025461, filed on Jul. 18, 2005, which claims the benefit of U.S. Provisional Application No. 60/588,671, filed on Jul. 16, 2004, each of which is hereby incorporated by reference in its entirety.

Each of the applications and patents cited in this text, as well as each document or reference cited in each of the applications and patents (including during the prosecution of each issued patent; "application cited documents"), and each of the PCT and foreign applications or patents corresponding to and/or claiming priority from amy of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

FEDERALLY SPONSORED RESEARCH

Various aspects of the present invention were sponsored by the National Institutes of Health (grant nos. RO1 HL62598-01A1 and R21AIO63081-01). The Government has certain rights.

SEQUENCE LISTING

This application contains a Sequence Listing which has been submitted via EFS-Web and is hereby incorporated by reference in its entirety. Said ASCII copy, created on Aug. 16, 2010, is named 63677515.txt, and is 49,586 bytes in size.

FIELD OF INVENTION

The present invention generally relates to antigen presentation and/or immune modulation using antigen-carbohydrate conjugates and, in particular, to antigen presentation and/or immune modulation using antigen-carbohydrate conjugates able to bind lectins on dendritic cells or other antigen presenting cells.

BACKGROUND

Dendritic cells ("DC") are one type of antigen-presenting cell ("APC") of the immune system. Dendritic cells typically ingest antigens by phagocytosis, pinocytosis, or via interaction with a variety of cell surface receptors and endocytosis; degrade the antigens; then present fragments of those antigens in association with MI-IC ("major histocompatibility complex") on their surfaces that other immune cells (primarily T cells) respond to. Dendritic cells can be characterized by long "dendritic" processes (resembling dendrites in nerve cells). These cells are typically found in nonlymphoid organs, for example, the skin (where they are called Langerhans cells), nose, heart, liver, kidneys, lungs, stomach, intestines, etc., where they are able to capture antigens. It is believed that, upon capturing antigens, dendritic cells migrate through the circulation (blood and lymph) to the lymphoid organs where they can interact with T cells to induce their proliferation, activation to effectors, activation to memory, deletion (death), anergy (inactivation) or regulatory functions (e.g., Tr1, Tr2).

Lectins are glycoproteins that can bind carbohydrates. Molecular analysis of dendritic cells has revealed that they express a variety of these carbohydrate-specific proteins. It has been demonstrated that the lectins function in dendritic cells to capture and direct antigens to specialized antigen-processing compartments within the cell, via receptor-mediated endocytosis. Furthermore, there is evidence to suggest that lectin-ligand interactions can modulate cytokine production by dendritic cells as well as the maturation state of those cells. One class of lectins that often appear on dendritic cells are calcium-dependent carbohydrate binding proteins, or "C-type lectins." Specific lectins may be expressed on each type of dendritic cell, such as the lectin Langerin on Langerhan dendritic cells, the lectin BDCA-2 on plasmacythid dendritic cells, or the lectin DC-SIGN on myeloid dendritic cells.

SUMMARY OF THE INVENTION

The present invention relates to antigen presentation and/or immune modulation using antigen-carbohydrate conjugates able to bind lectins on dendritic cells or other antigen presenting cells. The subject matter of the present invention involves, in some cases, interrelated products, alternative solutions to a particular problem, and/or a plurality of different uses of one or more systems and/or articles.

In one aspect, the invention generally comprises a composition containing at least one carbohydrate conjugated to a molecule, where the composition is capable of binding to a protein present on a cell. In one embodiment, the molecule is a protein, glycoprotein, a lipid, chemically modified lipid, or glycolipid, a polysaccharide, a small molecule.

In a related aspect, the invention provides a composition containing at least one carbohydrate conjugated to an antigen, where the composition is capable of binding to a protein present on an antigen-presenting cell.

In another related aspect, the invention provides a composition containing an antigen-carbohydrate conjugate able to bind a lectin that is expressed on antigen-presenting cells, the conjugate containing mannose.

In yet another aspect, the invention provides an immunogenic composition containing at least one carbohydrate conjugated to an antigen in a pharmaceutically acceptable excipient, where the composition is capable of modulating an immune response.

In yet another aspect, the invention provides a composition, containing: an antigen-carbohydrate conjugate able to bind a lectin that is expressed on antigen-presenting cells but is not substantially expressed on non-antigen-presenting cells.

In yet another aspect, the invention provides a method of immunization. The method involves administering, to a subject (e.g., mammal or human), a composition containing a conjugate of an antigen and a carbohydrate able to bind a lectin that is expressed on antigen-presenting cells but is not substantially expressed on non-antigen-presenting cells, in an amount effective to immunize the subject to the antigen.

In yet another aspect, the invention provides a method of inducing immunological tolerance, involving administering to a subject, a composition containing a conjugate of an antigen and a carbohydrate able to bind a lectin that is expressed on antigen-presenting cells but is not substantially expressed on non-antigen-presenting cells, in an amount effective to induce immunological tolerance of the subject to the antigen.

In yet another aspect, the invention provides a method that involves administering, to an antigen presenting cell an antigen-carbohydrate conjugate able to bind a lectin that is expressed on the antigen-presenting cell but that is not substantially expressed on non-antigen-presenting cells.

In yet another aspect, the invention provides a method of modulating an immune response in a cell; the method involves contacting a cell of a subject with a composition of any one of the previous aspects, where the contacting modulates an immune response.

In yet another aspect, the invention provides a method of reducing, stabilizing, or ameliorating the symptoms of an allergic response in a subject in need thereof. The method involves contacting a cell of the subject with a composition of any previous aspect, where the contacting reduces, stabilizes, or ameliorates an allergic response. In one embodiment, the method ameliorates a disease or disorder selected from the group consisting of eczema, allergic rhinitis, coryza, hay fever, conjunctivitis, bronchial asthma, allergic asthma, urticaria, atopic dermatitis, anaphylaxis, food allergy, drug allergy, and angioedema.

In another aspect, the invention provides a method of reducing, stabilizing, or ameliorating the symptoms of an autoimmune response in a subject in need thereof, the method involves contacting a cell of the subject with a composition of any previous aspect, where the contacting reduces, stabilizes, or ameliorates an autoimmune response. In one embodiment, the method treats a disease or disorder selected from the group consisting of Addison's disease, autoimmune anemia, Goodpasture's syndrome, Graves' disease, Hashimoto's thyroiditis, idiopathic thrombocytopenia purpura, type I diabetes, myasthenia gravis, ankylosing spondylitis, multiple sclerosis, rheumatoid arthritis, psoriasis, Crohn's disease, scleroderma, Sjögren's syndrome, and systemic lupus erythematosus.

In yet another aspect, the invention provides a method of reducing, stabilizing, or ameliorating a pathogen infection in a subject in need thereof, the method involves contacting a cell of the subject with a composition of any previous aspect, where the contacting reduces, stabilizes, or ameliorates a pathogen infection. In one embodiment, the pathogen infection is a bacterial infection, a viral infection, or a fungal infection. In one embodiment, the bacteria is selected from the group consisting of *Helicobacter pyloris, Borelia burgdorferi, Legionella pneumophilia, Mycobacteria* sps (e.g., *M. tuberculosis, M. avium, M. intracellulare, M. kansaii, M. gordonae*, etc.), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*. In one embodiment, the method the virus is selected from the group consisting of Retroviridae, human immunodeficiency viruses, Picornaviridae, Calciviridae, Togaviridae, Flaviridae, Coronoviridae, Rhabdoviradae, Coronaviridae, Rhabdoviridae, Filoviridae, Paramyxoviridae, Orthomyxoviridae, Bungaviridae, Arena viridae, Reoviridae, Birnaviridae, Hepadnaviridae, Parvovirida, Papovaviridae, Adenoviridae (adenoviruses), Herpesviridae, Poxyiridae, and Iridoviridae. In another embodiment, the fungus is selected from the group consisting of *Cryptococcus neoformans, Histoplasma capsulatum, Coccidioides immitis, Blastomyces dermatitidis, Chlamydia trachomatis*, and *Candida albicans*.

In yet another aspect, the invention provides method of treating a neoplasm in a subject, the method involves contacting a cell of the subject in need thereof with a composition of any previous aspect, where the contacting reduces, stabilizes, or ameliorates the symptoms of a neoplasm. In one embodiment, the neoplasm is selected from the group consisting of acute lymphoblastic leukemia, glioma, bladder cancer, billiary cancer, breast cancer, cervical carcinoma, colon carcinoma, colorectal cancer, choriocarcinoma, epithelial cell-cancer, gastric cancer, hepatocellular cancer, Hodgkins lymphoma, lung cancer, lymphoid cell-derived leukemia, myeloma, non-small cell lung carcinoma, nasopharyngeal cancer, ovarian cancer cancer, prostate cancer, pancreatic cancer, renal cancer, testicular cancer, T cell leukemia, and melanoma.

In yet another aspect, the invention provides method of enhancing antigen presentation by a cell, the method involves contacting an antigen-presenting cell with at least one oligosaccharide conjugated to an antigen or antigen mimetic, where the contacting enhances antigen presentation by the antigen-presenting cell.

In yet another aspect, the invention provides method of increasing T cell proliferation in a subject, the method involves contacting an antigen-presenting cell with at least one oligosaccharide conjugated to an antigen or antigen mimetic, where the contacting enhances antigen presentation by the antigen-presenting cell.

In another aspect, kit for modulating an immune response, the kit contains the composition of any previous aspect. In one embodiment, the kit further contains directions for administering the composition to the subject.

In yet another aspect, the invention provides a method of generating an antigen carbohydrate conjugate. The method involves conjugating an antigen to a carbohydrate able to bind a lectin that is expressed on antigen-presenting cells but is not substantially expressed on non-antigen-presenting cells.

In yet another aspect, the invention provides a method that involves providing a lectin that is expressed on antigen-presenting cells but is not substantially expressed on non-antigen-presenting cells screening a carbohydrate library to identify carbohydrates able to bind the lectin; and conjugating an antigen to one of the identified carbohydrates able to bind the lectin.

In yet another aspect, the invention provides a method of immunization. The method involves administering, to a subject, a composition containing a conjugate of an antigen and a carbohydrate, containing mannose, that is able to bind a lectin that is expressed on antigen-presenting cells, in an amount effective to immunize the subject to the antigen.

In yet another aspect, the invention provides a method of inducing immunological tolerance. The method involves administering, to a subject, a composition containing a conjugate of an antigen and a carbohydrate, containing mannose, that is able to bind a lectin that is expressed on antigen-presenting cells, in an amount effective to induce immunological tolerance of the subject to the antigen.

In yet another aspect, the invention features a method involving administering, to an antigen-presenting cell, an antigen-carbohydrate conjugate able to bind a lectin that is expressed on the antigen-presenting cell, the conjugate containing mannose.

In yet another aspect, the invention features a method, involving conjugating an antigen to a carbohydrate able to bind a lectin that is expressed on antigen presenting cells, the carbohydrate containing mannose.

In yet another aspect, the invention features a method that involves providing a lectin that is expressed on antigen-presenting cells, but that is not substantially expressed on non-antigen-presenting cells; screening a carbohydrate library to identify carbohydrates able to bind the lectin; and conjugating an antigen to one of the identified carbohydrates able to bind the lectin.

In various embodiments of any of the above aspects, the antigen is a protein, glycoprotein, a lipid, chemically modified lipid, glycolipid, a polysaccharide, or a small molecule (e.g., a molecule having a molecular weight between 100 and 2,000 daltons, where the lower limit of the range is any integer between 100 and 1,999; and the upper limit of the range is any integer between 101 and 2000. In other embodiments of any of the above aspects, the protein present on the cell is a carbohydrate binding protein (e.g., a lectin, such as an I-type, S-type, P-type, or C-type lectin).

In other embodiments of any of the above aspects, the cell is an antigen-presenting cell, such as a dendritic cell. In yet other embodiments of any of the above aspects, the carbohydrate is selected from the group consisting of monosaccharides, oligosaccharides (e.g., a branched oligosaccharide or a linear oligosaccharide), and polysaccharides. In various embodiments of the above aspects, the composition comprises at least two, three, four, or five oligosaccharides, where at least one, two, three, four, or five of the oligosaccharides are different and the addition of the carbohydrate increases the molecular weight of the antigen between 25 and 1000 daltons (e.g., 50, 100, 200, 300, 400, 500, 600, 750 daltons) or between 2, 5, 10, 15, and 45 kDa, where the lower end of the range is any integer between 25 daltons and 44 kDa, and the upper end of the range is any integer between 26 daltons and 45 kDa.

In various embodiments of any of the above aspects, the carbohydrate is selected from the group consisting of structures 3-1 to 3-7 (FIG. 1). In other embodiments, the carbohydrate is a mannose oligosaccharide (e.g., $(Man)_9(GlcNAc)_2$), or an analog thereof.

In other embodiments of any of the above aspects, the carbohydrate is conjugated to the antigen via a linker (e.g., a thiol-bearing linker), such as a linker that has the following structure:

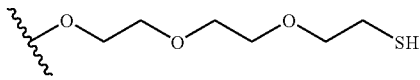

In other embodiments of any of the above aspects, the antigen is an autoimmune antigen (e.g., a glutamate decarboxylase, insulin-B, myelin basic protein, or acetylcholine receptor alpha subunit), and the composition containing the antigen is useful for the treatment of any one or more of the following Addison's disease, autoimmune anemia, Goodpasture's syndrome, Graves' disease, Hashimoto's thyroiditis, idiopathic thrombocytopenia purpura, type I diabetes, myasthenia gravis, ankylosing spondylitis, multiple sclerosis, rheumatoid arthritis, psoriasis, Crohn's disease, scleroderma, Sjögren's syndrome, and systemic lupus erythematosus.

In other embodiments of any of the above aspects, the antigen is a tumor antigen (e.g., alpha-fetoprotein, Ig-idiotype, mutant cyclin-dependent kinase 4, Pmel-17, MART-1, p15 protein, tyrosinase, MAGE 1, 2 and 3, a Gage family member, BAGE, human papilloma virus antigens E6 and E7, an Epstein-ban virus antigen, bcr-abl fusion product, gp75, oncofetal antigen, mucin, telomerase, GM2 ganglioside, GD2 ganglioside, mutant p53, mutant cdk4, p21ras, HER21neu, c-erbB-2, colorectal associated antigen (CRC)-0017-1A/GA733, APC, cyclophilin b, ga733 glycoprotein, Imp-1, EBNA-1, prostate specific antigen, pancreatic tissue antigen, prostate specific membrane antigen, thyroglobulin, carcinoembryonic antigen, NY-ESO-1, HTLV-1, cdc27, and gp100$_{Pmel117}$) useful for the treatment of any one or more of the following cancers: acute lymphoblastic leukemia, B cell non-Hodgkin's lymphoma, multiple myeloma, glioma, bladder cancer, billiary cancer, breast cancer, Burkitt's lymphoma, cervical carcinoma, chronic myelogenous leukemia, colon carcinoma, colorectal cancer, choriocarcinoma, epithelial cell-cancer, gastric cancer, hepatocellular cancer, Hodgkins lymphoma, liver cancer, lung cancer, lymphoid cell-derived leukemia, myeloma, non-small cell lung carcinoma, nasopharyngeal cancer, ovarian cancer cancer, prostate cancer, pancreatic cancer, renal cancer, testicular cancer, thyroid cancer, T cell leukemia, and melanoma.

In other embodiments of any of the above aspects, the antigen is derived from airborne particulates, plant pollen, mites, molds, spores, animal hair, dander, shellfish, nuts, fruits, insects, insect venoms, penicillins, sulfonamides, eggs, peas, and beans.

In other embodiments of any of the above aspects, the antigen is a pathogen antigen derived from a bacteria (e.g., *Helicobacter pyloris, Borelia burgdorferi, Legionella Mycobacteria* sps (e.g., *M. tuberculosis, M. avium, M. intracellulare, M. kansaii, M. gordonae,* etc.), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae,* pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelii*), In other embodiments of any of the above aspects, the antigen is a pathogen antigen derived from a virus (e.g., Retroviridae, human immunodeficiency viruses, Picornaviridae, Calciviridae, Togaviridae, Flaviridae, Coronoviridae, Rhabdoviradae, Coronaviridae, Rhabdoviridae, Filoviridae, Paramyxoviridae, Orthomyxoviridae, Bungaviridae, Arena viridae, Reoviridae, Birnaviridae, Hepadnaviridae, Parvovirida, Papovaviridae, Adenoviridae (adenoviruses), Herpesviridae, Poxyiridae, and Iridoviridae), or fungus (e.g., *Cryptococcus neoformans, Histoplasma capsulatum, Coccidioides immitis, Blastomyces dermatitidis, Chlamydia trachomatis,* and *Candida albicans*). Exemplary antigens include human immunodeficiency virus gp120 protein, malarial Merozoite Surface Protein-1, Apical membrane protein-1, *Plasmodium falciparum* erythrocyte membrane protein, tuberculosis antigen 85 A/B, ESAT-6, tuberculosis heat shock protein 60, influenza hemaglutinin, influenza neuraminidase, hepatitis B virus antigen.

In various embodiments, the antigen is derived from a non-human source, a non-living source, a biological species that the subject is not a member of. In other embodiments, the composition comprises a pool of suspected antigens isolated from a source, a pool of suspected antigens that is artificially generated.

In other embodiments of any of the above aspects, the carbohydrate comprises a plurality of mannose residues. In other embodiments of any of the above aspects, the lectin is an I-type, S-type, P-type, or C-type lectin (e.g., DC-SIGN, a type I, or type II C-type lectin) or the lectin comprises SEQ ID NO: 10. In other embodiments of any of the above aspects, the lectin is expressed on a dendritic cell (e.g., a human cell in vivo or ex vivo).

In other embodiments of the above aspects, the antigen is pre-selected or arises from a pool of suspected antigens. In yet other embodiments, the carbohydrate-antigen conjugate is capable of enhancing or reducing by at least 5%, 10%, 25%, 50%, 75%, 80%, 85%, 90%, or 95% relative to a reference immune response occurring in the absence of the conjugate. In other embodiments of the above aspects, the carbohydrate comprises a hexose, fucose, galactose, a lectin ligand (e.g., at least 2, 3, 4, or 5 mannose residues), a plurality of mannose residues, where the lectin (e.g., Dectin 1, Dectin 2, BDCA-2, CLEC-1, or SEQ ID NO: 10) is expressed on dendritic cells (e.g., human).

In yet other embodiments, the composition comprises more than one conjugate type. In yet other embodiments, the antigen-carbohydrate conjugate is bound to a hapten. In other embodiments of any of the above aspects, the composition further contains a pharmaceutically acceptable carrier, an adjuvant, or a cytokine.

In various embodiments of the above methods, the method further comprises administering a cytokine or an adjuvant to the subject. In various other embodiments, the amount is effective to promote dendritic cell maturation. In other embodiments, the composition is effective to inhibit dendritic cell maturation, to induce T cell anergy, to induce T cell deletion, to induce T cell regulatory activity. In various embodiments of any of the above aspects, the subject is a mammal, such as a human. In yet other embodiments, the cell (e.g., a human cell ex vivo or in vivo) of any of the above aspects functions in an adaptive immune response (e.g., the cell is an antigen-presenting cell, or is a dendritic cell).

In another aspect, the invention is a method. In one set of embodiments, the method includes an act of exposing an antigen-presenting cell, such as a dendritic cell, to a composition comprising an antigen-carbohydrate conjugate able to bind a lectin expressable on the antigen-presenting cell. The act of exposing may occur ex vivo, in vitro, or in vivo. The method, according to another set of embodiments, includes an act of administering, to a subject such as a human, a composition comprising an antigen-carbohydrate conjugate able to bind a lectin that is expressed on antigen-presenting cells, such as dendritic cells. In one embodiment, the lectin is not substantially expressed on non-antigen-presenting cells. In another embodiment, the carbohydrate includes mannose.

In another set of embodiments, the method is a method of immunization. In one embodiment, the method includes an act of administering, to a subject, a composition comprising a conjugate of an antigen and a carbohydrate able to bind a lectin that is expressed on antigen-presenting cells, in an amount effective to immunize the subject to the antigen. In one embodiment, the lectin is not substantially expressed on non-antigen-presenting cells. In another embodiment, the carbohydrate includes mannose.

In another set of embodiments, the method is a method of inducing immunological tolerance. In one embodiment, the method includes an act of administering, to a subject, a composition comprising a conjugate of an antigen and a carbohydrate able to bind a lectin that is expressed on antigen-presenting cells, in an amount effective to induce immunological tolerance of the subject to the antigen. In one embodiment, the lectin is not substantially expressed on non-antigen-presenting cells. In another embodiment, the carbohydrate includes mannose.

In yet another set of embodiments, the method comprises an act of administering, to an antigen-presenting cell, an antigen-carbohydrate conjugate able to bind a lectin that is expressed on the antigen-presenting cell. In one embodiment, the lectin is not substantially expressed on non-antigen-presenting cells. In another embodiment, the carbohydrate includes mannose.

In one set of embodiments, the method comprises an act of conjugating an antigen to a carbohydrate able to bind a lectin that is expressed on antigen-presenting cells. In one embodiment, the lectin is not substantially expressed on non-antigen-presenting cells. In another embodiment, the carbohydrate includes mannose.

Yet another set of embodiments provides a method comprising acts of providing a lectin that is expressed on antigen-presenting cells but is not substantially expressed on non-antigen-presenting cells, and screening a carbohydrate library to identify carbohydrates able to bind the lectin. In certain instances, the method also includes conjugating an antigen to one of the identified carbohydrates able to bind the lectin. In one embodiment, the lectin is not substantially expressed on non-antigen-presenting cells. In another embodiment, the carbohydrate includes mannose.

Another aspect of the invention provides a composition comprising an antigen-carbohydrate conjugate able to bind a lectin that is expressed on antigen-presenting cells. In one embodiment, the lectin is not substantially expressed on non-antigen-presenting cells. In another embodiment, the carbohydrate includes a hexose, such as mannose, fucose, galactose, etc. In certain cases, the carbohydrate includes multiple saccharide residues, for example, 2, 3, 4, 5, etc. residues.

In some cases, the lectin may be expressed on dendritic cells, ex vivo, in vitro, or in vivo. The lectin may be, for example, a Type I or a Type II C-type lectin. Non-limiting examples of lectins include DC-SIGN, Dectin 1, Dectin 2, BCDA-2, CLEC-1, etc. In certain instances, the subject may be a mammal, such as a human.

The antigen, in some cases, may comprise a protein, for example, ovalbumin or BSA. The antigen may arise from a pool of suspected antigens (which may be isolated from a source, artificially generated, etc.), and/or the antigen may be pre-selected in some cases. The antigen may be derived from the subject, from another member of the biological species that the subject is a member of, or from a biological species that the subject is not a member of. For example, the antigen may be derived from a non-human and/or a non-living source.

In some cases, the composition may also include other entities as well, for example, adjuvants, cytokines, haptens, other conjugates, pharmaceutically acceptable carriers, or the like.

In another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention.

FIG. 2A shows a Western blot of OVA, SMCC-activated OVA and carbohydrate modified OVA that were resolved by SDS-PAGE electrophoresis and immunoblotted with an anti-OVA polyclonal antibody to reveal changes in molecular weight as a function of carbohydrate addition. FIG. 2B is a graph showing that oligosaccharide modification of OVA elicits stronger presentation to OTII T cells than unmodified OVA. Unfractionated OTII splenocytes ($3\times10^5$/well) were incubated with graded doses of OVA or oligosaccharide-modified OVA for eighty-four hours with [$^3$H]thymidine (1 µCi) added for the last 12 hours. Thereafter [$^3$H]thymidine incorporation levels were measured and plotted. FIG. 2C is a graph showing that observed enhancements in antigen presentation of (OVA)-3-1 to T cells is carbohydrate dependent. Splenocytes were incubated with antigen as in (B)±(BSA)-3-1 (10 µg mL$^{-1}$). In cases where (OVA)-3-1 was added to OVA wells to assess the possibility of direct activation of T cells (see text), (OVA)-3-1 was present at 50 ng mL$^{-1}$; incubations were performed for seventy-two hours with [$^3$H]thymidine (1 µCi) added for the last 12 hours. FIG. 2D is a graph showing that the receptor mediated uptake of (OVA)-3-1 has a different binding profile than that observed for DC-SIGN. Unfractionated splenocytes were incubated with OVA or (OVA)-3-1±mBSA or Lewis$^x$-BSA (each at 100 µg mL$^{-1}$). Incubations were performed for seventy-two hours with [$^3$H]thymidine (1 µCi) added for the last twelve hours. All values reported are the mean of triplicate measurements.

FIGS. 3A and 3B are graphs showing that nonasaccharide 3-1-promoted presentation via MHC class I pathway for presentation to CD8$^+$ T cells. FIG. 3A shows that (OVA)-3-1 enhanced presentation of antigenic peptides to CD8$^+$ T cells in a dose- and carbohydrate-dependent fashion. Unfractionated OTI splenocytes ($3\times10^5$/well) were incubated with graded doses of OVA±(OVA)-3-1 (50 ng mL$^{-1}$) or (OVA)-3-1±(BSA)-3-1 (10 µg mL$^{-1}$). Incubations were performed for seventy-two hours with [$^3$H]thymidine (1 µCi) added for the last twelve hours. FIG. 3B is a graph showing that the monosaccharide mannose 3-6 targets a different receptor than 3-1. OTII splenocytes were incubated with graded doses of monosaccharide-modified OVA±(BSA)-3-1 and T cell proliferation was measured as described for FIG. 3A. Values present the mean of triplicate measurements.

FIG. 4A shows that purified CD11c$^+$ dendritic cells efficiently present (OVA)-3-1 to purified CD4$^+$ T cells. $1.5\times10^4$ Splenic CD11c$^+$ dendritic cells purified from C57BL/6 mice and $3.0\times10^4$ purified OTII T cells were incubated with OVA (starting concentration 300 µg mL$^{-1}$) or (OVA)-3-1 (starting concentration 25 µg mL$^{-1}$) in graded doses for eight-four hours with [$^3$H]thymidine (1 µCi) added for the last twelve hours. FIG. 4B shows that the receptor mediating uptake of (OVA)-3-1 preferentially binds complex mannans. Purified CD11c$^+$ dendritic cells and OTII T cells were incubated with (OVA)-3-1 (25 µg mL$^{-1}$)±each potential inhibitor (100 µg mL$^{-1}$). T cell proliferation was determined as for FIG. 4A. FIG. 4C shows that Toll-like receptor-induced dendritic cell maturation significantly decreased uptake and presentation of (OVA)-3-1 to T cells. CD11c$^+$ dendritic cells and OTII T cells were incubated with OVA or (OVA)-3-1±lipopolysaccharide (1 µmL$^{-1}$). Also included are all 'non-dendritic cells' (macrophages and B cells) obtained during the purification of the dendritic cells. T cell proliferation was determined as described in FIG. 4A. FIG. 4D shows that targeting (OVA)-3-1 to dendritic cells leads to a more vigorous T cell response in a highly pro-inflammatory situation. Supernatants from cells described in FIG. 4C were collected at forty-eight and seventy-two hours and measured for IFN-γ by ELISA; the values presented are from the seventy-two hour time point. All measurements here were performed in triplicate.

FIGS. 6A, 6B, and 6C are a schematic diagram (FIG. 6A) and a series of flow cytometry dot plots (FIGS. 6B and 6C). FIG. 6A is a schematic diagram that illustrates the adoptive transfer technique: CD4$^+$CD45.2$^+$ ovalbumin-specific T cells are adoptively transferred to congenic CD45.1$^+$ recipients. After immunization the draining lymph nodes and other lymphoid organs (e.g., the spleen) are isolated. Cells from these tissues are stained with an antibody against the CD45.2 isoform and the OTII T cell receptor to identify the original donor cells. FIG. 2B immunization with (OVA)-3-1 promotes expansion of OVA-specific T cells. B6.Ly5.2/Cr mice were injected intravenously with $2\times10^7$ OTII splenocytes. 24 hours later the mice were injected subcutaneously with PBS, OVA (200 ng), or (OVA)-3-1 (200 ng). FIG. 6C shows that 3 days after immunization, draining inguinal lymph nodes and spleen were isolated and the expansion of CD45.2$^+$Vα2 cells was evaluated by flow cytometry. Each panel represents two or more experiments.

FIG. 7A includes two dot plots showing the 5-(6)-carboxyfluorescein diacetate succinimidyl ester (CFSE), a cell-permeable dye, intensity present in a population of cells.

2×10⁷ CFSE-labeled OTII splenocytes were adoptively transferred to B6.Ly5.2/Cr recipients and the mice were immunized subcutaneously with OVA (200 ng) or (OVA)-3-1 (200 ng) emulsified in Complete Freund's Adjuvant. At seventy-two hours post immunization the draining inguinal lymph nodes were isolated and the expansion of CD45.2⁺Vα2⁺ was evaluated for CFSE dilution by flow cytometry. 4×10⁵ total counts were collected. The plots display the CFSE intensity associated with the gated population of Vα2⁺CD45.2⁺ donor cells. The numbers indicate the percentage of CFSE high (undivided; R3 gate) and CFSE low (divided; R4 gate) OTII T cells. FIG. 7B is a series of five dot plots showing the enhancement in T cell proliferation promoted by neoglycoprotein mBSA. CFSE-labeled OTII splenocytes were adoptively transferred as in (A) and mice were immunized subcutaneously with mBSA (50 µg); OVA (50 ng); (OVA)-3-1 (50 ng); OVA (50 ng)+mBSA (50 µg) or (OVA)-3-1 (50 ng)+mBSA (50 µg). At 3 days the mice were sacrificed and isolated cells were analyzed as described in (A). Both FIGS. 7A and 7B are results from one of two separate experiments.

FIG. 8A is a series of five dot plots showing that at day ten after immunization, (OVA)-3-1 immunized mice have a much greater number of OTII T cells than OVA immunized mice. 2×10⁷ OTII splenocytes were adoptively transferred into B6.Ly5.2/Cr recipients and then immunized by subcutaneous injection with PBS, OVA (200 ng), (OVA)-3-1 (200 ng), (OVA)-3-1 (200 ng)+mBSA (50 µg) or OVA peptide (100 µg) in Incomplete Freund's Adjuvant. At 8 days after these initial immunizations, mice received an antigenic rechallenge of OVA peptide (100 µg) in Complete Freund's Adjuvant. On day ten mice were sacrificed and cells were isolated from the draining lymph node, total T cells were purified by negative selection and the number of OTII T cells were counted by FACS as described for FIG. 6. FIG. 8B is a graph showing that isolated T cells from (OVA)-3-1 immunized mice are refractory to antigenic stimulation in vitro. Purified T cells from each experimental group were seeded at 3×10⁵ cells/well with purified CD1 dendritic cells (9×10⁴/well) and were incubated for twenty-four hours±OVA peptide (100 µg mL⁻¹) with [³H] thymidine (1 µCi) added for the last ten hours. Prior to [³H] thymidine addition, an aliquot of supernatant was removed for IFN-γ determination by ELISA.

FIGS. 9A, 9B, and 9C relate to the carbohydrate recognition domain of a C-type lectin. FIG. 9A shows the sequence of the CRD (SEQ ID NO: 10). FIG. 9B is a schematic diagram showing the organization of the domain. FIG. 9C provides an alignment of the amino acid sequences of the rat mannose binding protein C (SEQ ID NO: 11) and murine L-selectin (SEQ ID NO: 12).

Figure 1:
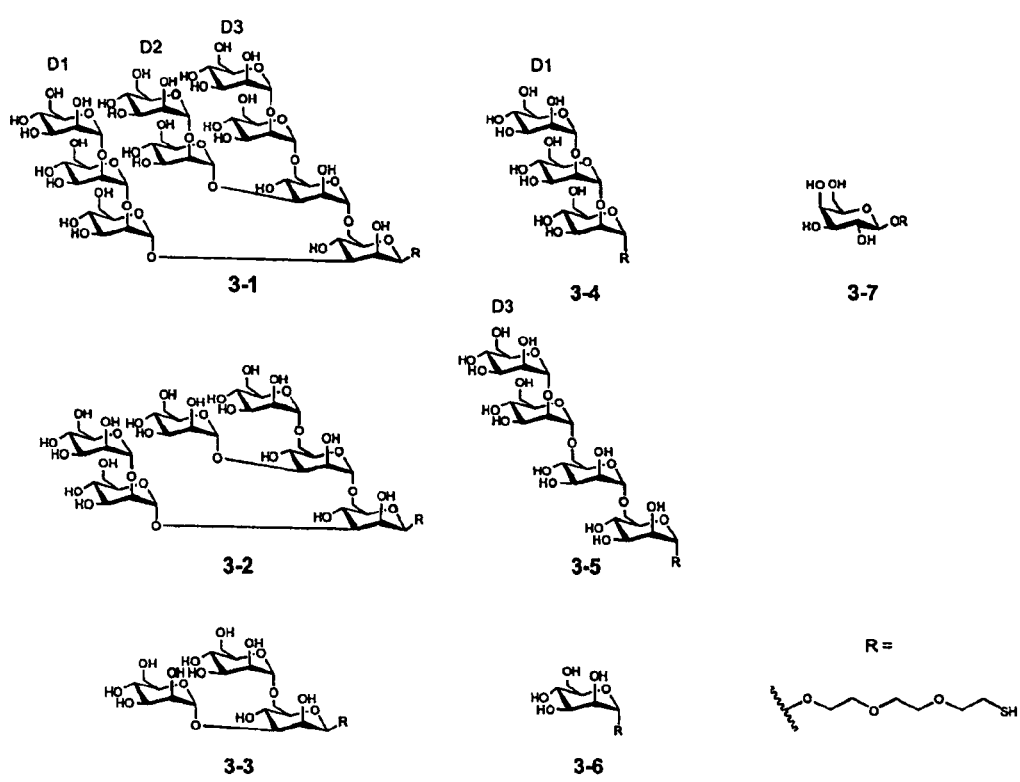
FIG. 1 shows the molecular structure of synthetic analogs of the high-mannose oligosaccharide $(Man)_9(GlcNAc)_2$ used in the preparation of ovalbumin conjugates for dendritic cell targeting. These structures were chosen for dendritic cell targeting on the basis of their recognition by the dendritic cell lectin, DC-SIGN. The panel of structures consists of three branched oligosaccharides (3-1 thru 3-3), two linear trisaccharides (3-4 and 3-5) derived from the D1 and D3 arms of the high-mannose nonasaccharide and two monosaccharides, mannose 3-6 and galactose 3-7. Conjugation of each structure was made possible by the incorporation of a thiol-bearing linker (shown as 'R' here).

```
                   BRIEF DESCRIPTION OF THE SEQUENCES

SEQ ID NO: 1 is MMR or CD206, having an amino acid sequence
MRLPLLLVFASVIPGAVLLLDTRQFLIYNEDHKRCVDAVSPSAVQTAACNQDAESQ

KFRWVSESQIMSVAFKLCLGVPSKTDWVAITLYACDSKSEFQKWECKNDTLLGIKG

EDLFFNYGNRQEKNIMLYKGSGLWSRWKIYGTTDNLCSRGYEAMYTLLGNANGA

TCAFPFKFENKWYADCTSAGRSDGWLWCGTTIDYDTDKLFGYCPLKFEGSESLWN

KDPLTSVSYQINSKSALTWHQARKSCQQQNAELLSITEIHEQTYLTGLTSSLTSGLWI

GLNSLSFNSGWQWSDRSPFRYLNWLPGSPSAEPGKSCVSLNPGKNAKWENLECVQ

KLGYICKKGNTTLNSFVIPSESDVPTHCPSQWWPYAGHCYKIHRDEKKIQRDALTTC

RKEGGDLTSIHTIEELDFIISQLGYEPNDELWIGLNDIKIQMYFEWSDGTPVTFTKWL

RGEPSHENNRQEDCVVMKGKDGYWADRGCEWPLGYICKMKSRSQGPEIVEVEKG

CRKGWKKHHFYCYMIGHTLSTFAEANQTCNNENAYLTTIEDRYEQAFLTSFVGLRP

EKYFWTGLSDIQTKGTFQWTIEEEVRFTHWNSDMPGRKPGCVAMRTGIAGGLWDV

LKCDEKAKFVCKHWAEGVTHPPKPTTTPEPKCPEDWGASSRTSLCFKLYAKGKHE

KKTWFESRDFCRALGGDLASINNKEEQQTIWRLITASGSYHKLFWLGLTYGSPSEGF

TWSDGSPVSYENWAYGEPNNYQNVEYCGELKGDPTMSWNDINCEHLNNWICQIQ

KGQTPKPEPTPAPQDNPPVTEDGWVIYKDYQYYFSKEKETMDNARAFCKRINFGDL

VSIQSESEKKFLWKYVNRNDAQSAYFIGLLISLDKKFAWMDGSKVDYVSWATGEP

NFANEDENCVTMYSNSGFWNDINCGYPNAFICQRHNSSINATTVMPTMPSVPSGCK

EGWNFYSNKCFKIFGFMEEERKNWQEARKACIGFGGNLVSIQNEKEQAFLTYHMK

DSTFSAWTGLNDVNSEHTFLWTDGRGVHYTNWGKGYPGGRRSSLSYEDADCVVII

GGASNEAGKWMDDTCDSKRGYICQTRSDPSLTNPPATIQTDGFVKYGKSSYSLMR

QKFQWHEAETYCKLHNSLIASILDPYSNAFAWLQMETSNERVWIALNSNLTDNQYT
```

BRIEF DESCRIPTION OF THE SEQUENCES

WTDKWRVRYTNWAADEPKLKSACVYLDLDGYWKTAHCNESFYFLCKRSDEIPAT

EPPQLPGRCPESDHTAWIPFHGHCYYIESSYTRNWGQASLECLRMGSSLVSIESAAE

SSFLSYRVEPLKSKTNFWIGLFRNVEGTWLWINNSPVSFVNWNTGDPSGERNDCVA

LHASSGFWSNIHCSSYKGYICKRPKIIDAKPTHELLTTKADTRKMDPSKPSSNVAGV

VIIVILLILTGAGLAAYFFYKKRRVHLPQEGAFENTLYFNSQSSPGTSDMKDLVGNIE

QNEHSVI, arising from *Homo sapiens*;

SEQ ID NO: 2 is DEC-205 or CD205, having an amino acid sequence
MRTGWATPRRPAGLLMLLFWFFDLAEPSGRAANDPFTIVHGNTGKCIKPVYGWIV

ADDCDETEDKLWKWVSQHRLFHLHSQKCLGLDITKSVNELRMFSCDSSAMLWWK

CEHHSLYGAARYRLALKDGHGTAISNASDVWKKGGSEESLCDQPYHEIYTRDGNS

YGRPCEFPFLIDGTWHHDCILDEDHSGPWCATTLNYEYDRKWGICLKPENGCEDN

WEKNEQFGSCYQFNTQTALSWKEAYVSCQNQGADLLSINSAAELTYLKEKBGIAKI

FWIGLNQLYSARGWEWSDHKPLNFLNWDPDRPSAPTIGGSSCARMDAESGLWQSF

SCEAQLPYVCRKPLNNTVELTDVWTYSDTRCDAGWLPNNGFCYLLVNESNSWDK

AHAKCKAFSSDLISIHSLADVEVVVTKLHNEDIKEEVWIGLKNINIPTLFQWSDGTE

VTLTYWDENEPNVPYNKTPNCVSYLGELGQWKVQSCEEKLKYVCKRKGEKLNDA

SSDKMCPPDEGWKRHGETCYKIYBDEVPFGTNCNLTITSRFEQEYLNDLMKKYDKS

LRKYFWTGLRDVDSCGEYNWATVGGRRRAVTFSNWNFLEPASPCGCVAMSTGKS

VGKWEVKDCRSFKALSICKKMSGPLGPEEASPKPDDPCPEGWQSFPASLSCYKVFH

AERIVRKRNWEEAERFCQALGAHLSSFSHVDEIKEFLHFLTDQFSGQHWLWIGLNK

RSPDLQGSWQWSDRTPVSTIIMPNEFQQDYDIRDCAAVKVFHRPWRRGWHFYDDR

EFIYLRPFACDTKLEWVCQIPKGRTPKTPDWYNPDRAGIHGPPLIIEGSEYWFVADL

HLNYEEAVLYCASNHSFLATITSFVGLKAIKNKIANISGDGQKWWIRISEWPIDDHFT

YSRYPWHRFPVTFGEECLYMSAKTWLIDLGKPTDCSTKLPPFICEKYNVSSLEKYSPD

SAAKVQCSEQWIPFQNKCFLKIKPVSLTFSQASDTCHSYGGTLPSVLSQIEQDFITSL

LPDMEATLWIGLRWTAYEKINKWTDNRELTYSNFHPLLVSGRLRPENFFEEESRYH

CALILNLQKSPFTGTWNFTSCSERHFVSLCQKYSEVKSRQTLQNASETVKYLNNLY

KIIPKTLTWHSAKRECLKSNMQLVSITDPYQQAFLSVQALLHNSSLWIGLFSQDDEL

NFGWSDGKRLHFSRWAETNGQLEDCVVLDTDGFWKTVDCNDNQPGAICYYSGNE

TEKEVKPVDSVKCPSPVLNTPWIPFQNCCYNFIITKNRHMATTQDEVHTKCQKLNP

KSHILSIRDEKENNFVLEQLLYFNYMASWVMLGITYRNNSLMWFDKTPLSYTHWR

AGRPTIKNEKFLAGLSTDGFWDIQTFKVIEEAVYFHQHSILACKIEMVDYKEEHNTT

LPQFMPYEDGIYSVIQKKVTWYEALNMCSQSGGHLASVHNQNGQLFLEDIVKRDG

FPLWVGLSSHDGSESSFEWSDGSTFDYIPWKGQTSPGNCVLLDPKGTWKHEKCNSV

KDGAICYKPTKSKKLSRLTYSSRCPAAKENGSRWIQYKGHCYKSDQALHSFSEAKK

LCSKHDHSATIVSIKDEDENKFVSRLMRENNNITMRVWLGLSQHSVDQSWSWLDG

SEVTFVKWENKSKSGVGRCSMLIASNETWKKVECEHGFGRVVCKVPLGPDYTAIAI

IVATLSILVLMGGLIWFLFQRHRLHLAGFSSVRYAQGVNEDEIMLPSFHD, arising from *Homo sapiens*;

SEQ ID NO: 3 is Dectin 1, having an amino acid sequence

BRIEF DESCRIPTION OF THE SEQUENCES

MEYHPDLENLDEDGYTQLHFDSQSNTRIAVVSEKGSCAASPPWRLIAVILGILCLVIL

VIAVVLGTMAIWRSNSGSNTLENGYFLSRNKENHSQPTQSSLEDSVTPTKAVKTTG

VLSSPCPPNWIIYEKSCYLFSMSLNSWDGSKRQCWQLGSNLLKIDSSNELGFIVKQV

SSQPDNSFWIGLSRPQTEVPWLWEDGSTFSSNLFQIRTTATQENPSPNCVWIHVSVIY

DQLCSVPSYSICEKKFSM, arising from *Homo sapiens*;

SEQ ID NO: 4 is Dectin 2, having an amino acid sequence
MMQEQQPQSTEKRGWLSLRLWSVAGISIALLSACFIVSCVVTYHFTYGETGKRLSE

LHSYHSSLTCFSEGTKVPAWGCCPASWKSFGSSCYFISSEEKVWSKSEQNCVEMGA

HLVVFNTEAEQNFIVQQLNESFSYFLGLSDPQGNNNWQWIDKTPYEKNVRFWHLG

EPNHSAEQCASIVFWKPTGWGWNDVICETRRNSICEMNKIYL, arising from *Homo sapiens*;

SEQ ID NO: 5 is Langerin or CD 207, having an amino acid sequence
MTVEKEAPDAHFTVDKQNISLWPREPPPKSGPSLVPGKTPTVRAALICLTLVLVASV

LLQAVLYPRFMGTISDVKTNVQLLKGRVDNISTLDSEIKKNSDGMEAAGVQIQMVN

ESLGYVRSQFLKLKTSVEKANAQIQILTRSWEEVSTLNAQIPELKSDLEKASALNTKI

RALQGSLENMSKLLKRQNDILQVVSQGWKYFKGNFYYFSLIPKTWYSAEQFCVSR

NSHLTSVTSESEQEFLYKTAGGLIYWIGLTKAGMEGDWSWVDDTPFNKVQSARFW

IPGEPNNAGNNEHCGNIKAPSLQAWNDAPCDKTFLFICKRPYVPSEP, arising from

*Homo sapiens*;

SEQ ID NO: 6 is DC-SIGN or CD 209, having an amino acid sequence
MSDSKEPRLQQLGLLEEEQLRGLGFRQTRGYKSLAGCLGHGPLVLQLLSFTLLAGL

LVQVSKVPSSISQEQSRQDAIYQNLTQLKAAVGELSEKSKLQEIYQELTQLKAAVGE

LPEKSKLQEIYQELTRLKAAVGELPEKSKLQEIYQELTWLKAAVGELPEKSKMQEIY

QELTRLKAAVGELPEKSKQQEIYQELTRLKAAVGELPEKSKQQEIYQELTRLKAAV

GELPEKSKQQEIYQELTQLKAAVERLCHPCPWEWTFFQGNCYFMSNSQRNWHDSIT

ACKEVGAQLVVIKSAEEQNFLQLQSSRSNRFTWMGLSDLNQEGTWQWVDGSPLLP

SFKQYWNRGEPNNVGEEDCAEFSGNGWNDDKCNLAKFWICKKSAASCSRDEEQFL

SPAPATPNPPPA, arising from *Homo sapiens*;

SEQ ID NO: 7 is BDCA-2, having an amino acid sequence
MVPEEEPQDREKGLWWFQLKVWSMAVVSILLLSVCFTVSSVVPHNFMYSKTVKRL

SKLREYQQYHPSLTCVMEGKDIEDWSCCPTPWTSFQSSCYFISTGMQSWTKSQKNC

SVMGADLVVINTREEQDFIIQNLKRNSSYFLGLSDPGGRRHWQWVDQTPYNENVTF

WHSGEPNNLDERCAIINFRSSEEWGWNDIHCHVPQKSICKMKKIYI, arising from

*Homo sapiens*;

SEQ ID NO: 8 is DCIR, having an amino acid sequence
MTSEITYAEVRFKNEFKSSGINTASSAASKERTAPHKSNTGFPKLLCASLLIFFLLLAI

SFFIAFVIFFQKYSQLLEKKTTKELVHTTLECVKKNMPVEETAWSCCPKNWKSFSSN

CYFISTESASWQDSEKDCARMEAHLLVINTQEEQDFIFQNLQEESAYFVGLSDPEGQ

RHWQWVDQTPYNESSTFWHPREPSDPNERCVVLNFRKSPKRWGWNDVNCLGPQR

SVCEMMKIHL, arising from *Homo sapiens*;

SEQ ID NO: 9 is ASGPR, having an amino acid sequence
MTKEYQDLQHLDNEESDHHQLRKGPPPPQPLLQRLCSGPRLLLLSLGLSLLLLVVV -continued

BRIEF DESCRIPTION OF THE SEQUENCES

CVIGSQNSQLQEELRGLRETFSNFTASTEAQVKGLSTQGGNVGRKMKSLESQLEKQ

QKDLSEDHSSLLLHVKQFVSDLRSLSCQMAALQGNGSERTCCPVNWVEHERSCYW

FSRSGKAWADADNYCRLEDAHLVVVTSWEEQKFVQHHIGPVNTWMGLHDQNGP

WKWVDGTDYETGFKNWRPEQPDDWYGHGLGGEDCAHFTDDGRWNDDVCQRP

YRWVCETELDKASQEPPLL, arising from Homo sapiens;

SEQ ID NO: 10 is CRD, a portion of consensus sequence of a C-type lectin carbohydrate-recognition domain, having the amino acid sequence shown in FIG. 9A SEQ ID NO: 11 is rat mannose binding protein C, having an amino acid sequence
ENWGAGEPNNKKSKEDCVEIYIKRERDSGKWNDDACHKRKAALCY;

SEQ ID NO: 12 is murine L-selectin, having an amino acid sequence
TNWNEGEPNNVGSGENCVVLLTNGKWNDVPCSDSFLVVCE;
and SEQ ID NO: 13 is CIRE, having an amino acid sequence
MSDSKEMGKRQLRPLDEELLTSSHTRHSIKGFGFQTNSGFSSFTGCLVHSQVPLALQ

VLFLAVCSVLLVVILVKVYKIPSSQEENNQMNVYQELTQLKAGVDRLCRSCPWDW

THFQGSCYFFSVAQKSWNDSATACHNVGAQLVVIKSDEEQNFLQQTSKKRGYTW

MGLIDMSKESTWYWVDGSPLTLSFMKYWSKGEPNNLGEEDCAEFRDDGWNDTKC

TNKKFWICKKLSTSCPSK, arising from Mus musculus.

DETAILED DESCRIPTION

The present invention generally relates to antigen presentation and/or immune modulation using antigen-carbohydrate conjugates able to bind lectins on dendritic cells or other antigen presenting cells, for example, to induce immunity or immunological tolerance (e.g., anergy) within a subject. In some cases, the lectins that the conjugates are able to bind are preferentially expressable by dendritic cells and/or other antigen-presenting cells, relative to other cells. In one aspect of the invention, dendritic cells and/or antigen-presenting cells are exposed to antigen-carbohydrate conjugates, in vivo, ex vivo, or in vitro. The carbohydrates of the antigen-carbohydrate conjugate may be selected for their ability to bind lectins, including lectins expressed by dendritic cells and/or other antigen-presenting cells. Optionally, other agents may be included with the antigen-carbohydrate conjugate, such as adjuvants, cytokines, haptens, pharmaceutically acceptable carriers, etc. In another aspect of the invention, a carbohydrate may be identified by screening a carbohydrate library against a lectin, for example, that is expressed by a dendritic cell and/or other antigen-presenting cell. The carbohydrate may then be conjugated to an antigen. Other aspects of the invention relate to kits and compositions including certain antigen-carbohydrate conjugates, as well as techniques of making, using, and promoting such conjugates.

Various aspects of the present invention are directed to antigen-carbohydrate conjugates able to bind lectins expressable on the surfaces of dendritic cell and/or other antigen-presenting cell. As previously discussed, dendritic cells are one type of antigen-presenting cell found within the immune system, and can be found in many systems and organs within the body, especially the lymphoid organs. As used herein, the term "dendritic cell" is given its ordinary meaning in the art, and also includes specialized dendritic cells, such as Langerhans cells (which can express Langerin or CD 207), dermal dendritic cells, interstitial dendritic cells, interdigitating dendritic cells, follicular dendritic cells, blood dendritic cells, veiled cells, plasmacytoid BDCA-2-expressing dendritic cells, myeloid dendritic cells, CD1a+ dendritic cells, DC-SIGN-expressing dendritic cells, etc. By "DC-SIGN" is meant a protein that is substantially identical (e.g., having at least 75%, 80%, 85%, 90%, or 95% amino acid sequence identity) to SEQ ID NO:6. In one embodiment, however, Langerin-negative dendritic cells are used. Examples of non-dendritic, antigen-presenting cells include macrophages and monocytes. Those of ordinary skill in the art will know of routine techniques for identifying dendritic cells relative to other cells of the immune system (e.g., B cells and T cells), for example, using various biomolecular assays, through microscopic examination, cytometry, etc. It should also be noted that certain antigen-carbohydrate conjugates described below may be selected for their ability to selectively bind to certain types of dendritic cells, relative to other types of dendritic cells. As a non-limiting example, an antigen-carbohydrate conjugate may be prepared that selectively binds a lectin expressed by dermal dendritic cells but is not substantially expressed by other dendritic cells such as Langerhan cells, etc.

Immune Condition Therapies

Exposure of dendritic cells and/or other antigen-presenting cells to antigen-carbohydrate conjugates may be useful, according to one set of embodiments, in the treatment of immune conditions in a subject, for example, to induce immunity against pathogens, tumor or other disease causing entities or tolerance (including anergy, deletion, and/or regulatory activity of T cells) against auto-antigens or allergens, or the like. A "subject," as used herein, means a human or non-human mammal, including but not limited to, a dog, cat, horse, cow, pig, sheep, goat, chicken, primate, rat, and mouse.

In some cases, the antigen-carbohydrate conjugates of the invention may be directly administered to a subject; in other cases, however, the subject may be indirectly exposed to the antigen-carbohydrate conjugate, e.g., the antigen-carbohydrate conjugate may be exposed to dendritic cells and/or other antigen-presenting cells in vitro, then the dendritic cells and/or other antigen-presenting cells are administered to the subject (e.g., ex vivo therapy).

Immunity Induction

In some embodiments, a subject is exposed to an antigen-carbohydrate conjugate to activate the immune system with respect to the antigen, e.g., to induce immunity to the antigen, and/or to entities that comprise the antigen. An "antigen" is any agent that can induce an immune response. The antigen within the antigen-carbohydrate conjugate may be any molecule that can be detected by the immune system, and for which a change in the immune response (i.e., immunity, tolerance, etc.) is desired. An "immune response" is any biological response to an antigen (e.g., any cellular response that contributes to adaptive or innate immunity). For example, the antigen may be a fungus, parasite, virus, worm, bacterium, or other pathogen. or the antigen may be a complex of molecules or a single molecular species (e.g., a polysaccharide, a protein such as ovalbumin, a peptide, a toxin, etc.) that arises from the above-described pathogens. Other examples of antigens are further described below. The antigen may be a nonself antigen (arising from non-human sources, such as the above-described pathogens and/or molecular components from the above-described pathogens; or from another human)-or a self antigen (arising from the subject, for example, normal cells, diseased cells, autoimmune tissues, tumors, etc.). If nonself, the antigen may be from the same or a different species as the subject. In some cases, the antigen may be attenuated (e.g., at least partially inactivated or crippled) or inactivated (e.g., killed or otherwise rendered into a nonfunctional state, such as for viruses or toxins). As one example, an antigen-carbohydrate conjugate, containing an antigen arising from a virus, bacterium, a cancer cell, etc., is administered to a subject, optionally along with an adjuvant such as alum, CpG, polyI: C, LPS, a dendritic cell activating agent, etc. The antigen-carbohydrate conjugate, upon binding to dendritic cells and/or other antigen-presenting cells within the subject, can cause an immune response to the antigen, e.g., due to exposure of T cells and/or B cells within the subject to the antigen, now associated with the dendritic cells and/or other antigen-presenting cells. The immune response may enable the subject's body to fight the infection or cancer more effectively, and/or the immune response may cause the subject to develop an immunity to future attacks of the virus, bacterium, cancer, etc.

In some cases, the antigen-carbohydrate conjugate may be delivered in an amount effective to "promote maturation of dendritic cells" and/or other antigen-presenting cells, i.e., the antigen-carbohydrate conjugate, when added to immature dendritic or other cells, accelerates their maturity with respect to their maturity rate in the absence of the conjugate. Those of ordinary skill in the art will know of suitable techniques for determining whether a given antigen-carbohydrate conjugate is able to promote maturation of dendritic cells and/or other antigen-presenting cells. For example, immature cells may be cultured in vitro, and one culture may be exposed to a antigen-carbohydrate conjugate while a control culture is kept free of the conjugate. The respective rates of maturity for the two cultures may then be determined and compared for statistical significance. This may be assessed, for instance, by examining cell surface molecules such as MHC class I, CD86, CD54, CD83, etc. Dendritic cell maturation (and/or maturation of other antigen-presenting cell) may enhance immunity of the subject to the antigen, for example, by enhancing the immune response tp the antigen.

Tolerance Induction

In another set of embodiments, a subject is exposed to an antigen-carbohydrate conjugate to cause anergy or tolerance within the subject with respect to the antigen. For example, the subject may be suffering from an allergy or hypersensitivity (e.g., to proteins, pollen, drugs such as penicillin or sulfonamides, nuts, seafood, eggs, peas, beans, venoms such as bee venom, molds, animal hair, dander, etc.), or the subject may be suffering from an autoimmune or inflammatory disease (e.g., Addison's disease, autoimmune anemia, Goodpasture's syndrome, Graves' disease, Hashimoto's thyroiditis, idiopathic thrombocytopenia purpura, type I diabetes, myasthenia gravis, ankylosing spondylitis, multiple sclerosis, rheumatoid arthritis, psoriasis, Crohn's disease, scleroderma, Sjögren's syndrome, or systemic lupus erythematosus, all of which have been characterized as chronic diseases caused, at least in part, by an immune system that is self-reactive) in which the subject's immune system abnormal attacks its own tissues, leading to tissue damage and/or disease.

For autoimmune diseases, it is possible to construct an couple carbohydrates to antigens that are found as targets of autoimmune responses (e.g. insulin or GAD for diabetes, myelin basic protein for multiple sclerosis, acetylcholine receptor for myasthenia gravis, etc.), immunize and thus reduce the autoimmune response due to T and B cells. (Yoon J W, Jun H S. Cellular and molecular pathogenic mechanisms of insulin-dependent diabetes mellitus. Ann N Y Acad. Sci. 2001 April; 928:200-11; M S, Stinissen P, Medaer R, Raus J. Myelin reactive T cells in the autoimmune pathogenesis of multiple sclerosis. Mult Scler. 1998 June; 4(3):203-11; De Baets M, Stassen M H. The role of antibodies in myasthenia gravis. J Neurol Sci. 2002 Oct. 15; 202(1-2):5-11;). Accordingly, autoimmune antigens useful in the methods of the invention include, but are not limited to the following: insulin-B (Genbank Accession No. J00265) or GAD (Genbank Accession No. M74826), myelin basic protein (Genbank Accession No. X17286), and acetylcholine receptor alpha subunit (Genbank Accession No. y00762).

In some cases, anergy may be induced by exposing the subject to low levels of an antigen-carbohydrate conjugate, thus causing the antigen to appear at relatively low concentrations within the dendritic cells and/or other antigen-presenting cells. The antigen may be a self-antigen in some instances, e.g., auto-immune diseases. In other cases, anergy may be induced by exposing the subject to an antigen-carbohydrate conjugate and also exposing the subject to a desensitizing agent, for example, CTLA4-Ig or a blocking antibody to CD40L, which may cause the relevant T cells to enter a state of anergy, and/or be deleted to become regulatory T cells.

The antigen-carbohydrate conjugate may be administered to the subject, in certain embodiments of the invention, in an amount that is effective to induce T cell anergy (in which T cells enter a state in which they cannot be reactivated by antigen), deletion (i.e., such that the T cells, upon exposure to the antigen-carbohydrate conjugate, undergo death and/or elimination), or other regulatory activity (e.g., where T cells are able to actively suppress other antigen-specific T cells from being activated). In one embodiment, the antigen-carbohydrate conjugate is delivered in an amount effective to tolerize allergen-specific T cells. In another embodiment, the antigen-carbohydrate conjugate is delivered in an amount effective to inhibit maturation of dendritic cells and/or other antigen-presenting cells. The inhibition can be complete or partial, i.e., by slowing cell maturation. Those of ordinary skill in the art will know of suitable techniques for determining whether a given antigen-carbohydrate conjugate is able to induce tolerance, for example, by measuring T cell activation to specific antigens ex vivo and determining the strength of the response before and after treatment of a subject with the antigen-carbohydrate conjugate.

In some embodiments of the invention, the antigen conjugated to the carbohydrate may arise from a pool of tissue/cell antigens, for instance, where antigens are derived from an animal, a plant, microbe, fungus, bacterium, virus, cell (normal or diseased), or other source of antigen. Multiple antigens may be present in certain instances. The pool of antigens may be isolated from a source, such as a living source, by lysing cells and tissues with cell disruption solutions (e.g. PBS+1% TritonX-100) and isolating antigens using appropriate purification procedures (e.g. size exclusion and ion exchange chromatography) or the pool of antigens may be artificially generated (for example, using available combinatorial chemistry techniques or over-expressing mixtures of recombinant antigens in mammalian cells, insect cells or bacteria). In some cases, the specific chemical identity of the antigen is not known, so king as the antigen can be conjugated to the carbohydrate. In other cases, however, the antigen may be pre-selected or predetermined. Non-limiting examples of such antigens include those described above.

Thus, in some cases, the antigen-carbohydrate conjugate can be delivered to a subject to treat an allergy within the subject. Examples of allergic conditions or diseases in humans that may be treated according to embodiments of the invention include, but are not limited to, eczema, allergic rhinitis or coryza, hay fever, conjunctivitis, bronchial or allergic asthma, urticaria (hives) and food allergies, atopic dermatitis, anaphylaxis, drug allergy, angioedema, and allergic conjunctivitis. Allergic diseases in dogs include, but are not limited to, seasonal dermatitis, perennial dermatitis, rhinitis: conjunctivitis, allergic asthma, and drug reactions. Allergic diseases in cats include but are not limited to dermatitis and respiratory disorders, and food allergens. Allergic diseases in horses include but are not limited to respiratory disorders, such as "heaves" and dermatitis. Allergic diseases in non-human primates include but are not limited to allergic asthma and allergic dermatitis.

Further examples of antigens, or entities in which suitable antigens can be derived from using techniques known to those of ordinary skill in the art (e.g., antigen pools), include, but are not limited to, certain airborne particulates, plant pollen (e.g., weed pollen, grass pollen, Johnson grass, tree pollen (for example, oak, maple, cedar, etc.), ryegrass, etc.), mites (e.g., house dust mites), molds, spores, certain animals (e.g., cats, dogs, guinea pigs, hamsters, gerbils, rats, mice, etc.), food (e.g., crustaceans, nuts such as peanuts, citrus fruits, etc.), insect or insect venoms (e.g., *Hymenoptera*, yellow jacket, honeybee, wasp, hornet, fire ant, cockroaches, fleas, mosquitoes, etc.), bacteria (e.g., *Streptococcus*), parasites (e.g., *plasmodium, Ascaris*), viruses, fungi, drugs and their metabolites (e.g., penicillins and related compounds), whole proteins such as hormones (e.g., insulin) or enzymes (Streptokinase), certain chemicals and metabolites (e.g., acid anhydrides such as trimellitic anhydride, or isocyanates such as toluene diisocyanate), occupational species (e.g., flour (Baker's asthma), castor beans, coffee beans), human proteins in non-human animals, or the like. In some cases, the antigen is derived from a living source (incuding human and non-human sources), and in other cases, the antigen is derived from a non-living source. Antigens may also be derived from cells (such as pancreatic beta cells, myelin sheaths of nerves, synovial fluid and tissue, skin, tumors of any type, any body tissue) or cell extracts, or may be proteins, polypeptides, peptides, polysaccharides, polysaccharide conjugates, peptide and non-peptide mimics of polysaccharides and other molecules, small molecules, lipids, glycolipids, carbohydrates, fats, etc. Small molecules of the invention preferably have a molecular weight below 2,000 daltons, more preferably between 300 and 1,000 daltons (e.g., 300, 400, 500, 600, 700, 800, 900, and 1,000), and most preferably between 400 and 700 (e.g., 400, 450, 500, 600, 650, and 700) daltons. It is preferred that these small molecules are organic molecules.

Specific non-limiting examples of natural animal and plants from which antigens can be derived from using techniques known to those of ordinary skill in the art include the following genera: Canine (e.g., *Canis familiaris*); Dermatophagoides (e.g., *Dermatophagoides farinae*); Felis (e.g., *Felis domesticus*); Ambrosia (e.g., *Ambrosia artemiisfolia*); Lolium (e.g., *Lolium perenne* or *Lolium multiflorum*); Cryptomeria (e.g., *Cryptomeria japonica*); Alternaria (e.g., *Alternaria alternata*); Alder; Alnus (e.g., *Alnus gultinoasa*); Betula (e.g., *Betula verrucosa*); Quercus (e.g., *Quercus alba*); Olea (e.g., *Olea europa*); Artemisia (*Artemisia vulgaris*); Plantago (e.g., *Plantago lanceolata*); Parietaria (e.g., *Parietaria officinalis* or *Parietaria judaica*); Blattella (e.g., *Blattella germanica*); Apis (e.g., *Apis multiflorum*); Cupressus (e.g., *Cupressus sempervirens, Cupressus arizonica*, or *Cupressus macrocarpa*); Juniperus (e.g., *Juniperus sabinoides, Junifierus virginiana, Juniperus communis,* or *Juniperus ashei*); Thuya (e.g., *Thuya orientalis*); Chamaecyparis (e.g., *Chamaecyparis obtusa*); Periplaneta (e.g., *Periplaneta americana*); Agropyron (e.g., *Agropyron repens*); Secale (e.g., *Secale cereale*); Triticum (e.g., *Triticum aestivum*); Dactylis (e.g., *Dactylis glomerata*); Festuca (e.g., *Festuca elatior*); Poa (e.g., *Poa pratensis* or *Poa compressa*); Avena (e.g., *Avena sativa*); Holcus (e.g., *Holcus lanatus*); Anthoxanthum (e.g., *Anthoxanthum odoratum*); Arrhenatherum (e.g., *Arrhenatherum elatius*); Agrostis (e.g., *Agrostis alba*); Phleum (e.g., *Phleum pratense*); Phalaris (e.g., *Phalaris arundinacea*); Paspalum (e.g., *Paspalum notatum*); Sorghum (e.g., *Sorghum halepensis*); and Bromus (e.g., *Bromus inermis*).

Antigens can also be derived from cell surface molecules or extracts of infectious agents. For instance, infectious bacteria include, but are not limited to, gram negative and gram positive bacteria. Gram positive bacteria include, but are not limited to *Pasteurella* species, Staphylococci species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g., *M. tuberculosis, M. avium, M. intracellulare, M. kansaii, M. gordonae*, etc.), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli*.

Viruses include, but are not limited to, interoviruses (e.g., viruses that the family picornaviridae, such as polio virus, coxsackie virus, echo virus), rotaviruses, adenovirus, hepatitus, etc. Specific examples of viruses that have been found in humans include, but are not limited to, Retroviridae (e.g., human immunodeficiency viruses, such as HIV-1, also referred to as HTLV-III, LAV or HTLV-III/LAV, or HIV-III, and other isolates, such as HIV-LP), Picornaviridae (e.g., polio viruses, hepatitis A virus, enteroviruses, human Coxsackie viruses, rhinoviruses, echoviruses, etc.), Calciviridae (e.g., strains that cause gastroenteritis), Togaviridae (e.g., equine encephalitis viruses, rubella viruses, etc.), Flaviridae (e.g., dengue viruses, encephalitis viruses, yellow fever viruses, etc.), Coronoviridae (e.g., coronaviruses); Rhabdoviradae (e.g., vesicular stomatitis viruses, rabies viruses, etc.); Coronaviridae (e.g., coronaviruses), Rhabdoviridae (e.g., vesicular stomatitis viruses, rabies viruses, etc.), Filoviridae (e.g., ebola viruses), Paramyxoviridae (e.g., parainfluenza viruses, mumps virus, measles virus, respiratory syncytial virus, etc.), Orthomyxoviridae (e.g., influenza viruses), Bungaviridae (e.g., Hantaan viruses, bunga viruses, phleboviruses, Nairo viruses, etc.), Arena viridae (e.g., hemorrhagic fever viruses), Reoviridae (e.g., reoviruses, orbiviurses, rotaviruses, etc.), Birnaviridae, Hepadnaviridae (Hepatitis B virus), Parvovirida (parvoviruses), Papovaviridae (e.g., papilloma viruses, polyoma viruses, etc.), Adenoviridae (adenoviruses), Herpesviridae (e.g., herpes simplex virus (HSV) 1 and 2, varicella zoster virus, cytomegalovirus (CMV), herpes virus, etc.), Poxyiridae (e.g., variola viruses, vaccinia viruses, pox viruses), Iridoviridae (e.g., African swine fever virus), as well as other unclassified viruses (e.g., the etiological agents of Spongiform encephalopathies, the agent of delta hepatitis, the agents of non-A, non-B hepatitis (i.e. Hepatitis C), Norwalk and related viruses, astroviruses, etc.).

Examples of fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* such as *Plasmodium falciparum, Plasmodium malariae, Plasmodium ovale, Plasmodium vivax, Toxoplasma gondii*, etc.

One of ordinary skill in the art will understand that the carboydrate conjugated antigens of the invention can be used to vaccinate subjects against any known infectious agent.

Examples of infectious agents that cause disease, along with examples of antigens that can be used to vaccinate against these pathogens, include, but are not limited to: human immunodeficiency virus (gp120 protein); malaria (MSP1, AMA1, PfEMP1); tuberculosis (antigen 85 AB, ESAT-6 and heat shock protein 60); influenza (HA, NA); hepatitis B virus (HBeAg). Methods of vaccination to prevent or treat a subject having a pathogen infection are known in the art (e.g., Letvin et al., "Prospects for vaccine protection against REV-1 infection and AIDS," Annu Rev Immunol. 2002; 20:73-99; Richie et al., "Progress and challenges for malaria vaccines," Nature. 2002 Feb. 7; 415(6872):694-701; Andersen, "TB vaccines: progress and problems," Trends Immunol. 2001 March; 22(3):160-8).

In some cases, the antigen may be associated with a cancer, i.e., a cancer antigen. A "cancer antigen" as used herein is a compound, such as a peptide, associated with a tumor or cancer cell surface and which is capable of provoking an immune response, for instance, when expressed on the surface of an antigen presenting cell in the context of an MHC molecule. Cancer antigens, such as those present in cancer vaccines or those used to prepare cancer immunotherapies, can be prepared from crude cancer cell extracts, and/or by partially purifying the antigens, using recombinant technology, or de novo synthesis of known antigens. Cancer antigens can be used in the form of immunogenic portions of a particular antigen, or in some instances, a whole cell or a tumor mass (killed) can be used as the antigen. Such antigens can be isolated or prepared recombinantly or by any means known to those of ordinary skill in the art.

As used herein, the terms "cancer antigen" and "tumor antigen" are generally used interchangeably to refer to antigens which are differentially expressed by cancer cells and can thereby be exploited in order to target cancer cells. Cancer antigens are antigens which can potentially stimulate apparently tumor-specific immune responses. Some of these antigens are also encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Specific examples of tumor antigens include, but are not limited to, proteins such as Ig-idiotype of B cell lymphoma, mutant cyclin-dependent kinase 4 of melanoma, Pmel-17 (gp 100) of melanoma, MART-1 (Melan-A, MAGE-1) of melanoma, p15 protein of melanoma, tyrosinase of melanoma, MAGE 1, 2 and 3 of melanoma, GAGE family of melanoma, thyroid medullary, small cell lung cancer, colon and/or bronchial squamous cell cancer, BAGE of bladder, melanoma, breast, and squamous-cell carcinoma, gp75 of melanoma, oncofetal antigen of melanoma, etc. In some cases, the tumor antigen may include carbohydrates and/or lipids, such as mucin of breast, pancreas, and ovarian cancer, GM2 and GD2 gangliosides of melanoma.

Other non-limiting examples of tumor antigens include oncogenes such as mutant p53 of carcinoma, mutant ras of colon cancer and HER21neu proto-onco-gene of breast carcinoma, viral products such as human papilloma virus proteins of squamous cell cancers of cervix and esophagus, etc. In one set of embodiments the antigen (shown in parenthesis) may be associated or derived from the following tumors: acute lymphoblastic leukemia (e.g., etv6, aml 1, cyclophilin b, etc.), B cell non-Hodgkin's lymphoma and multiple myeloma (Ig idiotype), glioma (e.g., E-cadherin, alpha-catenin, beta-catenin, gamma-catenin, p120ctn, etc.), bladder cancer (e.g., p21ras), billiary cancer (e.g., p21ras), breast cancer (e.g., the MUC family, HER2/neu, CEA, c-erbB-2, etc.), Burkitt's lymphoma (EBV antigens), cervical carcinoma (e.g., p53, p21ras, human papilloma virus antigens E6 and E7, etc.), CML (bcr-abl fusion product), colon carcinoma (e.g., p21ras, HER2/neu, c-erbB-2, the MUC family, etc.), colorectal cancer (e.g., colorectal associated antigen (CRC)-C017-1A/GA733, APC, CEA, muc-1, etc.), choriocarcinoma (e.g., CEA), epithelial cell-cancer (e.g., cyclophilin b), gastric cancer (e.g., HER2/neu, c-erbB-2, ga733 glycoprotein, etc.), hepatocellular cancer (e.g., alpha-fetoprotein, etc.), Hodgkins lymphoma (e.g., lmp-1, EBNA-1, etc.), liver cancer (alpha-fetoprotein), lung cancer (e.g., CEA, MAGE-3, NY-ESO-1, her-2/neu, muc-1), lymphoid cell-derived leukemia (e.g., cyclophilin b), myeloma (e.g., the MUC family, p21ras, etc.), non-small cell lung carcinoma (e.g., HER2/neu, c-erbB-2, etc.), nasopharyngeal cancer (e.g., imp-1, EBNA-1, etc.), ovarian cancer (e.g., the MUC family (e.g., muc-1), HER2/neu, c-erbB-2, etc.), prostate cancer (e.g., PAA, prostate specific antigen or PSA and its immunogenic epitopes such as PSA-1, PSA-2, and PSA-3, or PSMA, HER2/neu, c-erbB-2, etc.), pancreatic cancer (e.g., p21ras, the MUC family (e.g., muc-1), HER2/neu, c-erbB-2, ga733 glycoprotein, etc.), renal (e.g., HER2/neu, c-erbB-2, etc.), testicular cancer (e.g., NY-ESO-1), thyroid cancer (thyroglobulin), T cell leukemia (e.g., HTLV-1 epitopes), melanoma (e.g., Melan-A/MART-1, cdc27, MAGE-3, p21ras, gp100$_{Pmel117}$), etc. See, e.g., Fong L, Engleman E G., "Dendritic cells in cancer immunotherapy," Annu Rev Immunol. 2000; 18:245-73.

Antigen-Carbohydrate Conjugates

As discussed above, various antigen-carbohydrate conjugates of the invention are able to bind lectins expressable on the surfaces of dendritic cells or other antigen presenting cells. Lectins are proteins or glycoproteins that have the ability to bind carbohydrates, including the antigen-carbohydrate conjugates further described herein. Lectins can be expressed by dendritic cells and other cells of the body. In some cases, the lectins are able to selectively bind or otherwise recognize carbohydrates, relative to other naturally-occurring species (e.g., proteins, hormones, etc.), and some lectins may selectively bind or recognize one class or species of carbohydrates, relative to other carbohydrates (e.g., the lectin may selectively bind or recognize mannose relative to glucose or fructose, etc.). In some cases, other species, may assist in the binding of, or recognition of, the carbohydrates to lectins, for example, small molecules or ions such as calcium ($Ca^{2+}$); an example is calcium-dependent carbohydrate binding proteins, or a "C-type lectin."

Certain lectins are selectively expressed by dendritic cells and/or other antigen-presenting cells in vivo, ex vivo, and/or in vitro, relative to their expression in other cells, e.g., other cells of the immune system, such as T cells or B cells. Lectins that may be expressed by dendritic cells and/or other antigen-presenting cells include, for example, but are not limited to, C-lectins such as MMR ("macrophage mannose receptor") (CD206) (SEQ ID NO: 1), DEC-205 (CD205) (SEQ ID NO: 2), Dectin 1 (SEQ ID NO: 3), Dectin 2 (SEQ ID NO: 4), Langerin (CD 207) (SEQ ID NO: 5), DC-SIGN ("dendritic cell-specific ICAM-3-grabbing non-integrin, ICAM being an abbreviation for "intercellular adhesion molecule") (CD 209) (SEQ ID NO: 6), BDCA-2 ("blood dendritic cell antigen 2 protein") (SEQ ID NO: 7), DCIR ("dendritic cell immunoreceptor") (SEQ ID NO: 8), CLEC-1, ASGPR ("asialoglycoprotein receptor") (SEQ ID NO: 9), or CIRE (SEQ ID NO: 13). DC-SIGN is a calcium-dependent, type II C-type lectin, that is DC-specific ligand for ICAM-3 expressed on naïve T cells. DC-SIGN may promote a transient clustering between a DC and T cell, thus allowing the DC to screen numerous T cells for an appropriately matched T cell receptor. Dectin-1, a DC-specific type II C-type lectin that contains a cytoplasmic immunoreceptor tyrosine-based activation motif (ITAM), may inhibit or promote T cell proliferation.

In some cases, the lectin is expressed in the dendritic cells and/or other antigen-presenting cells, but are not substantially expressed in other cells, i.e., the lectin may be expressed in other cells (i.e., non-dendritic or non-antigen-presenting cells), but in quantities such that the binding of carbohydrates to the lectin in those cells has no measurable effect on the behavior of those cells. In certain instances, the lectin is not detectable in other, non-dendritic or non-antigen-presenting cells. Examples of such lectins include DC-SIGN, CLEC-1, Dectin-1, Dectin-2, BDCA-2, or CIRE.

The lectin expressed by the dendritic cells and/or other antigen-presenting cells, in some embodiments, may be a lectin that comprises one or more carbohydrate-recognition domain ("CRD"), a domain having about 115 to 130 amino acid residues, including 14 invariant and 18 highly conserved amino acid residues. The CRD is shown in FIG. 9A and SEQ ID NO: 10; comparative CRD's from other species are shown as SEQ ID NO:11 and SEQ ID NO: 12. The domain may be able to bind one or more carbohydrates, including the antigen-carbohydrate conjugates further described herein. Examples of lectins that include a CRD include those described above. The lectin comprising a CRD may be a Type I membrane lectin (oriented such that the N terminus is extracellular) or a Type II membrane lectin (oriented such that the N terminus is cytoplasmic).

The carbohydrate may be any carbohydrate that can bind the lectin that is expressable on the surface of a dendritic cell and/or other antigen-presenting cell. In some cases, the carbohydrate may be derived from the Lewis blood group antigens, for example, to preferentially target DC-SIGN. As used herein, a "carbohydrate" (or, equivalently, a "sugar") is a saccharide (including monosaccharides, oligosaccharides and polysaccharides) and/or a molecule (including oligomers or polymers) derived from one or more monosaccharides, e.g., by reduction of carbonyl groups, by oxidation of one or more terminal groups to carboxylic acids, by replacement of one or more hydroxy group(s) by a hydrogen atom, an amino group, a thiol group or similar heteroatomic groups, etc. The term "carbohydrate" also includes derivatives of these compounds. Non-limiting examples of carbohydrates include allose ("All"), altrose ("Alt"), arabinose ("Ara"), erythrose, erythrulose, fructose ("Fru"), fucosamine ("FucN"), fucose ("Fuc"), galactosamine ("GalN"), galactose ("Gal"), glucosamine ("GlcN"), glucosaminitol ("GlcN-ol"), glucose ("Glc"), glyceraldehyde, 2,3-dihydroxypropanal, glycerol ("Gro"), propane-1,2,3-triol, glycerone ("1,3-dihydroxyacetone"), 1,3-dihydroxypropanone, gulose ("Gul"), idose ("Ido"), lyxose ("Lyx"), mannosamine ("ManN"), mannose ("Man"), psicose ("Psi"), quinovose ("Qui"), quinovosamine, rhamnitol ("Rha-ol"), rhamnosamine ("RhaN"), rhamnose ("Rha"), ribose ("Rib"), ribulose ("Rut"), sorbose ("Sor"), tagatose ("Tag"), talose ("Tal"), tartaric acid, erythraric/threaric acid, threose, xylose ("Xyl"), or xylulose ("Xul"). In some cases, the carbohydrate may be a pentose (i.e., having 5 carbons) or a hexose (i.e., having 6 carbons); and in certain instances, the carbohydrate may be an oligosaccharide comprising pentose and/or hexose units, e.g., including those described above. A "monosaccharide," is a carbohydrate or carbohydrate derivative that includes one saccharide unit, e.g., as described above. Similarly, a "disaccharide," a "trisaccharide," a "tetrasaccharide," a "pentasaccharide," etc. respectively has 2, 3, 4, 5, etc. saccharide units. An "oligosaccharide," as used herein, has 1-20 saccharide units, and the saccharide units may be joined in any suitable configuration, for example, through alpha or beta linkages, using any suitable hydroxy moiety, etc. The oligosaccharide may be linear, or branched in certain instances. In some cases, the carbohydrate may be mulitmeric, i.e., comprising more than one saccharide chain.

As used herein, the term "bind," with respect to a receptor and a ligand (e.g., a carbohydrate, a carbohydrate derivative, a carbohydrate conjugate, etc.), is given its ordinary meaning as used in the art, i.e., a recognition between the receptor and the ligand. Such binding interactions may involve ionic bonds, hydrogen bonds, van der Waals bonds, metal ligand bonds, dative bonds, coordinated bonds, hydrophobic interactions, or the like. Recognition between the receptor and the ligand may be quantified using a binding affinity constant ($K_d$). Thus, in some embodiments of the invention, a carbohydrate may bind a lectin with a binding affinity of at least about 100 pM, and in some cases, the binding affinity may be at least about 1 nM, at least about 10 nM, at least about 100 nM, or at least about 1 micromolar or more. Those of ordinary skill in the art will be able to determine whether a given carbohydrate is able to bind a given lectin, and at what binding affinity, using no more than routine experiments. Examples of suitable techniques for quantitatively determining binding affinity constants, for example, equilibrium dialysis, fluorescence quenching, surface plasmon resonance, etc. In some, but not all, embodiments of the invention, the carbohydrate specifically binds the lectin, i.e., the carbohydrate binds the lectin with a binding affinity that is greater than for other known lectins. The carbohydrate may also be chosen, in certain cases, so as to be able to bind and/or specifically bind to a specific region of the lectin, such as a CRD within the lectin.

In some cases, the carbohydrate may be determined by screening a library of carbohydrates to identify those carbohydrates able to bind the lectin. Carbohydrates within the library are exposed to a lectin that is expressed on dendritic cells and/or other antigen-presenting cells, and the binding affinity between carbohydrates within the library and the lectin is determined, e.g., as described above. A non-limiting example of a screening technique for carbohydrates is D. M. Ratner, et al., "Probing Protein-Carbohydrate Interactions with Microarrays of Synthetic Oligosaccharides," *ChemBioChem*, 5:379-383, 2004, incorporated herein by reference. Those carbohydrates having suitable binding affinities may then be used in conjunction with the methods of the invention. For example, the carbohydrate may be conjugated to a suitable antigen, e.g., for administration to a subject. By "conjugate" is meant a molecular compound formed by the joining of at least two distinct agents (e.g., a carbohydrate and an antigen) or the process of forming such a molecule. Accordingly, an "antigen-carbohydrate conjugate" is formed from one, two, three or more oligosaccharides that are bound to an antigen or antigen-mimetic.

Figure 10:
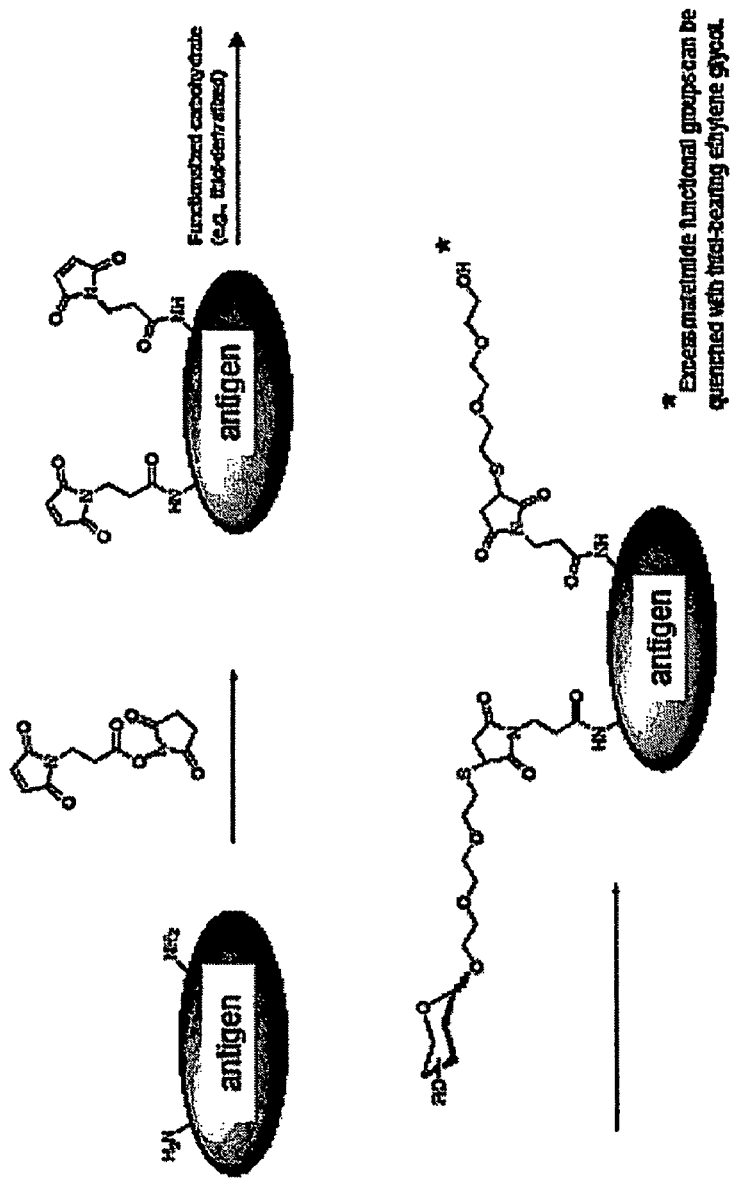
FIG. 10 depicts a conjugation scheme applicable to thiol-modified carbohydrates.

One set of embodiments of the invention is directed to carbohydrates containing one or more mannose residues, i.e., a "mannan." For example, the carbohydrate may have at least 2 mannose residues, at least 3 mannose residues, at least 4 mannose residues, at least 5 mannose residues, etc., optionally in combination with other, non-mannose residues, including those described above. In some cases, a majority of the carbohydrate residues are mannose residues. The mannose residues may be chosen so as to be able to bind and/or specifically bind a lectin expressed on dendritic cells and/or other antigen-presenting cells, e.g. DC-SIGN. Non-limiting examples of mannose-containing carbohydrates are shown by structures 1-6 in FIG. 1. In the figure, antigens may be conjugated to, for example, the thiol (—SH) or acetamide (—NHAc) moieties on the end of the carbohydrate molecule. Another example of a mannose-containing carbohydrate conjugated to an antigen is shown in FIG. 10 ("Ag" represents the antigen).

Any technique can be used to conjugate the carbohydrate and the antigen, for instance, covalently, for example, using solid phase synthesis. Those of ordinary skill in the art will know of suitable techniques for conjugating the carbohydrate to an antigen, e.g., as described above. Examples of suitable techniques are described in the Examples, under the header "Carbohydrate Modification of Ovalbumin." An exemplary approach is also illustrated in FIG. 10, which provides a conjugation scheme applicable to thiol-modified carbohydrates. Another example of a suitable technique can be seen in D. M. Ratner, et al., "A Linear Synthesis of Branched High-Mannose Oligosaccharides from the HIV-1 Viral Surface Envelope Glycoprotein gp120," *Eur. J. Org. Chem.*, 2002(5): 826-833, 2002, incorporated herein by reference, including any publicly-available supporting information. The conjugation between the carbohydrate and the antigen may be direct or indirect, e.g., a linking agent or a material may separate the carbohydrate and the antigen. For example, the linking agent or material may be a peptide, an alkyl group or an alkyl derivative, poly(ethylene glycol), a particle, a carrier, or the like.

In some embodiments of the invention, the composition may further comprise homologs, analogs, derivatives, enantiomers and/or functionally equivalent compositions thereof of the compositions of the invention. An "analog" is a compound which may differ in structure from a reference compound, but which fulfills a similar function. Such homologs, analogs, derivatives, enantiomers and functionally equivalent compositions thereof of the compositions may also be used in any of the assays described above. It will be understood that the skilled artisan will be able to manipulate the conditions in a manner to prepare such homologs, analogs, derivatives, enantiomers and functionally equivalent compositions. Homologs, analogs, derivatives, enantiomers and/or functionally equivalent compositions which are about as effective or more effective than the parent compound are also intended for use in the methods of the invention. Synthesis of such compositions may be accomplished through typical chemical modification methods such as those routinely practiced in the art.

Certain embodiments of the present invention involve a method comprising providing any of the compositions described herein, and performing a combinatorial synthesis on the composition, preferably to obtain homologs, analogs, derivatives, enantiomers and functionally equivalent compositions thereof of the composition. An assay may be performed with the homolog, analog, derivative, enantiomer or functionally equivalent composition to determine its effectiveness. The combinatorial synthesis can involve subjecting a plurality of the compositions described herein to combinatorial synthesis, using techniques known to those of ordinary skill in the art.

In some cases, the antigen-carbohydrate conjugate may include a hapten. A "hapten" is a substance, typically having a low molecular weight (e.g., a small organic molecule or a peptide), which, although not capable of provoking a specific immune response when isolated by itself, is able to enhance the immune response to a chemical species (i.e., a "carrier") to which it is attached and/or is a component of, e.g., an epitope of the antigen. The immune response may include antibodies directed against the hapten. In one set of embodiments, a portion of an antigen (e.g., an epitope) is the hapten. In another set of embodiments, the hapten is a molecule that is bound to either or both the antigen and the carbohydrate. For instance, the hapten may be a linking agent between the antigen and the carbohydrate. Non-limiting examples of haptens include certain drugs, simple sugars, amino acids, small peptides, phospholipids, triglycerides, etc.

Immune responses can also be induced or augmented by the co-administration or co-linear expression of cytokines or B7-1/2 co-stimulatory molecules in combination with the compositions of the invention. The cytokines can be administered directly with the compositions, and/or may be administered in the form of a nucleic acid vector that encodes the cytokine, such that the cytokine can be expressed in vivo. In one embodiment, the cytokine is administered in the form of a plasmid expression vector. The term "cytokine" is used as a generic name for a diverse group of soluble proteins and peptides which act as humoral regulators at nano- to picomolar concentrations and which, either under normal or pathological conditions, modulate the functional activities of individual cells and tissues. By "modulate" is meant to alter (i.e., increase or decrease). These proteins also mediate interactions between cells directly and regulate processes taking place in the extracellular environment. Non-limiting examples of cytokines include, but are not limited to IL-1, IL-2, IL-4, IL-5, IL-6, IL-7, IL-10, IL-12, IL-15, IL-18 granulocyte-macrophage colony stimulating factor (GM-CSF), granulocyte colony stimulating factor (GCSF), interferon-gamma, interferon-alpha, tumor necrosis factor-alpha, tumor necrosis factor-beta, TGF-gamma, FLT-3 ligand, CD40 ligand, etc.

Adjuvants

In certain embodiments of the invention, the antigen-carbohydrate conjugate may be administered in conjunction with an adjuvant. An "adjuvant," as used herein, is any molecule or compound that can enhance an immune response or function as a depot for an antigen. Examples of adjuvants include adjuvants that create a depot effect, immune stimulating adjuvants, adjuvants that create a depot effect and stimulate the immune system, and mucosal adjuvants.

An "adjuvant that creates a depot effect" as used herein is an adjuvant that causes an antigen to be slowly released in the body, thus prolonging the exposure of immune cells to the antigen. This class of adjuvants includes but is not limited to alum (e.g., aluminum hydroxide, aluminum phosphate), or emulsion-based formulations including mineral oil, non-mineral oil, water-in-oil or oil-in-water-in oil emulsion, oil-in-water emulsions, such as Seppic ISA series of Montamide adjuvants (e.g., Montamide ISA 720, AirLiquide, Paris, France), MF-59 (a squalene-in-water emulsion stabilized with Span 85 and Tween 80, Chiron Corporation), and PROVAX (an oil-in-water emulsion containing a stabilizing detergent and a micelle-forming agent, IDEC, Pharmaceuticals Corporation).

An "immune stimulating adjuvant" is an adjuvant that causes activation of a cell of the immune system. It may, for instance, cause an immune cell to produce and secrete cytokines. This class of adjuvants includes but is not limited to saponins purified from the bark of the $Q.$ $saponaria$ tree, such as QS21 (a glycolipid that elutes in the 21 t peak with HPLC fractionation, Aquila Biopharmaceuticals, Inc.), poly(di(carboxylatophenoxy)phosphazene) (PCPP polymer, Virus Research Institute), derivatives of lipopolysaccharides such as monophosphoryl lipid A (MPL, Ribi ImmunoChem Research, Inc.), muramyl dipeptide (MDP, Ribi) and threonyl-muramyl dipeptide (t-MDP, Ribi), OM-174 (a glucosamine disaccharide related to lipid A, OM Pharma SA), and $Leishmania$ elongation factor (a purified $Leishmania$ protein, Corixa Corporation).

"Adjuvants that create a depot effect and stimulate the immune system" are those compounds which have both of the above-identified functions. This class of adjuvants includes but is not limited to ISCOMS (immunostimulating complexes which contain mixed saponins, lipids and form virus-sized particles with pores that can hold antigen, CSL), SB-AS2 (SmithKline Beecham adjuvant system #2, which is an oil-in-water emulsion containing MPL and QS21: SmithKline Beecham Biologicals), SB-AS4 (SmithKline Beecham adjuvant system #4 which contains alum and MPL), non-ionic block copolymers that form micelles such as CRL 1005 (these contain a linear chain of hydrophobic polyoxypropylene flanked by chains of polyoxyethylene, Vaxcel, Inc.), and Syntex Adjuvant Formulation (SAF, an oil-in-water emulsion containing Tween 80 and a nonionic block copolymer, Syntex Chemicals, Inc.).

A "mucosal adjuvant" as used herein is an adjuvant that is capable of inducing a mucosal immune response in a subject when administered to a mucosal surface in conjunction with an antigen. Mucosal adjuvants include but are not limited to bacterial toxins, for example, cholera toxin and cholera toxin derivatives (e.g., CT B subunit, CTD53, CTK97, CTK104, CTD53/$K_{63}$, CTH54, $CTN_{107}$, CTE114, CTE112K, CTS61F, CTS106, CTK63, etc.), $Zonula$ $occludens$ toxin, $Escherichia$ $coli$ heat-labile enterotoxin, labile toxin and labile toxin derivatives (e.g., LT B subunit (LTB), LT7K, LT61F, LT112K, LT118E, LT146E, LT192G, LTK63, LTR72, etc.), Pertussis toxin and Pertussis toxin derivatives (e.g., PT-9K/129G), Lipid A derivatives (e.g., monophosphoryl lipid A, MPL), muramyl dipeptide derivatives, bacterial outer membrane proteins (e.g., outer surface protein A (OspA) lipoprotein of $Borrelia$ $burgdorferi$, outer membrane protein of $Neisseria$ $meningitidis$, etc.), oil-in-water emulsions (e.g., MF59), aluminum salts, saponins, etc.

Pharmaceutical Formulations and Methods of Administration

Another aspect of the invention provides a method of administering any of the above-described compositions to a subject. When administered, the compositions of the invention may be applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject.

Any of the compositions of the present invention may be administered to the subject in a therapeutically effective dose. A "therapeutically effective" or an "effective" amount or dose, as used herein means that amount necessary to induce immunity or tolerance within the subject, and/or to enable the subject to more effectively resist a disease (e.g., against foreign pathogens, cancer, an autoimmune disease, etc.). When administered to a subject, effective amounts will depend on the particular condition being treated and the desired outcome. A therapeutically effective dose may be determined by those of ordinary skill in the art, for instance, employing factors such as those further described below and using no more than routine experimentation.

In some embodiments, a therapeutically effective amount can be initially determined from cell culture assays. For instance the effective amount of a composition of the invention useful for inducing dendritic cell response can be assessed using the in vitro assays with respect to a stimulation index. The stimulation index can be used to determine an effective amount of a particular composition of the invention for a particular subject, and the dosage can be adjusted upwards or downwards to achieve desired levels in the subject. Therapeutically effective amounts can also be determined from animal models. The applied dose can be adjusted based on the relative bioavailability and potency of the administered composition. Adjusting the dose to achieve maximal efficacy based on the methods described above and other methods are within the capabilities of those of ordinary skill in the art. These doses can be adjusted using no more than routine experimentation.

In administering the compositions of the invention to a subject, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired compositional levels, local or systemic, depending upon the mode of administration. The doses may be given in one or several administrations per day. In the event that the response of a particular subject is insufficient at such doses, even higher doses (or effectively higher doses by a different, more localized delivery route) may be employed to the extent that subject tolerance permits. Multiple doses per day are also contemplated in some cases to achieve appropriate systemic levels of the composition within the subject or within the active site of the subject.

The dose of the composition to the subject may be such that a therapeutically effective amount of the composition reaches the active site of the composition within the subject, i.e., dendritic cells and/or other antigen-presenting cells within the body. The dosage may be given in some cases at the maximum amount while avoiding or minimizing any potentially detrimental side effects within the subject. The dosage of the composition that is actually administered is dependent upon factors such as the final concentration desired at the active site, the method of administration to the subject, the efficacy of the composition, the longevity of the composition within the subject, the timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, or current state of health of the subject may also influence the dose required and/or the concentration of the composition at the active site. Variations in dosing may occur between different individuals or even within the same individual on different days. It may be preferred that a maximum dose be used, that is, the highest safe dose according to sound medical judgment. Preferably, the dosage form is such that it does not substantially deleteriously affect the subject. In certain embodiments, the composition may be administered to a subject as a preventive measure. In some embodiments, the inventive composition may be administered to a subject based on demographics or epidemiological studies, or to a subject in a particular field or career.

Administration of a composition of the invention may be accomplished by any medically acceptable method which allows the composition to reach its target, i.e., dendritic cells and/or other antigen-presenting cells within the body. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the composition within the subject without causing clinically unacceptable adverse effects.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally, sublingually, through parenteral injection or implantation, via surgical administration, or any other method of administration where access to the target by the composition of the invention is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the active compound. Other oral compositions suitable for use with the invention include solutions or suspensions in aqueous or non-aqueous liquids such as a syrup, an elixir, or an emulsion. In another set of embodiments, the composition may be used to fortify a food or a beverage.

In certain embodiments of the invention, the administration of the composition of the invention may be designed so as to result in sequential exposures to the composition over a certain time period, for example, hours, days, weeks, months or years. This may be accomplished, for example, by repeated administrations of a composition of the invention by one of the methods described above, or by a sustained or controlled release delivery system in which the composition is delivered over a prolonged period without repeated administrations. Administration of the composition using such a delivery system may be, for example, by oral dosage forms, bolus injections, transdermal patches or subcutaneous implants. Maintaining a substantially constant concentration of the composition may be preferred in some cases.

The composition may also be administered on a routine schedule, but alternatively, may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the composition on a daily basis, every two days, every three days, every four days, every five days, every six days, a weekly basis, a bi-weekly basis, a monthly basis, a bimonthly basis or any set number of days or weeks there-between, every two months, three months, four months, five months, six months, seven months, eight months, nine months, ten months, eleven months, twelve months, etc. Alternatively, the predetermined routine schedule may involve administration of the composition on a daily basis for the first week, followed by a monthly basis for several months, and then every three months after that. Any particular combination would be covered by the routine schedule as long as it is determined ahead of time that the appropriate schedule involves administration on a certain day.

In some cases, the composition is administered to the subject in anticipation of an allergic event in order to prevent an allergic event. The allergic event may be, but need not be limited to, an asthma attack, seasonal allergic rhinitis (e.g., hay-fever, pollen, ragweed hypersensitivity) or perennial allergic rhinitis (e.g., hypersensitivity to allergens such as those described herein). In some instances, the composition is administered substantially prior to an allergic event. As used herein, "substantially prior" means at least six months, at least five months, at least four months, at least three months, at least two months, at least one month, at least three weeks, at least two weeks, at least one week, at least 5 days, or at least 2 days prior to the allergic event.

Similarly, the composition may be administered immediately prior to an allergic event (e.g., within 48 hours, within 24 hours, within 12 hours, within 6 hours, within 4 hours, within 3 hours, within 2 hours, within 1 hour, within 30 minutes or within 10 minutes of an allergic event), substantially simultaneously with the allergic event (e.g., during the time the subject is in contact with the allergen or is experiencing the allergy symptoms) or following the allergic event. In order to desensitize a subject to a particular allergen, the conjugate containing that antigen or allergen may be administered in very small doses over a period of time, consistent with traditional desensitization therapy.

Other delivery systems suitable for use with the present invention include time-release, delayed release, sustained release, or controlled release delivery systems. Such systems may avoid repeated administrations of the composition in many cases, increasing convenience to the subject. Many types of release delivery systems are available and known to those of ordinary skill in the art. They include, for example, polymer-based systems such as polylactic and/or polyglycolic acids, polyanhydrides, polycaprolactones and/or combinations of these; nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, and 5,736,152), or diffusional systems in which an active component controls the release rate (for example, as described in U.S. Pat. Nos. 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Combination Therapies

Administration of the composition can be alone, or in combination with other therapeutic agents and/or compositions, for example, used to treat allergies, infectious disease, cancers, etc.

For instance, examples of therapeutic agents and drugs that can be used in combination with one or more compositions of the invention for the treatment of allergy include, but are not limited to, one or more of: PDE-4 inhibitors, bronchodilator (e.g., salmeterol, salbutamol, albuterol, terbutaline, D2522/ formoterol, fenoterol, bitolterol, pirbuerol, methylxanthines such as theophylline, orciprenaline, etc.), beta-2 agonists (e.g., albuterol, bitolterol, pirbuterol, terbutaline, etc.), $K^+$ channel openers, VLA-4 antagonists, neurokin antagonists, TXA2 synthesis inhibitors, xanthanines, arachidonic acid antagonists, 5-lipoxygenase inhibitors, thromboxin A2 receptor antagonists, thromboxane A2 antagonists, inhibitors of 5-lipox activation proteins, protease inhibitors, chromolyn sodium, or medocromil. Other examples of potentially useful allergy medicaments include, but are not limited to, loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, HSR 609, prostaglandins, steroids (e.g., beclomethasone, fluticasone, tramcinolone, budesonide, budesonide, etc.), corticosteroids (e.g., beclomethasome dipropionate, budesonide, flunisolide, fluticaosone, propionate, triamcinoone acetonide, dexamethasone, methylprednisolone, prednisolone, prednisone etc.), immunomodulators (e.g., anti-inflammatory agents, leukotriene antagonists such as zafirlukast or zileuton, IL-4 muteins, soluble IL-4 receptors, immunosuppressants such as tolerizing peptide vaccine, anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, etc), downregulators of IgE (e.g., peptides or other molecules with the ability to bind to the IgE receptor, monoclonal antibodies against IgE, certain polypeptides capable of blocking the binding of the IgE antibody, etc.). Still other potentially useful immunomodulators include neuropeptides that have been shown to have immunomodulating properties, for example, substance P.

The term "cancer," as used herein, may include, but is not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stomal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In general, an effective amount of the compositions of the invention for treating cancer will be that amount necessary to inhibit mammalian cancer cell proliferation in situ. Those of ordinary skill in the art are well-schooled in the art of evaluating effective amounts of anti-cancer agents.

The term "cancer treatment" as used herein, may include, but is not limited to: chemotherapy, radiotherapy, adjuvant therapy, or any combination of these methods. Aspects of cancer treatment that may vary include, but are not limited to, dosages, timing of administration or duration or therapy; and such aspects may or may not be combined with other treatments, which may also vary in dosage, timing, and/or duration. Another cancer treatment is surgery, which may be utilized either alone or in combination with any of the previously-described treatment methods. One of ordinary skill in the medical arts can determine an appropriate cancer treatment for a subject.

Non-limiting examples of anti-cancer agents and drugs that can be used in combination with one or more compositions of the invention for the treatment of cancer include, but are not limited to, one or more of: 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, a7atyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collistnycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galoCitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, R11 retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

Other examples of agents useful in the treatment of cancer include, but are not limited to, one or more of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMIVIUNE-1, CEACIDE, Pretarget, NovoMAb-G2, TNT, Gliomab-H, GNI-250, EMD-72000, LymphoCide, CMA 676, Monopharm-C, 4B5, ior egf. r3, ior c5, BABS, anti-FLK-2, MDX-260, ANA Ab, SMART 1D10 Ab, SMART ABL 364 Ab and ImmuRAIT-CEA.

An "infectious disease" as used herein, refers to a disorder arising from the invasion of a host, superficially, locally, or systemically, by an infectious microorganism. Infectious microorganisms include, but are not limited to, bacteria, viruses, fungi, molds, etc. Examples of therapeutic agents and drugs that can be used in combination with one or more compositions of the invention for the treatment of infectious disease include anti-microbial agents, antibacterial agents, antiviral agents, nucleotide analogs, antifungal agents antibiotics, etc. Such agents and/or drugs include naturally-occurring or synthetic compounds that are capable of killing or inhibiting infectious microorganisms. The type of anti-microbial agent useful according to the invention will depend upon the type of microorganism with which the subject is infected or at risk of becoming infected.

Antibiotics potentially useful in the invention include broad spectrum antibiotics and narrow spectrum antibiotics. Antibiotics that are effective against a single organism or disease and not against other types of bacteria, are generally referred to as limited spectrum antibiotics. In general, antibacterial agents are cell wall synthesis inhibitors, such as beta-lactam antibiotics (e.g., carbapenems and cephalolsporins, including cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, etc.), natural penicillins, semi-synthetic penicillins (e.g., ampicillin, carbenicillin, oxacillin, aziocillin, mezlocillin, piperacillin, methicillin, dicloxacillin, nafcillin, etc.), ampicillin, clavulanic acid, cephalolsporins, bacitracin, etc.; cell membrane inhibitors (e.g., polymyxin, amphotericin B, nystatin, imidazoles including clotrimazole, miconazole, ketoconazole, itraconazole, fluconazole, etc.); protein synthesis inhibitors (e.g., tetracyclines, chloramphenicol, macrolides such as erythromycin, aminoglycosides such as streptomycin, rifampins, ethambutol, streptomycin, kanamycin, tobramycin, amikacin, gentamicin, tetracyclines (e.g., tetracycline, minocycline, doxycycline, and chlortetracycline, etc.), erythromycin, roxithromycin, clarithromycin, oleandomycin, azithromycin, chloramphenicol, etc.); nucleic acid synthesis or functional inhibitors (e.g., quinolones, co-trimoxazole, rifamycins, etc.); competitive inhibitors (e.g., sulfonamides such as gantrisin, trimethoprim, etc.).

Antiviral agents are compounds which prevent infection of cells by viruses or replication of the virus within the cell. There are several stages within the process of viral infection which can be blocked or inhibited by antiviral agents. These stages include attachment of the virus to the host cell (e.g., immunoglobulin, binding peptides, etc.), uncoating of the virus (e.g. amantadine), synthesis or translation of viral mRNA (e.g. interferon), replication of viral RNA or DNA (e.g. nucleoside analogs), maturation of new virus proteins (e.g. protease inhibitors), budding and release of the virus, etc.

Nucleotide analogs are synthetic compounds which are similar to nucleotides, but which may have an incomplete or abnormal deoxyribose or ribose group. Nucleotide analogs include, but are not limited to, acyclovir, gancyclovir, idoxuridine, ribavirin, dideoxyinosine, dideoxycytidine, and zidovudine (azidothymidine).

Antifungal agents are useful for the treatment and prevention of infective fungi. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, terbinafine, etc. Other anti-fungal agents function by breaking down chitin (e.g. chitinase) or immunosuppression (501 cream).

Therapeutic Formulations

In certain embodiments of the invention, a composition can be combined with a suitable pharmaceutically acceptable carrier, for example, as incorporated into a liposome, incorporated into a polymer release system, or suspended in a liquid, e.g., in a dissolved form or a colloidal form. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. A pharmaceutically acceptable carrier may be sterile in some cases. The term "carrier" denotes an organic or inorganic ingredient, which may be natural or synthetic; with which one or more active compounds of the invention are combined to facilitate the application of the composition. The carrier may be co-mingled or otherwise mixed with one or more active compounds of the present invention, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

In some embodiments, the compositions of the invention include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In some embodiments, the present invention includes the step of bringing a composition of the invention into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, the compositions of the present invention may be present as a pharmaceutically acceptable salt. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

Kits

The present invention also provides any of the above-mentioned compositions in kits, optionally including instructions for use of the composition. That is, the kit can include a description of use of the composition for participation in any mechanism described herein. A "kit," as used herein, typically defines a package or an assembly including one or more of the compositions of the invention, and/or other compositions associated with the invention, for example, as previously described. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject. When the composition provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for the compositions are well known, and are available in the literature. The solvent will depend on the composition and the mode of use or administration.

A kit of the invention may, in some cases, include instructions in any form that are provided in connection with the compositions of the invention in such a manner that one of ordinary skill in the art would recognize that the instructions are to be associated with the compositions. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner. Instructions may also provide for administering the composition by any suitable technique as previously described, for example, orally, intravenously, pump or implantable delivery device, or via another known route of drug delivery.

The invention also involves, in another aspect, promotion of the use of the compositions of the invention according to any of the techniques described herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following examples are intended to illustrate certain embodiments of the present invention, but do not exemplify the full scope of the invention.

Dendritic cells and the immune response In recent years the dual immunological function of dendritic cells has become increasingly appreciated. On the one hand, dendritic cells are the most potent of the professional antigen-presenting cells (APCs) in initiating immune responses to pathogens; in the absence of infection, however, dendritic cells play a second, crucial role of maintaining peripheral tolerance by regulating the numbers and states of self-reactive T cells. Given the importance of dendritic cells in orchestrating the human immune system along these two paths, strategies that can selectively access these different functions will greatly advance immunotherapy and facilitate the design of more rational, mechanistic vaccines. The selective modulation of dendritic cells function in the steady state, however, will depend upon the ability to specifically target dendritic cells and dendritic cell subsets.

One approach to accessing dendritic cells in vivo consists of targeting dendritic cell-specific surface receptors with ligand-antigen or ligand mimetic-antigen conjugates that deliver targeted antigens to the antigen processing/presentation machinery of dendritic cells via receptor-mediated endocytosis. One such manifestation of this strategy involves chemically coupling an antibody against a defined dendritic cell surface receptor to an antigen of interest. Antibody targeting of the dendritic cells integrin CD11c, for example, has been reported to dramatically improve the kinetics and quality of antibody responses against a model antigen in mice. At the other end of the immunological spectrum of responses, Steinman and colleagues targeted the C-type lectin DEC-205 with anti-DEC-205-antigen conjugates and demonstrate the dendritic cell-mediated induction of T cell tolerance[2-4]. These studies demonstrate that targeting dendritic cells in vivo can led to defined immunological outcomes, and serve to underscore the fact that targeting different receptors on the same cell type can produce dramatically different results. This latter facet is probably due in large part to the differential activation of signal transduction pathways downstream of receptor ligation.

While antibodies can offer unparalleled specificity for their cognate antigens, as a therapeutic agent they have the distinct disadvantages of being very expensive to produce and immunogenic in many patients. In addition to these issues, there may be circumstances in which more versatile chemistries are required for the formation of an antigen conjugate than those offered by the antibody's protein sequence. Thus, a need exists for developing robust, therapeutically useful methods of accessing dendritic cells in vivo.

As reported in more detail below, the use of synthetic carbohydrate structures offers an alternative to antibody-based targeting of dendritic cells. Dendritic cells express a number of cell surface lectins of the C-type class that recognize carbohydrate ligands appended to glycoproteins and, in some cases, mediate adsorptive uptake of bound ligand. With carbohydrate chemistry at a stage where biologically useful quantities of complex oligosaccharide can be routinely prepared[5] and with glycan microarrays that can aid in the determination of highly specific lectin-ligand interactions[6], the requisite tools are in place to pursue a dendritic cell targeting strategy founded upon lectin-carbohydrate interactions.

During a microarray study of the dendritic cell lectin DC-SIGN, lectin recognition of proteins chemically modified with structure 3-1, which is shown in FIG. 1, was observed. These results suggested that high-mannose oligosaccharides could be successfully used to target dendritic cells. The utility of this approach is demonstrated herein using mouse dendritic cells and T cells which facilitate tracking of T cell responses to dendritic cell-presented antigen in a physiological in vivo setting. The examples provided below report the successful evaluation of these conjugates' ability to enhance presentation of antigenic peptides to T cells and the application of these conjugates in an in vivo setting.

EXAMPLE 1

Carbohydrate Modification of a Model Antigen Leads to Enhanced Presentation

To examine the ability of high-mannose oligosaccharide-antigen conjugates to engage DC surface receptors such as lectins and led to presentation through the MHC class I and class II pathways, a series of ovalbumin (OVA) conjugates bearing structures shown in FIG. 1 (structures 3-1 thru 3-7) was prepared. OVA is a useful model antigen to work with as it is known to be presented on H-2K$^b$ MHC class I molecules to CD8$^+$ T cells and I-A$^b$ MHC class II molecules to CD4$^+$ T cells[3]; transgenic mice bearing only these T cell receptor specificities have been generated and were employed here to monitor the T cell responses to DC-presented peptides.

Figure 2A:
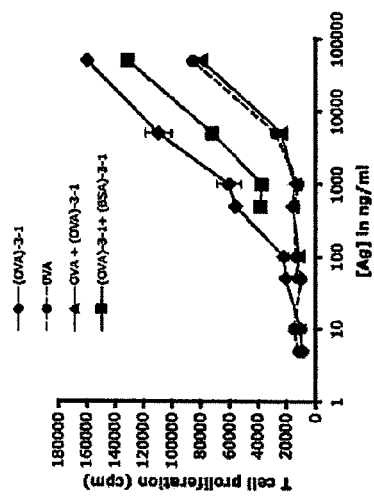
FIGS. 2A, 2B, 2C and 2D are four panels showing that carbohydrate modification of OVA led to enhanced presentation to antigen specific T cells.

OVA was modified with the heterobifunctional crosslinker SMCC to introduce maleimide functional groups; incubation with thiol-bearing saccharides (structures 3-1 thru 3-7 in FIG. 1) led to the formation of carbohydrate-OVA conjugates with an average coupling efficiency of 40% (FIG. 2A). An average of three saccharides were added per molecule of OVA, leading to a change in OVA molecular weight from 45 kDa to 48-50 kDa, depending on the appended structure.

Figure 2B:
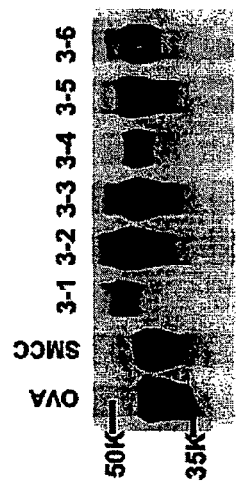

The ability of these conjugates to enhance antigen uptake by dendritic cells was assessed in comparison to unmodified OVA by incubating graded doses of conjugate and OVA with unfractionated splenocytes (containing T cells, B cells, dendritic cells, macrophages) isolated from OTII (CD4$^+$) transgenic mice. The ability of dendritic cells to present antigenic peptides derived from targeted proteins was measured as a function of T cell proliferation in response to those presented peptides. T cell proliferation is quantified by [$^3$H]thymidine incorporation during cellular division. All conjugates tested resulted in a reproducible enhancement of antigen uptake and presentation to T cells when compared to unmodified OVA over the same dosage range (FIG. 2B).

Figure 2C:
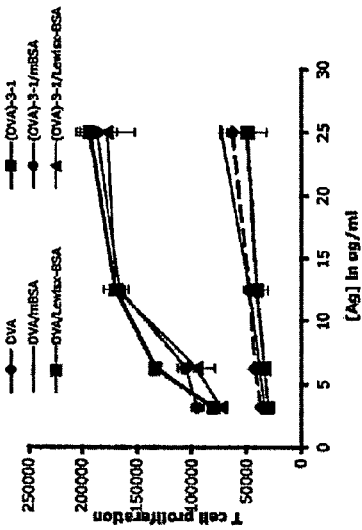

Among the structures tested, the nonasaccharide 3-1 led to the greatest enhancement of T cell proliferation compared to OVA. To verify that this enhancement was due to the carbohydrate moiety attached to OVA, splenocytes were incubated with conjugate (OVA)-3-1 in the presence and absence of an unrelated protein, bovine serum albumin (BSA) that was also modified with 3-1. Because peptides derived from BSA cannot be recognized by the transgenic OTII cells, competitive inhibition of OVA-3-1 uptake by (BSA)-3-1 led to a corresponding diminution of OTII proliferation (FIG. 2C), indicating that uptake of (OVA)-3-1 was due to the appended oligosaccharide. Co-incubation of unmodified BSA did not affect (OVA)-3-1 promoted enhancements. To ensure that the (OVA)-3-1 conjugate was not directly activating T cells and inducing their proliferation, a small amount (0.05 μg mL$^{-1}$) of (OVA)-3-1 was added to the graded doses of unmodified OVA. If (OVA)-3-1 directly activated T cells an enhanced level of T cell proliferation would be detected across the graded does of OVA compared to OVA alone. This did not occur (FIG. 2C). The T cell response curves for OVA vs. OVA+(OVA)-3-1 were identical. Furthermore, the addition of (OVA)-3-1 to purified T cells in the absence of antigen-presenting cells did not led to T cell proliferation nor did it enhance the mixed leukocyte reaction between dendritic cells and allogeneic T cells. This shows that these conjugates did not directly activate T cells or dendritic cells.

Figure 2D:
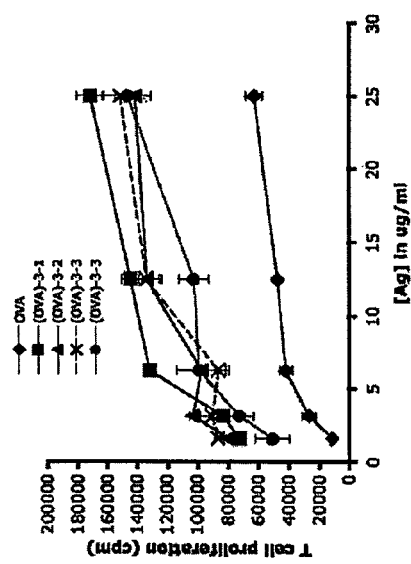

Microarray analysis of glycan binding by DC-SIGN revealed that DC-SIGN recognized both complex branched mannans, like 3-1 and 3-2, as well as dense arrays of linear oligosaccharides and simple monosaccharides. In addition, carbohydrate profiling by another group has revealed that DC-SIGN can recognize non-sialylated Lewis blood group antigens (e.g. Lewis$^x$)[7]. As five murine homologs of DC-SIGN have been described[8], with one homolog, CIRE, being expressed exclusively in CD8α CD4$^+$ and CD8 α CD4 dendritic cells[9], the possibility that a lectin with a DC-SIGN-like binding profile may be mediating the recognition and uptake of (OVA)-3-1 was tested by incubating splenocytes with (OVA)-3-1 in the presence or absence of mannose-derivatized BSA (mBSA) or Lewis$^x$-modified BSA (Lewis$^x$-BSA). Next the ability of these conjugates to inhibit uptake of (OVA)-3-1 was measured (FIG. 2D). Neither mBSA nor Lewis$^x$-BSA significantly impair endocytosis and presentation of (OVA)-3-1 to OTII T cells. These results demonstrated that neither of these conjugates serves as a ligand for the receptor mediating uptake of (OVA)-3-1.

Accessing the transporter of antigenic peptides (TAP) and thereby achieving cross-presentation of antigen by dendritic cells to MHC class I restricted CD8+ T cells led to efficient stimulation of these T cells and, in the steady state, their apoptotic deletion from the T cell repertoire[3]. To determine if the receptor promoting (OVA)-3-1 uptake can process proteins through the MHC class I pathway, (OVA)-3-1 and OVA were incubated with unfractionated splenocytes isolated from OTI (CD8$^+$) mice. The T cells from transgenic OTI mice recognized an eight amino acid residue sequence (SIINFEKL (SEQ ID NO: 14)) derived from OVA and were therefore utilized to gauge the efficiency of DC presentation of MHC class I antigenic peptides. A moderate (10-fold) increase in the efficiency of MHC class I presentation with (OVA)-3-1 as compared to OVA alone was observed (FIG. 3A). Inhibition of this enhancement is again achieved by co-incubation with (BSA)-3-1 and, as shown for OTII T cells, (OVA)-3-1 did not achieve this enhancement via direct activation of T cells.

In an effort to determine whether the increased efficiencies of antigen presentation obtained via (OVA)-3-1 could be attained via simple monosaccharide-antigen conjugates, our splenocyte incubations with (OVA)-3-6 and (OVA)-3-7 was repeated (FIG. 3B). The monosaccharide mannose 3-6 only weakly enhanced presentation to CD4$^+$ T cells, while galactose 3-7 did not promote increased presentation at all as compared to unmodified OVA. Interestingly, co-incubation of (OVA)-3-6 with (BSA)-3-1 did not inhibit the uptake of (OVA)-3-6, indicating that the monosaccharide 3-6 and the more complex 3-1 are likely to interact with different DC receptors.

EXAMPLE 2

Figures 4A, 4B, 4C, 4D:
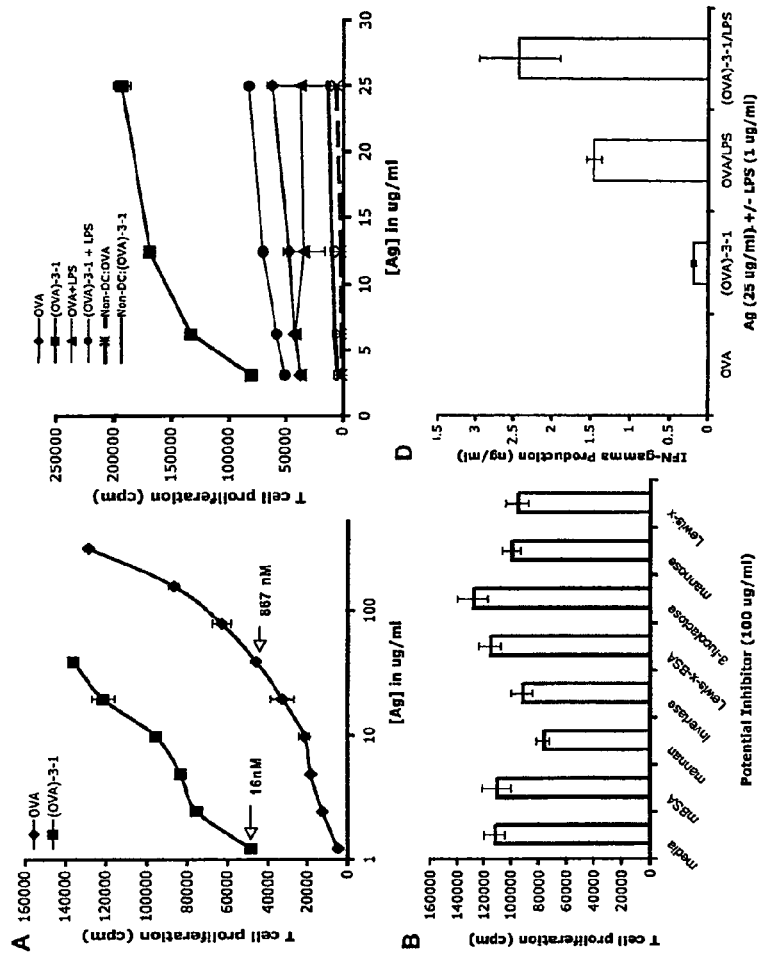
FIGS. 4A, 4B, 4C and 4D are graphs showing that CD11c$^+$ dendritic cells are the main antigen presenting cells presenting 3-1-targeted antigen.

Enhanced T Cell Proliferation is Due to Uptake Exclusively by CD11c$^+$ Dendritic Cells To confirm that the increased T cell proliferation observed with (OVA)-3-1 was due to the selective uptake of this conjugate by dendritic cells and not B cells or macrophages, purified CD11c$^+$ dendritic cells were prepared from wild-type C57BL/6 mice and the OVA-specific T cells from transgenic OTII mice (see Materials & Methods). The in vitro antigen presentation assays described above were then repeated. A parallel titration series of (OVA)-3-1 and unmodified OVA revealed that CD11c$^+$ dendritic cells were highly efficient at capturing and presenting (OVA)-3-1 as compared to soluble OVA, even at concentrations as low as 16 nM (FIG. 4 A). By comparison, >50-fold more unmodified OVA was required to obtain similar levels of T cell proliferation. When B cells and macrophages were used as antigen-presenting cells in place of purified dendritic cells, the resulting T cell responses were negligible (FIG. 4C), providing strong confirmation that CD11c$^+$ dendritic cells are the main antigen-presenting cells mediating uptake and presentation of (OVA)-3-1 to OTII T cells. This latter result was also very strong confirmation that (OVA)-3-1 does not directly activate T cells; if direct activation of T cells by (OVA)-3-1 was operative, the levels of T cell proliferation observed here should have equaled the levels observed when dendritic cells are used as the antigen-presenting cells.

Attempts to inhibit (OVA)-3-1 internalization with mBSA and Lewis$^x$-BSA (FIG. 2D) may have missed the inhibitory effect of these molecules due to their potential effects on other non-dendritic cell types present in the splenocyte population. To address this possibility and to try other potential inhibitors of (OVA)-3-1 internalization, the inhibition experiment was repeated with purified dendritic cells and T cells (FIG. 4B). Neither mBSA nor Lewis$^x$-BSA were inhibitory; even when utilized at a>300-fold excess over (OVA)-3-1; soluble Lewis$^x$ had marginal effects on (OVA)-3-1 presentation by dendritic cells. Likewise, a 1000-fold excess of soluble mannose only reduced conjugate presentation by 10%. More inhibitory were the complex mannan derived from *Saccharomyces cerevisiae* (31%) and the high-mannose-bearing glycoprotein invertase (18%). The inhibition of (OVA)-3-1 presentation with an invertase concentration of 0.5 μM compared to the 0.55 mM mannose concentration required to achieve similar levels of inhibition further underscores the specificity exhibited by the high-mannose oligosaccharide receptor on dendritic cells. Incubation with the common milk oligosaccharide, 3-fucosyllactose (3-FL), had no inhibitory action; in fact, a slight increase in T cell proliferation was observed with 3-FL (14%).

Some dendritic cell lectins are known to be strongly down-regulated upon toll-like receptor (TLR) engagement with bacterial agonists[9,10]. To determine whether the receptor mediating (OVA)-3-1 uptake was similarly down-regulated upon TLR engagement or if dendritic cell maturation induced by TLR agonists would further augment the presentation of (OVA)-3-1 to OTII T cells, an in vitro presentation assay was performed in which lipopolysaccharide (LPS), a potent agonist of the toll-like receptor 4 signaling pathway[11], was added to graded doses of OVA or (OVA)-3-1 (FIG. 4C). As for the macrophage mannose receptor[12] and the DC-SIGN murine homolog CIRE, where TLR agonists led to dramatically decreased mRNA production for each lectin, a significant decrease (60%) in presentation of (OVA)-3-1 to T cells was observed as a result of TLR-mediated dendritic cell maturation. In the case of unmodified OVA, TLR activation led to a 30% decrease in antigen presentation to OTII T cells. Without being tied to one particular theory, this was likely due to a decrease in macropinocytosis by dendritic cells on the path to terminal differentiation.

Despite the significant diminution of (OVA)-3-1 presentation by dendritic cells upon TLR-4 stimulation, targeting with nonasaccharide 3-1 remained better than targeting by unmodified OVA, implying that antigen capture of (OVA)-3-1 by dendritic cells prior to full maturation was considerably more efficient than capture of unmodified OVA. Likewise, analysis of pro-inflammatory IFN-γ production by responding OTII T cells (FIG. 4D) showed an average of 40% less IFN-γ produced by T cells responding to OVA than to. (OVA)-3-1.

EXAMPLE 3

Both CD8α$^+$ and CD8 α$^-$ DC Subsets Present Carbohydrate-Modified Antigen

Figure 5:
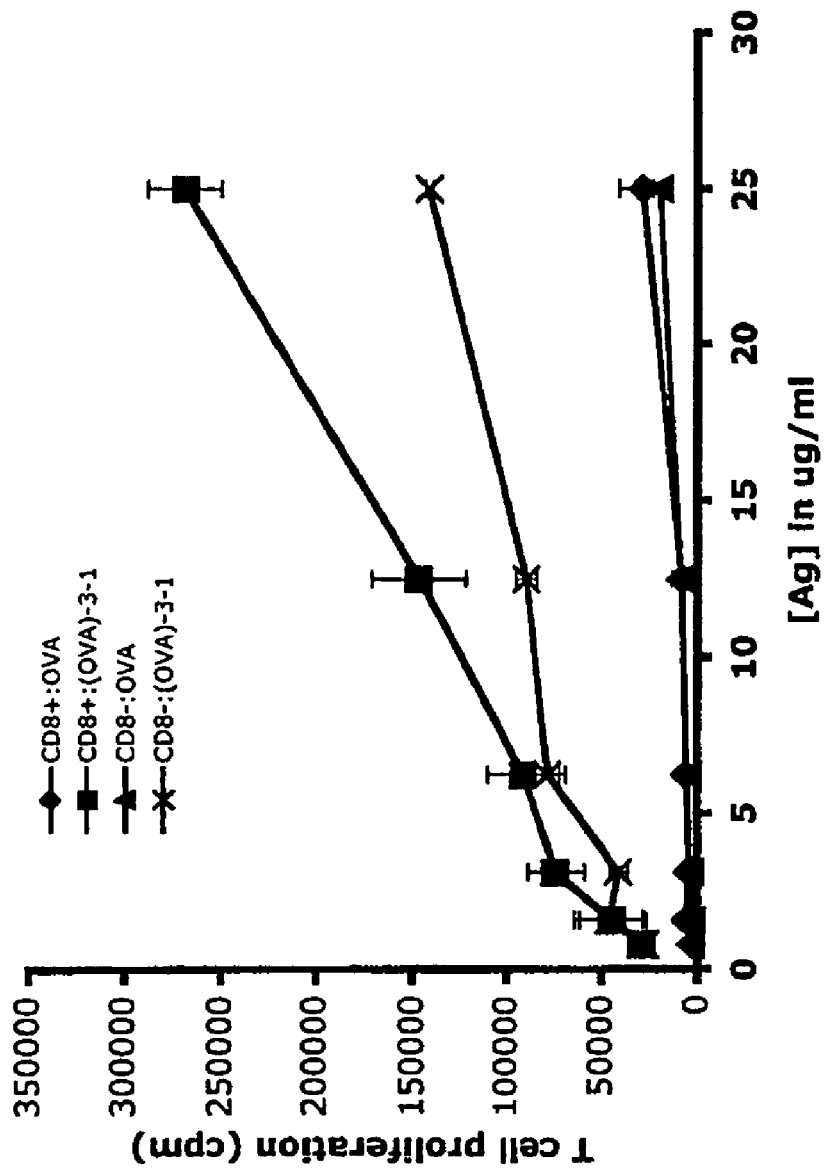
FIG. 5 is a graph showing that both dendritic cell subsets, i.e., cells that are CD8α+ and CD8α$^-$, can present (OVA)-301. CD11c+ dendritic cells were stained with antibody against CD8α and I-A$^b$ MHC class H molecules and sorted into their respective CD8α+ and CD8α$^-$ populations. $2\times10^4$ cells of each subtype were incubated with $1\times10^5$ purified OTII T cells with graded doses of OVA or (OVA)-3-1 for eighty-four hours with [$^3$H]thymidine (1 µCi) added for the last twelve hours. All data points were performed in triplicate.

These results established that dendritic cells are the main antigen presenting cells capable of capture, processing, and presentation of (OVA)-3-1, but did not indicate whether a particular subset of dendritic cells was responsible for this activity. In the mouse, there are three subsets of dendritic cells, which are defined by their expression of the cellular antigens CD8 and CD4, namely CD8 α$^+$CD4$^-$, CD8α$^-$CD4$^+$, and CD8αCD4[14,15]. Many functional differences among these subsets have been described and it has been argued that the CD8α$^+$ subset may be solely responsible for maintaining peripheral tolerance while the CD8α$^-$ subset induces immunity to captured antigen[14] To determine if the high-mannose receptor was restricted to a particular subset, a fluorescence cell sorter was used to separate dendritic cells into their respective CD8α$^+$ and CD8α$^-$ subsets. Each subset was then tested for its ability to present OVA and (OVA)-3-1 to OTII T cells (FIG. 5). Surprisingly, while OVA is only weakly presented to T cells by the individual subsets, (OVA)-3-1 is presented by each subset, with the CD8α$^+$ subset being approximately 2-fold more efficient than the CD8α$^-$ subset. Thus, both dendritic cell subsets expressed a receptor capable of binding nonasaccharide 3-1 and mediating uptake of antigens modified with this oligosaccharide.

EXAMPLE 4

In Vivo Targeting of Dendritic cells Leads to Antigen-Specific T Cell Activation In order to determine the immunological implications of (OVA)-3-1 internalization and presentation by dendritic cells in vivo, the technique of adoptive transfer (FIG. 6A) was employed to track the T cell responses to DC presented antigen[15]. In this technique, ovalbumin-specific transgenic CD4$^+$ T cells expressing a specific isoform of the surface antigen CD45 (designated CD45.2) was injected intravenously into a strain of mice that were genetically identical except at the CD45 locus. Using antibodies against the CD45.2 isoform expressed by the donor T cells, these cells can be distinguished from recipient cells during the course of an experiment.

CD45.2$^+$ VA-specific T cells were transferred to B6.Ly5.2/Cr (CD45.1$^+$) recipients and, after a twenty-four hour rest period, the mice were immunized subcutaneously with PBS, OVA or (OVA)-3-1. After seventy-two hours, cells were isolated from the draining inguinal lymph nodes and counted by FACS to determine the extent of OTII cell division induced by the immunization regimen (FIG. 6B). Immunization with the (OVA)-3-1 conjugate led to proliferation of OTII specific T cells in the draining lymph node, with a doubling of total OTII cell number compared to soluble OVA. In addition, an appreciable increase in the total OTII cell number in the spleen of (OVA)-3-1 immunized mice was observed, implying that the injected conjugate was capable of accessing dendritic cells at sites distal from the site of immunization. Thus, (OVA)-3-1 targeted dendritic cells in vivo and that targeting led to improved antigen-specific T cell activation relative to soluble antigen (FIGS. 6B and 6C).

EXAMPLE 5

Co-injection of a TLR Agonist did not Increase the Efficiency of (OVA)-3-Targeting Relative to Soluble OVA A number of studies have indicated that dendritic cell presentation of poorly immunogenic soluble proteins can be significantly augmented by the concomitant administration of an adjuvant or agent that promotes the release of pro-inflammatory cytokines, such as TNF-α or IL-1β[16,17]. These cytokines aid in the recruitment and activation of monocytes and dendritic cells at the site of administration, thereby promoting a heightened immune response. As indicated by the in vitro data, TLR-4 signaling significantly attenuated (OVA)-3-1 processing and presentation by dendritic cells. To assess these results in vivo, the adoptive transfer system described above was used with the following modification. Prior to transferring the CD45.2 OTII T cells to the B6.Ly5.2/Cr recipients, the cells were stained with 5-(6)-carboxyfluorescein diacetate succinimidyl ester (CFSE), a cell-permeable dye that freely crosses the cell membrane; once inside the cell, however, cellular esterases hydrolyze the CFSE's ester functional groups to generate a negatively charged molecule that cannot cross back across the cell membrane. This dye is used to monitor cell division by flow cytometry as each successive cell division leads to a dilution of CFSE among the daughter cells.

Figures 7A, 7B:
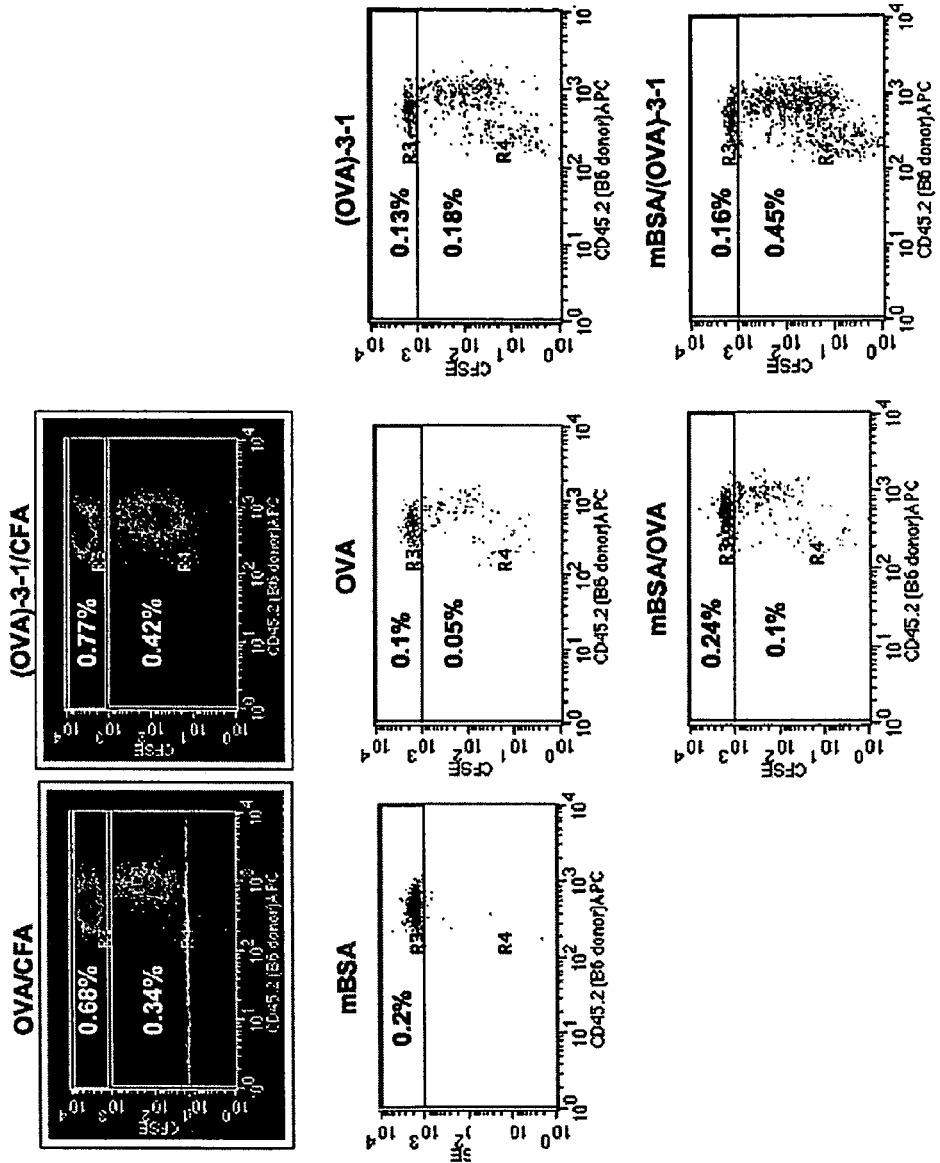
FIGS. 7A and 7B are a series of dot plots showing that inflammatory stimuli dampen the effects of DC targeting by (OVA)-3-1.

To administer pro-inflammatory stimuli at the same time as soluble antigen, OVA and (OVA)-3-1 were emulsified in Complete Freund's Adjuvant (CFA) prior to immunization. CFA is an oil-based mixture of mycobacterial cell wall components that is known to induce strong TH1 T cell responses[2]. Seventy-two hours after immunization, cells from the draining lymph nodes were isolated and analyzed by flow cytometry for cell number and divisions (FIG. 7A). While the total OTH cell number increased for (OVA)-3-1 administered CFA relative to (OVA)-3-1 in PBS (FIGS. 6B and 7B), this did not result in a corresponding increase in cell number relative to OVA/CFA. In fact, the enhancement previously observed relative to soluble OVA (FIG. 6B) was largely diminished. Tracking CFSE dilution due to cell division indicated that more OTII cells are actively dividing in mice that received (OVA)-3-1/CFA than those that received OVA/CFA, suggesting that dendritic cells targeted by (OVA)-3-1 are slightly more efficient at promoting antigen-specific T cell proliferation under these pro-inflammatory conditions. Without being tied to one particular theory, one potential reason for this observation could be that dendritic cells targeted with (OVA)-3-1 produced more peptide-MHC class II complexes than those targeted by OVA as receptor-mediated endocytosis delivered more antigen to the cell before full maturation was reached[10].

The strong enhancements observed with (OVA)-3-1 in vitro (FIG. 4A) appeared to be substantially reduced in vivo, possibly because other cells expressing a lectin capable of engaging high-mannose oligosaccharides could be competing with dendritic cells for (OVA)-3-1. Of the mammalian lectins known to bind high-mannose oligosaccharides, langerin (CD207)[20] and the mannose receptor (CD206)[19] are appropriately anatomically positioned to bind and internalize injected (OVA)-3-1. Langerin is expressed in the Langerhans cells of the skin and has been demonstrated to mediate uptake of high-mannose bearing glycoproteins by these cells and cells transfected with cDNA encoding this receptor[20,21]. The mannose receptor is expressed in many different tissues and cell types. Its expression has also been confirmed on the endothelial venules leading to draining lymph nodes and on endothelial cells of the skin[19].

To address the possibility that (OVA)-3-1 was competitively endocytosed by langerin and/or the mannose receptor, antigen immunizations were performed using a large excess of soluble mannose in an attempt to competitively inhibit this activity. This treatment did not led to an improvement of (OVA)-3-1-mediated targeting when the level of T cell proliferation was monitored as described above. Since most lectins have weak affinities for monosaccharides, these experiments were repeated with BSA that was modified with approximately 25 mannose residues per protein molecule (mBSA). Mannose-derivatized BSA was selected because it is a nanomolar ligand for the mannose receptor[22,23] and has is bound by langerin in solid-phase binding studies[21]. Mice that had received CFSE-labeled OTH T cells were immunized with mBSA, OVA, (OVA)-3-1, OVA plus mBSA, or (OVA)-3-1 plus mBSA and their T cell responses were analyzed at seventy-two hours (FIG. 7B). Consistent with previous experiments, (OVA)-3-1 led to a 2-fold increase in OTII T cell number compared to OVA. In addition, 58% of these T cells had undergone cell division, whereas only 33% of the T cells in OVA immunized mice had divided. As anticipated, T cells from mice that had been immunized with mBSA did not proliferate because the appropriate antigenic peptides for OTII cells cannot be derived from BSA. Surprisingly, when OVA and (OVA)-3-1 were injected along with mBSA, an increase in OTII T cell number was observed for both antigens. The T cell number increased 1.7-fold in mice receiving soluble OVA plus mBSA (mBSA/OVA, FIG. 7B, bottom row) relative to the cell number observed for OVA alone. Likewise, the number of OTII T cells increased 2-fold for mBSA/(OVA)-3-1 injections as compared to (OVA)-3-1 alone. In addition to having an increased OTII cell numbers, both OVA and (OVA)-3-1 had increased percentages of cells undergoing cell division: T cells from the OVA group increased from 33% to 42%, while T cells from the (OVA)-3-1 group increased from 55% to 74%.

It is not yet clear how the co-injection of mannose-derivatized BSA led to the enhancements of T cell proliferation observed for both administered antigens. Without being tied to any particular theory, one explanation could be the presence of bacterial endotoxin in the mBSA preparation that could serve, to activate dendritic cells at the site of injection and thereby increase antigen presentation as was observed with CFA (FIG. 7A). Each mBSA preparation used throughout these studies was tested, and each had at most negligible quantities of endotoxin. Alternatively, mBSA blocked lectins that would normally bind OVA (which bears one N-linked glycan at Asn-392) in addition to (OVA)-3-1. This would enable both antigens to reach the draining lymph nodes where they would be endocytosed by dendritic cells and presented to T cells. Since the addition of mBSA to in vitro antigen presentation assays did not significantly effect presentation of (OVA)-3-1 or OVA to T cells (FIGS. 2D and 4B), with unfractionated OTII splenocytes or purified dendritic cells and T cells, mBSA does not appear to directly activate dendritic cells or T cells.

EXAMPLE 6

Oligosaccharide-Mediated Targeting of Steady State Dendritic cells Leads to a State of T Cell Unresponsiveness At three days post-immunization, antibody-based targeting of the DEC-205 receptor led to a 6.5-fold enhancement of T cell activation relative to non-targeted antigen[2]. After seven days, however, the activated T cell population diminished in number by 88% and the remaining T cells were unresponsive to systemic challenge of antigen in the highly stimulatory adjuvant CFA. A reproducible 2-fold enhancement of T cell activation with (OVA)-3-1 immunization was observed in saline and a four-fold enhancement with mBSA/(OVA)-3-1 immunization relative to OVA in saline. To more fully understand the immunological consequences of these enhancements, OVA peptide (100 µg) was administered in CFA at eight days post-antigen immunization and the T cells' ability to respond to DC-presented peptide in vitro was assayed two days later (FIGS. 8A and 8B)[2]: A positive control for T cell tolerance, consisting of a high dose administration of OVA peptide (100 µg) in Incomplete Freund's Adjuvant was also included. This regimen has been shown in a number of different studies to led to a state of T cell unresponsiveness upon antigen rechallenge[24,25].

At two days post-antigen rechallenge in CFA a significant difference was observed in the number of OTII cells in (OVA)-3-1 relative to unmodified OVA (7.8-fold) and the saline control group (6-fold). Co-injection of mBSA with (OVA)-3-1 (mBSA/(OVA)-3-1) led to a 21-fold increase in OTII number compared to soluble OVA while the OTII number in the peptide/IFA control group was 26-fold greater than OVA.

Figure 8B:
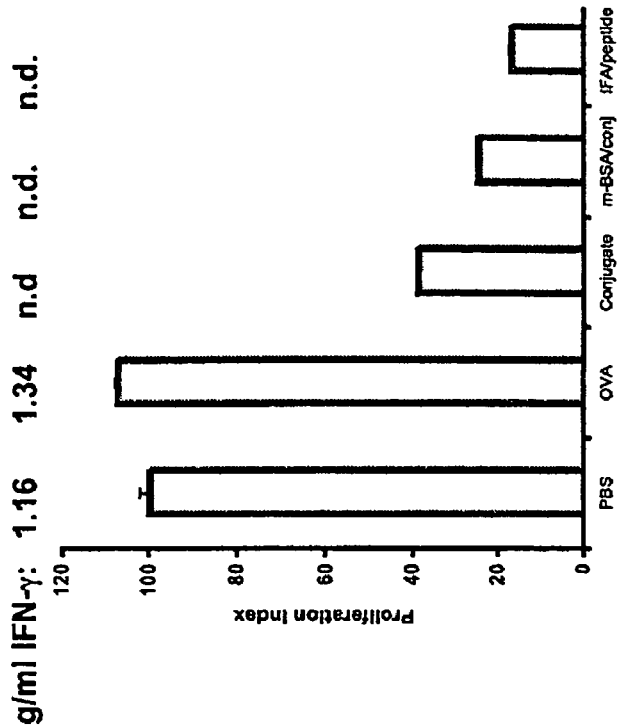
FIGS. 8A and 8B are a series of dot plots (FIG. 8A) and a graph (FIG. 8B) showing that the oligosaccharide-mediated targeting of steady state dendritic cells leads to T cell tolerance.

When the T cells from each group were tested for their ability to respond to dendritic cell-presented peptide in vitro, OTII cells from the (OVA)-3-1 and mBSA/(OVA)3-1 groups were significantly less responsive to antigen than cells from the PBS and OVA groups, as was the peptide/IFA control group (FIG. 8B). This was very surprising as the OVA-specific T cell numbers for the (OVA)-3-1 and mBSA/(OVA)-3-1 groups were so much higher than the OVA and PBS groups, indicating that the latter two groups were strongly activated by the peptide/CFA rechallenge while the (OVA)-3-1 and mBSA/(OVA)-3-1 (in addition to the peptide/IFA control) were refractory to antigenic stimulation. This lack of antigen responsiveness is further mirrored in the levels of IFN-γ produced by these cells during the twenty-four hours of peptide stimulation in vitro (FIG. 8 B). While T cells from the PBS and OVA groups produced IFN-γ (and no IL-4) in response to peptide, indicating their TH1 status, there was no detectable IFN-γ produced by the (OVA)-3-1, mBSA/(OVA)-3-1, or, as previously documented, the peptide/IFA groups. IL-4 was also not detected in these groups, indicating a lack of T cell polarization. This indicated that nonasaccharide 3-1-mediated antigen delivery to dendritic cells in the steady state led to peripheral T cell unresponsiveness to subsequent antigenic rechallenge. In sum, a panel of synthetic analogs of the high-mannose oligosaccharide (Man)9(GlcNAc)2 was used to prepare carbohydrate-OVA conjugates for targeting murine dendritic cells. These synthetic oligosaccharides were shown to target $CD11c^+CD8\alpha^+$ and $CD11c^+CD8\alpha^-$ dendritic cells, deliver their appended antigen to the requisite antigen processing pathways for presentation on MHC class I and class II molecules, and enhanced activation of OVA-specific T cells. In vivo, a conjugate comprising (OVA)-3-1 targeted dendritic cells and increased the efficiency of presentation by 2-fold compared to unmodified OVA. The simultaneous co-injection of a highly mannosylated neoglycoprotein, mBSA, further enhanced dendritic cell targeting by (OVA)-3-1, leading to a 4-fold enhancement of T cell proliferation relative to OVA. Finally, the immunological outcome of oligosaccharide-mediated targeting of antigen to dendritic cells in the steady state promoted antigen-specific T cell tolerance, or unresponsiveness, demonstrated by the fact that T cells obtained from (OVA)-3-1 immunized mice were refractory to restimulation with peptide in vitro and do not appear to produce TH1 or TH2 cytokines.

Figure 8A:
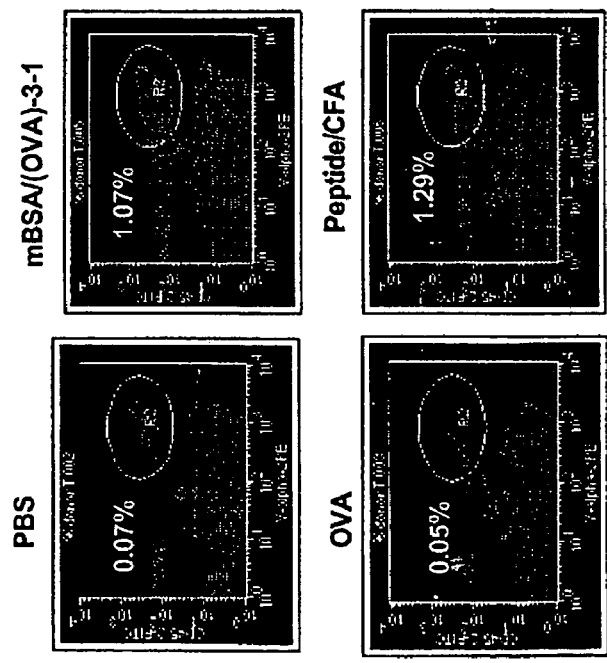

Appreciable T cell deletion induced by (OVA)-3-1 targeting of dendritic cells in vivo was not observed (FIG. 8A). The expanded T cell population likely represents T regulatory cells induced by steady state dendritic cells. To determine if this is the case, OTII T cells are isolated from (OVA)-3-1 immunized mice (in parallel with PBS, OVA and peptide/IFA immunizations) and assayed for foxp3 expression by intracellular staining or PCR. (Foxp3 is an inhibitor of transcription that serves as a specific molecular signature of T regulatory cells)[26]. In addition, T cells are tested at the functional level for their ability to suppress the proliferation of naive $CD4^+$ T cells incubated with OVA-presenting Dendritic cells. While analyzing these cells for their status as canonical $CD4^+ CD25^+ foxp3^+$ Tregs, their capacity to produce IL-10 and TGF-b is also assessed, as these are functional markers for another class of suppressive T cells referred to as TR1 cells[27]. Finally, this targeting method and the antibody-based DEC-205 targeting method are compared to determine how the nonasaccharide 3-1 compares to the anti-DEC-205 antibody and to determine whether both methods elicit the same T cell phenotype.

To identify the receptor mediating uptake of the oligosaccharides employed herein, the murine DC-SIGN homolog CIRE[10] was analyzed as a potential receptor; a cell line stably expressing this lectin was used to assay for binding and internalization of fluorophore-labeled 3-1 and fluorophore-labeled (OVA)-3-1. These experiments did not reveal any interactions between the high-mannose oligosaccharide and CIRE. Subsequent flow cytometry analysis of splenic dendritic cells with anti-CIRE antibody revealed that CIRE expression was low on $CD11c^+$ dendritic cells. The receptor may be identified biochemically, for example, by cross-linking it to bound (OVA)-3-1 and immunoprecipitating the complex with polyclonal sera raised against ovalbumin. Identification of the receptor would enable the determination of its human homolog.

These studies are the first to identify the presence of a receptor on dendritic cells that preferentially engages complex, branched oligosaccharides over simple monosaccharides and that can be targeted in vivo to effect T cell function. Accordingly, the carbohydrate-based targeting approach described here is useful as an alternative to antibody-based targeting of lectins or other surface receptors, and provides a means to rationally modulate immune cell function.

These studies were carried out using the following methods and materials.

Mice 6-12 week old female mice were used in all experiments and were maintained under specific pathogen free conditions. C57BL/6 mice were purchased from Taconic and congenic B6.Ly5.2/Cr mice were purchased from NCI-Frederick. OTI and OTII mice were bred in an in-house facility; OTI mice were genotyped by analyzing expression of $V\alpha_2 V\beta_{5.1/5.2}$ by FACS.

Antibodies

Antibodies against CD45.2 (104) and all other surface markers ($V\alpha2$/B20.1, $CD8\alpha$/53-6.7, $I-A^b$/AF6-120.1) were purchased from BD Biosciences (Mountain View, Calif.), as was streptavidin-APC. Rabbit anti-ovalbumin was purchased from Research Diagnostics (Concord Mass.).

Reagents

Mannose, invertase, mannan, and mannose-BSA, BSA, and ovalbumin were all purchased from Sigma Chemical (St.

Louis, Mo.). 3-fucosyllactose, Lewis-$^x$ and Lewis-$^x$-BSA were purchased from Dextra Laboratories (Reading, UK).

Carbohydrate Modification of Ovalbumin 1.9 mg sulfosuccinimidyl 4-[maleimidomethyl]-cyclohexane-1-carboxylate (Sulfo-SMCC, Pierce Endogen) was dissolved in 88 μL dimethylformamide (DMF) and added to 5 mg ovalbumin (OVA) in 315 μl, PBS. The reaction solution was mixed for 1 hour at room temperature. Maleimide-activated OVA was purified from nonreacted Sulfo-SMCC by gel filtration on a NAP-25 desalting column (Amersham) pre-equilibrated in PBS. The OVA fractions were collected and mixed with thiol-containing oligosaccharides (0.6 μmoles/per structure) that had been previously reduced with 1 equivalent tris-(carboxyethyl)phosphine hydrochloride (TCEP). This reaction proceeded for 12 hours at room temperature with constant mixing. Modified OVA was purified from excess oligosaccharide by multiple rounds of centrifugal ultrafiltration with Vivaspin 10,000 MW cut-off cartridges (Vivascience). Purified protein was lyophilized and stored at −20° C. until use.

Cell Culture and Proliferation Assays

Pooled inguinal lymph nodes were dissociated in 10% Fetal Bovine Serum RPMI (supplemented with 2 mM L-glutamine) and either mechanically dissociated between two glass slides or, to improve the overall cell yield, incubated in the presence of collagenase (Boehringer) and EDTA for 25 minutes at 37° C./5% CO2 to dissociate DC-T cell clusters. For antigen presentation assays with whole splenocytes, isolated spleens were injected with collagenase/EDTA, gently teased apart and incubated as described above. Splenocytes were cultured in 96-well round-bottom plates at a density of $3\times10^5$ cells/0.2 mL. In antigen presentation assays utilizing purified dendritic cells and T cells, dendritic cells were isolated from the spleens of C57BL/6 mice following collagenase/EDTA treatment by labeling the dendritic cells with commercially available magnetic microbeads linked to an anti-CD11c$^+$ antibody (Miltenyi Biotec, Bergisch Gladbach, Germany) (according to the Miltenyi Biotec protocol) and separating labeled Dendritic cells from non-dendritic cells by application of a magnetic field. Similarly, purified CDC T cells were obtained from spleens of OTII transgenic mice using magnetic beads Dynal (Oslo, Norway). Purified dendritic cells and T cells were seeded onto 96-well plates round-bottom Plates at a 1:2 DC:T cell ratio unless stated otherwise in the Figures.

For T cell proliferation assays in adoptive transfer experiments, inguinal lymph nodes from each experimental group (3 mice/group) were pooled and dissociated with collagenase/EDTA as described above. In order to ensure that the CD4+ T cells were not activated during the isolation procedure, the cells were purified by negative selection using a biotinylated antibody cocktail against CD8α, CD11b, CD45R, DX5, and Ter-119 followed by magnetic anti-biotin microbeads. Labeled cells were separated from CD$^4$+ T cells by application of a magnetic field. Purified T cells ($3\times10^5$/well) were seeded into 96-well round-bottom plates with purified CD11c$^+$ dendritic cells ($9\times10^4$/well). Synthetic OTII OVA peptide [KISQAVHAAHAEINEAG] (SEQ ID NO: 15) was added to half of the cultures at a final concentration of 100 μg mL$^{-1}$. Cultures were maintained for 24 hours with [$^3$H] thymidine (1 μCi) added for the last 10 hours. Response to OVA peptide was determined by subtracting background proliferation (no peptide) from specific, peptide-induced proliferation. The total antigen-specific (i.e., background subtracted) counts were divided by the number of OTII cells per well (obtained by flow cytometry, FIG. 8A) to determine the radioactive counts per cell. The proliferation index was calculated as the ratio of the response to OVA peptide in an experimental group to the response to OVA peptide in the PBS group.

Cell Sorting

To obtain sufficient numbers of dendritic cells for antigen presentation and cytokine analysis, C57BL/6 mice were injected with a Flt3-ligand secreting tumor cell line to promote the expansion of dendritic cells. Fourteen days after this administration the mice were sacrificed and the spleens were isolated. Dendritic cells were purified from the spleens by positive selection with anti-CD11c microbeads as described above and stained with FITC-conjugated anti-1-A$^b$ and cychrome-conjugated anti-CD8α. Cells were then sorted on a fluorescence-activated cell sorter, a MoFlo, (Dakocytomaton, Glostrup Denmark) into CD8α$^+$I-A$^{b+}$ and CD8α$^-$I-A$^{b+}$ populations. The purity of each subset was 80% with approximately 6% cross-contamination. Dendritic cells from each subset were used in antigen proliferation assays as described above (section 3.5.5).

Adoptive Transfer and CFSE Labeling

Spleens from OTII mice were mechanically dissociated, filtered, washed 2× in PBS and then resuspended at $1\times10^8$ cells mL$^{-1}$ in PBS. Cells were transferred to B6.Ly5.2/Cr mice by retro-orbital intravenous injection (200 μL/mouse). Alternatively, the cells were resuspended in RPMI (no FBS) at $5\times10^7$ cells mL$^{-1}$ after being filtered and incubated with an equal volume of 30 μM CFSE in PBS to obtain a final CFSE concentration of 15 μM. Cells were incubated in a 37° C. water-bath for 10 minutes and then washed 1× with 10% FBS/RPMI and 2× with PBS. CFSE-labeled cells were diluted to $1\times10^8$ cells mL$^{-1}$ in PBS and injected into B6.Ly5.2/Cr.

Cytokine ELISAs 75-150 μL aliquots of supernatant were sampled from antigen presentation assays at 24, 48, and 72 hours. 75 μL aliquots were removed from the antigen rechallenge assays at 14 hours, prior to the addition of [$^3$H]thymidine. 25 μL of each supernatant were diluted 1:1 with PBS/1% BSA and analyzed in triplicate for IFN-γ, IL-10, and IL-4 using DuoSet ELISA reagents from R&D Systems. The lower limit of cytokine detection in these ELISAs was approximately 0.3 ng mL$^{-1}$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "one or more."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

REFERENCES

1. Wang, et al., (2000) Proc. Natl. Acad. Sci. 97: 847-852
2. Hawiger, et al., (2001) J. Exp. Med. 194: 769-779
3. Bonifaz, et al., (2002) J. Exp. Med. 196: 1627-1638
4. Mahnke, et al., (2003) Blood. 101: 4862-4869
5. Haase, et al., (2000) Chemical Reviews. 100: 4349-4394
6. Ratner, et al., (2004) Chembiochem. 5: 1375-1383
7. Appelmelk, et al., (2003) J. Immunol. 170: 1635-1639
8. Park, et al., (2001) Int. Immunol. 13: 1283-1290
9. Caminschi, et al., (2001) Molecular Immunology. 38: 365-373
10. Sallusto, et al., (1995) J. Exp. Med. 182: 389-400
11. Kopp, et al, (2003) Curr. Opin. Immunol. 15: 396-401
12. Heath, et al., (2004) Immunol Rev. 199:9-26
13. Maldonado-Lopez, et al., (2001) Semin. Immunol. 13: 275-282
14. Inaba, et al., (1997) J. Exp. Med. 186: 665-672
15. Kearney, et al., (1994) Immunity. 1: 327-339
16. Pulendran, et al., (1998) J. Exp. Med. 188: 2075-2082
17. Reis e Sousa, et al., (1997) J. Exp. Med. 186: 1819-1829
18. Takahara, et al., (2002) Int. Immunol. 14: 433-444
19. Takahashi, et al., (1998) Cell Tissue Res. 292:311-323
20. Galustain, et al., (2004) Int. Immunol. 16: 853-866
21. Stambach, et al., (2003) Glycobiology. 13: 401-410
22. Taylor, et al., (1993) Biochem Soc. Trans. 21: 468-473
23. Taylor, et al., (1993) J. Biol. Chem. 268: 399-404
24. Aichele, et al., (1995) J. Exp. Med. 182: 261-266
25. Perez, et al., (1997) Immunity. 6: 411-417
26. Fehervari, et al., (2004) Int. Immunol. 16: 1769-1780
27. Groux, et al., (1997) Nature. 389: 737-742

What is claimed is:

1. A composition comprising at least one mannose oligosaccharide conjugated to a molecule selected from the group consisting of a protein or glycoprotein, a lipid, chemically modified lipid, or glycolipid, polysaccharide, or small molecule, wherein the composition is capable of binding to a protein present on a dendritic cell.

2. A composition comprising at least one carbohydrate conjugated to an antigen, wherein the composition is capable of binding to a carbohydrate binding protein present on an antigen presenting cell, and the carbohydrate is a mannose oligosaccharide.

3. The composition of claim 2, wherein the carbohydrate binding protein is a lectin selected from the group consisting of an I-type, S-type, P-type, or C-type lectins.

4. The composition of claim 2, wherein the addition of the oligosaccharide increases the molecular weight of the antigen by at least 5 kDa.

5. The composition of claim 2, wherein the carbohydrate is selected from the group consisting of structures 3-1 to 3-7.

6. The composition of claim 2, wherein the carbohydrate is $(Man)_9(GlcNAc)_2$.

7. The composition of claim 2, wherein the carbohydrate is conjugated to the antigen by a thiol-bearing linker.

8. The composition of claim 2, wherein the antigen is selected from the group consisting of autoimmune antigens, allergens, tumor antigens, and pathogen antigens.

9. The composition of claim 8, wherein the pathogen antigen is derived from a bacteria, virus, or fungus.

10. A composition comprising an antigen-carbohydrate conjugate that binds a lectin expressed on a human dendritic cell in vivo or ex vivo, the conjugate comprising mannose in a pharmaceutically acceptable carrier.

11. The composition of claim 10, further comprising an adjuvant or a cytokine.

12. The composition of claim 10, wherein the antigen comprises a protein, chemically-modified lipid, glycolipid, glycoprotein, polysaccharide, or small molecule.

13. The composition of claim 10, wherein the lectin comprises a sequence SEQ ID NO: 10.

14. An immunogenic composition comprising at least one mannose oligosaccharide conjugated to an antigen in a pharmaceutically acceptable excipient, wherein the mannose oligosaccharide-antigen conjugate binds a lectin that is expressed on a dendritic cell wherein the composition is capable of modulating an immune response.

15. The composition of claim 14, wherein the antigen comprises a protein, chemically-modified lipid, glycolipid, glycoprotein, polysaccharide, or small molecule.

16. A method of immunization, comprising: administering to a subject a composition comprising a conjugate of an antigen and a mannose oliqosaccharide that binds a lectin expressed on an antigen-presenting cell, wherein the composition is in an amount effective to immunize the subject to the antigen.

17. The method of claim 16, further comprising administering an adjuvant or a cytokine to the subject.

18. The method of claim 16, wherein the amount is effective to promote dendritic cell maturation.

19. The method of claim 16, wherein the mannose oligosaccharide comprises at least 2, mannose residues.

20. The method of claim 16, wherein the lectin is selected from the group consisting of an I-type, S-type, P-type, C-type lectin, a Type I or Type II C-type lectin, DC-SIGN, Dectin 1 or 2, BDCA-2, and CLEC-1.

21. The method of claim 20, wherein the lectin comprises a sequence SEQ ID NO: 10.

22. The method of claim 16, wherein the method induces immunological tolerance of the subject to the antigen.

23. The method of claim 22, wherein the amount is effective to inhibit dendritic cell maturation.

24. The method of claim 22, wherein the amount is effective to induce T cell anergy, deletion, or regulatory activity.

25. A method of modulating an immune response in a cell, the method comprising contacting a cell of a subject with a composition of claim 16, wherein the contacting modulates an immune response.

26. A method of reducing, stabilizing, or ameliorating symptoms of an immune response in a subject in need thereof, the method comprising contacting a cell of the subject with a composition of claim 1, wherein the contacting reduces, stabilizes, or ameliorates the immune response.

27. The method of claim 26, wherein the immune response is an allergic response and the method ameliorates a disease or disorder selected from the group consisting of eczema, allergic rhinitis, coryza, hay fever, conjunctivitis, bronchial asthma, allergic asthma, urticaria, atopic dermatitis, anaphylaxis, food allergy, drug allergy, and angioedema.

28. The method of claim 26, wherein the immune response is an autoimmune response and the method treats a disease or disorder selected from the group consisting of Addison's disease, autoimmune anemia, Goodpasture's syndrome, Graves' disease, Hashimoto's thyroiditis, idiopathic thrombocytopenia purpura, type I diabetes, myasthenia gravis, ankylosing spondylitis, multiple sclerosis, rheumatoid arthritis, psoriasis, Crohn's disease, scleroderma, Sjogren's syndrome, and systemic lupus erythematosus.

29. The method of claim 26, wherein the immune response is a response to a pathogen infection that is a bacterial infection, a viral infection, or a fungal infection.

30. The method of claim 26, wherein the cell is a dendritic cell that functions in an adaptive immune response.

31. The method of claim 26, wherein the cell is ex vivo or in vivo.

32. A method of enhancing antigen presentation by a cell, the method comprising contacting an antigen-presenting cell with at least one mannose oligosaccharide conjugated to an antigen or antigen mimetic, wherein the contacting enhances antigen presentation by the antigen-presenting cell.

33. A method of increasing T cell proliferation in a subject, the method comprising contacting an antigen-presenting cell with at least one mannose oligosaccharide conjugated to an antigen or antigen mimetic, wherein the contacting enhances antigen presentation by the antigen-presenting cell.

34. A kit for modulating an immune response, the kit comprising the composition of claim 1.

35. The kit of claim 34, further comprising directions for administering the composition to the subject.

36. A method of generating an antigen mannose oligosaccharide conjugate, the method comprising: conjugating an antigen to a mannose oligosaccharide able to bind a lectin that is expressed on antigen-presenting cells but is not substantially expressed on non-antigen-presenting cells.

37. The method of claim 36, wherein the antigen comprises a protein, chemically-modified lipid, glycolipid, glycoprotein, polysaccharide, or small molecule.

38. The method of claim 36, wherein the lectin comprises a sequence SEQ ID NO: 10.

39. A method for producing a conjugated antigen, the method comprising: providing a lectin that is expressed on antigen-presenting cells but is not substantially expressed on non-antigen-presenting cells; screening a carbohydrate library to identify carbohydrates able to bind the lectin; and conjugating an antigen to one of the identified carbohydrates able to bind the lectin.

40. A method of immunization, comprising: administering, to a human or mammalian subject, a composition comprising a conjugate of an antigen and a carbohydrate, comprising mannose, that is able to bind a lectin that is expressed on antigen-presenting cells, in an amount effective to immunize the subject to the antigen.

41. The method of claim 40, wherein the method induces immunological tolerance of the subject to the antigen.

42. The method of claim 41, wherein the amount is effective to inhibit dendritic cell maturation.

43. The method of claim 41, wherein the amount is effective to induce T cell anergy, deletion, or regulatory activity.

44. A method for conjugating an antigen to a carbohydrate, the method comprising: providing a lectin that is expressed on antigen-presenting cells but is not substantially expressed on non-antigen-presenting cells; screening a carbohydrate library to identify carbohydrates able to bind the lectin; and conjugating an antigen to one of the identified carbohydrates able to bind the lectin.

45. The composition of claim 8, wherein the tumor antigen is selected from the group consisting of alpha-fetoprotein, Ig-idiotype, mutant cyclin-dependent kinase 4, Pmel-17, MART-1, p15 protein, tyrosinase, MAGE 1, 2 and 3, a Gage family member, BAGE, human papilloma virus antigens E6 and E7, an Epstein-barr virus antigen, bcr-abl fusion product, gp75, oncofetal antigen, mucin, telomerase, GM2 ganglioside, GD2 ganglioside, mutant p53, mutant cdk4, p21ras, HER21neu, c-erbB-2, colorectal associated antigen (CRC)-C017-1A/GA733, APC, cyclophilin b, ga733 glycoprotein, Imp-1, EBNA-1, prostate specific antigen, pancreatic tissue antigen, prostate specific membrane antigen, thyroglobulin, carcinoembryonic antigen, NY-ESO-1, HTLV-1, cdc27, and gp100$_{Pme1117}$.

46. The composition of claim 9, wherein the virus is selected from the group consisting of Retroviridae, human immunodeficiency viruses, Picornaviridae, Calciviridae, Togaviridae, Flaviridae, Coronoviridae, Rhabdoviradae, Coronaviridae, Rhabdoviridae, Filoviridae, Paramyxoviridae, Orthomyxoviridae, Bungaviridae, Arena viridae, Reoviridae, Birnaviridae, Hepadnaviridae, Parvovirida, Papovaviridae, Adenoviridae (adenoviruses), Herpesviridae, Poxyiridae, and Iridoviridae.

47. The composition of claim 9, wherein the antigen is selected from the group consisting of human immunodeficiency virus gp120 protein, malarial Merozoite Surface Protein-1, Apical membrane protein-1, *Plasmodium falciparum* erythrocyte membrane protein, tuberculosis antigen 85 A/B, ESAT-6, tuberculosis heat shock protein 60, influenza hemaglutinin, influenza neuraminidase, hepatitis B virus antigen.

48. The composition of claim 46, wherein the human immunodeficiency virus is HIV-1.

49. The composition of claim 2, wherein the oligosaccharide is selected from the group consisting of a branched oligosaccharide, linear oligosaccharide and polysaccharide.

* * * * *